United States Patent
Yamniuk et al.

(10) Patent No.: US 12,409,223 B2
(45) Date of Patent: *Sep. 9, 2025

(54) ANTAGONISTIC CD40 MONOCLONAL ANTIBODIES AND USES THEREOF

(71) Applicant: Bristol-Myers Squibb Company, Princeton, NJ (US)

(72) Inventors: Aaron Yamniuk, Vancouver (CA); Mary Struthers, Edison, NJ (US); Stanley R. Krystek, Jr., Ringoes, NJ (US); Akbar Nayeem, Newtown, PA (US); Ginger Rakestraw, Somerville, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/453,691

(22) Filed: Aug. 22, 2023

(65) Prior Publication Data

US 2024/0124597 A1 Apr. 18, 2024

Related U.S. Application Data

(60) Continuation of application No. 17/588,518, filed on Jan. 31, 2022, now Pat. No. 11,773,178, which is a division of application No. 16/686,596, filed on Nov. 18, 2019, now Pat. No. 11,261,258.

(60) Provisional application No. 62/769,514, filed on Nov. 19, 2018.

(51) Int. Cl.
| | |
|---|---|
| C07K 16/28 | (2006.01) |
| A61K 39/395 | (2006.01) |
| A61K 47/68 | (2017.01) |
| A61P 29/00 | (2006.01) |
| A61P 37/06 | (2006.01) |
| A61K 39/00 | (2006.01) |
| C07K 14/705 | (2006.01) |
| C07K 16/46 | (2006.01) |
| C12N 15/63 | (2006.01) |

(52) U.S. Cl.
CPC ...... *A61K 39/3955* (2013.01); *A61K 47/6849* (2017.08); *A61P 29/00* (2018.01); *A61P 37/06* (2018.01); *C07K 16/2878* (2013.01); *A61K 2039/505* (2013.01); *A61K 47/68* (2017.08); *A61K 47/6803* (2017.08); *C07K 14/70578* (2013.01); *C07K 16/468* (2013.01); *C07K 2317/21* (2013.01); *C07K 2317/24* (2013.01); *C07K 2317/52* (2013.01); *C07K 2317/565* (2013.01); *C07K 2317/622* (2013.01); *C07K 2317/71* (2013.01); *C07K 2317/76* (2013.01); *C07K 2317/92* (2013.01); *C12N 15/63* (2013.01)

(58) Field of Classification Search
CPC .......... C07K 16/2878; C07K 2317/565; C07K 2317/76; A61K 39/3955
See application file for complete search history.

(56) References Cited

U.S. PATENT DOCUMENTS

| | | | |
|---|---|---|---|
| 5,530,101 A | 6/1996 | Queen et al. |
| 5,585,089 A | 12/1996 | Queen et al. |
| 5,693,762 A | 12/1997 | Queen et al. |
| 6,180,370 B1 | 1/2001 | Queen et al. |
| 6,687,673 B2 | 2/2004 | Mann |
| 6,737,056 B1 | 5/2004 | Presta |
| 7,183,387 B1 | 2/2007 | Presta |
| 8,637,032 B2 | 1/2014 | Long et al. |
| 8,674,083 B2 | 3/2014 | Presta |
| 9,090,696 B2 | 7/2015 | Barrett et al. |
| 9,475,879 B2 | 10/2016 | Suri et al. |
| 10,435,475 B2 | 10/2019 | Honczarenko et al. |
| 11,220,550 B2 | 1/2022 | Yamniuk et al. |
| 11,254,750 B2 | 2/2022 | Yamniuk et al. |
| 11,261,258 B2 | 3/2022 | Yamniuk et al. |
| 11,613,585 B2 | 3/2023 | Yamniuk et al. |
| 11,773,178 B2 | 10/2023 | Yamniuk et al. |
| 11,795,231 B2 | 10/2023 | Yamniuk et al. |
| 11,926,673 B2 | 3/2024 | Yamniuk et al. |
| 2005/0054832 A1 | 3/2005 | Lazar et al. |
| 2006/0235208 A1 | 10/2006 | Lazar et al. |
| 2007/0003546 A1 | 1/2007 | Lazar et al. |
| 2008/0057070 A1 | 3/2008 | Long et al. |
| 2008/0199471 A1 | 8/2008 | Bernett et al. |

(Continued)

FOREIGN PATENT DOCUMENTS

| | | |
|---|---|---|
| CN | 102633880 A | 8/2012 |
| CN | 102918063 A | 2/2013 |

(Continued)

OTHER PUBLICATIONS

Schwabe et al., 2018, Safety, pharmacokinetics and pharmacodynamics of multiple rising doses of BI 655064, an antagonistic anti-CD40 antibody in healthy subjects: a potential novel treatment for autoimmune diseases. *J Clin Pharmacol.* 58(12): 1566-1577.

Ralph et al., 2015, (THU0407) Preclinical characterization of a highly selective and potent antagonistic ANTI-CD40 MAB. *Annals of the Rheumatic Diseases,* 74:344.

Slade et al., 2016, (FRI0230) Assessment of safety, pharmacokinetics and pharmacodynamics of a novel anti-CD40 monoclonal antibody, CFZ533, in healthy volunteers and in rheumatoid arthritis patients. *Annals of the Rheumatic Diseases,* 75:516-517.

(Continued)

*Primary Examiner* — Zachary C Howard
(74) *Attorney, Agent, or Firm* — Banner & Witcoff, Ltd.

(57) ABSTRACT

The disclosure provides for antibodies that bind CD40, including a humanized antibody. The antibodies bind CD40 and do not exhibit CD40 agonist activity. The antibodies may comprise a modified IgG1 Fc domain, and exhibit minimal activation of immature dendritic cells. Compositions comprising antibodies, methods of use for treatment of diseases involving CD40 activity, and use in the preparation of a medicament for treatment of a disease involving CD40 activity are provided.

18 Claims, 10 Drawing Sheets

Specification includes a Sequence Listing.

(56) References Cited

U.S. PATENT DOCUMENTS

| | | |
|---|---|---|
| 2010/0331208 A1 | 12/2010 | Gao et al. |
| 2013/0149238 A1 | 6/2013 | Kavlie et al. |
| 2013/0209445 A1 | 8/2013 | Lazar et al. |
| 2013/0236470 A1 | 9/2013 | Matsuoka et al. |
| 2014/0079701 A1 | 3/2014 | Miller et al. |
| 2014/0099317 A1 | 4/2014 | Suri et al. |
| 2014/0294812 A1 | 10/2014 | Lazar |
| 2014/0335089 A1 | 11/2014 | Igawa et al. |
| 2014/0363428 A1 | 12/2014 | Igawa et al. |
| 2015/0018529 A1 | 1/2015 | Humphreys et al. |
| 2015/0210763 A1 | 7/2015 | Kuramochi et al. |
| 2015/0299296 A1 | 10/2015 | Katada et al. |
| 2015/0315284 A1 | 11/2015 | Lazar et al. |
| 2015/0337053 A1 | 11/2015 | McCarthy et al. |
| 2016/0039912 A1 | 2/2016 | Mimoto et al. |
| 2016/0075785 A1 | 3/2016 | Ast et al. |
| 2016/0145350 A1 | 5/2016 | Lonberg et al. |
| 2016/0355596 A1 | 12/2016 | Honczarenko et al. |
| 2016/0376371 A1 | 12/2016 | Ravetch et al. |
| 2018/0340031 A1 | 11/2018 | Yamniuk et al. |
| 2020/0148779 A1 | 5/2020 | Yamniuk et al. |
| 2020/0157233 A1 | 5/2020 | Yamniuk et al. |
| 2021/0054090 A1 | 2/2021 | Yamniuk et al. |

FOREIGN PATENT DOCUMENTS

| | | |
|---|---|---|
| CN | 103172731 A | 6/2013 |
| CN | 103635488 A | 3/2014 |
| CN | 104788565 A | 7/2015 |
| CN | 104918957 A | 9/2015 |
| EP | 2471813 B1 | 12/2014 |
| JP | 2008-505174 A | 2/2008 |
| JP | 2014-513953 A | 6/2014 |
| JP | 2018-526977 A | 9/2018 |
| WO | WO-2000/042072 A2 | 7/2000 |
| WO | WO-2004/099249 A2 | 11/2004 |
| WO | WO-2006/019447 A1 | 2/2006 |
| WO | WO-2006/127910 A2 | 11/2006 |
| WO | WO-2008/091954 A2 | 7/2008 |
| WO | WO-2008/137475 A2 | 11/2008 |
| WO | WO-2011/123489 A2 | 10/2011 |
| WO | WO-2012/065950 A1 | 5/2012 |
| WO | WO-2012/145673 A1 | 10/2012 |
| WO | WO-2012/149356 A2 | 11/2012 |
| WO | WO-2014/006217 A1 | 1/2014 |
| WO | WO-2014/070934 A1 | 5/2014 |
| WO | WO-2014/184545 A2 | 11/2014 |
| WO | WO-2015/0134988 A1 | 9/2015 |
| WO | WO-2016/028810 A1 | 2/2016 |
| WO | WO-2016/168716 A1 | 10/2016 |
| WO | WO-2016/196314 A1 | 12/2016 |
| WO | WO-2017/004006 A1 | 1/2017 |
| WO | WO-2017/004016 A1 | 1/2017 |
| WO | WO-2017/059196 A2 | 4/2017 |
| WO | WO-2018/065389 A1 | 4/2018 |
| WO | WO-2018/169993 A1 | 9/2018 |
| WO | WO-2018/175279 A2 | 9/2018 |
| WO | WO-2018/217976 A1 | 11/2018 |
| WO | WO-2018/218056 A1 | 11/2018 |
| WO | WO-2018/217988 A9 | 5/2019 |
| WO | WO-2019/087094 A1 | 5/2019 |
| WO | WO-2020/102728 A1 | 5/2020 |
| WO | WO-2020/106620 A1 | 5/2020 |
| WO | WO-2020/112781 A1 | 6/2020 |

OTHER PUBLICATIONS

Adams, et al. (2005) "Development of a chimeric anti-CD40 monoclonal antibody that synergizes with LEA29Y to prolong islet allograft survival," J. Immunol. 174: 542-50.
Cai et al. "C-terminal lysine processing of human immunoglobulin G2 heavy chain in vivo," Biotechnol Bioeng. 108(2): 404-12, 2011, Abstract Only.
Clinical Trials Feeds, "Study of HCD122 (Lucatumumab) and Bendamustine Combination Therapy in CD40+ Rituximab-Refractory Follicular Lymphoma," Internet at http:clinicaltrialsfeeds. org/clinical-trials/show/NCT01275209 (last updated Jan. 11, 2011).
Davies et al. (2005) "TRAF6 Is Required for TRAF2-Dependent CD40 Signal Transduction in Nonhemopoietic Cells," Mol. Cell Biol. 25(22): 9806-19.
International Preliminary Report on Patentability mailed Dec. 5, 2019 in International Application No. PCT/US2018/034315.
International Preliminary Report on Patentability mailed Dec. 5, 2019 in International Application No. PCT/US2018/034330.
International Preliminary Report on Patentability mailed Jun. 3, 2021 in International Application No. PCT/US2019/062011.
International Search Report and the Written Opinion mailed Apr. 9, 2020 in International Application No. PCT/US2019/062011.
International Search Report and Written Opinion mailed Jul. 24, 2018 for PCT/US2018/034330.
International Search Report mailed Sep. 11, 2018 in International Application No. PCT/US2018/034315.
Melvin et al., 2012, "Belatacept: A worthy alternative to cyclosporine?" J. Pharmacol Pharmacother. 3(1): 90-92.
Mimoto, F., et al., "Engineered antibody Fc variant with selectively enhanced FcγRIIb binding over both FcγRIIaR131 and FcγRIIaH131," Protein Engineering, Design and Selection 2001, 26(10): 589-598.
Nebija et al., "2-DE and MALDI-TOF-MS analysis of therapeutic fusion protein abatacept," Electrophoresis 31: 1438-1443, 2011.
Ngo et al., "Computational Complexity, Protein Structure Prediction and the Levinthal Paradox," in: The Protein Folding Problem and Tertiary Structure Prediction (Boston, Birkhäuser, 1994), Chapter 14, pp. 434-495.
Ristov et al. (2018) "Characterization of the in vitro and in vivo properties of CFZ533, a blocking and non-depleting anti-CD40 monoclonal antibody," Am J Transplant. 18(12):2895-2904. [Epub May 24, 2018].
Rowshanravan et al. 2018, "CTLA-4: a moving target in immunotherapy," Blood 131(1):58-97.
Shields et al., (2001) "High Resolution Mapping of the Binding Site on Human IgG1 for FcgRI, FcgRII, FcgRIII, and FcRn and Design of IgG1 Variants with Improved Binding to the FcgR," The Journal of Biological Chemistry, vol. 276, No. 9, pp. 6591-6604.
Vidarsson, Gestur, et al., "IgG Subclasses and allotypes: from structure to effector functions," Frontiers in Immunology, vol. 5, Oct. 20, 2014, pp. 1-17.
Vonderheide et al. (2007) "Clinical activity and immune modulation in cancer patients treated with CP-870,893, a novel CD40 agonist monoclonal antibody," J. Clin. Oncol. 25(7): 876-883.
Wells, 1990, "Additivity of Mutational Effects in Proteins." Biochemistry 29(37): 8509-8517.
Written Opinion mailed Sep. 11, 2018 in International Application No. PCT/US2018/034315.
First Office Action issued Sep. 3, 2021 in Chinese Patent Application No. 201880032964.0 (9 pages) with an English translation (11 pages).
Hoogenboom et al. (1991) "Multi-subunit proteins on the surface of filamentous phage: methodologies for displaying antibody (Fab) heavy and light chains," Nucleic Acids Res. 19(15): 4133-4137.
Nov. 23, 2021—(WO) International Search Report and Written Opinion—App PCT/US2021/047610.
Fisher Benjamin A et al, "Assessment of the anti-CD40 antibody iscalimab in patients with primary Sjögren's syndrome: a multicentre, randomised, double-blind, placebo-controlled, proof-of-concept study", NL Mar. 3, 2020 (Mar. 3, 2020), vol. 2, No. 3, p. e142-e152, Retrieved from the Internet: URL:http://dx.doi.org/10.1016/S2665-9913(19)30135-3 XP055859370 DOI: 10.1016/S2665-9913(19)30135-3 external link ISSN:2665-9913.
Anonymous, "BMS-986325 in Healthy Participants and Participants With Primary Sjögren's Syndrome—Full Text View—ClinicalTrials.gov", Dec. 24, 2020 (Dec. 24, 2020), Retrieved from the Internet: URL:https://clinicaltrials.gov/ct2/show/NCT04684654 XP055859331 [retrieved on Nov. 9, 2021].
Anonymous, "Safety, Pharmacokinetics and Preliminary Efficacy Study of CFZ533 in Patients With Primary Sjögren's Syndrome—Full Text View—ClinicalTrials.gov", Nov. 14, 2014 (Nov. 14,

(56) References Cited

OTHER PUBLICATIONS

2014), Retrieved from the Internet: URL:https://clinicaltrials.gov/ct2/show/NCT02291029 XP055859384 [retrieved on Nov. 9, 2021].

Fisher Benjamin et al, "Abstract 1784: The Novel Anti-CD40 Monoclonal Antibody CFZ533 Shows Beneficial Effects in Patients with Primary Sjogren's Syndrome: A Phase IIa Double-Blind, Placebo Controlled Randomized Trial", Arthritis & Rheumatology, John Wiley & Sons, Inc, US, vol. 69, No. Suppl. 10, Sep. 18, 2017 (Sep. 18, 2017), XP002788011 ISSN:2326-5191.

Jobling Kerry et al, "CD40 as a therapeutic target in Sjögren's syndrome", GB Jul. 3, 2018 (Jul. 3, 2018), vol. 14, No. 7, p. 535-537, Retrieved from the Internet: URL:http://dx.doi.org/10.1080/1744666X.2018.1485492 XP055859366 DOI: 10.1080/1744666X.2018.1485492 external link ISSN:1744-666X.

Albach et al., 2018, Safety, pharmacokinetics and pharmacodynamics of single rising doses of BI 655064, an antagonistic anti-CD40 antibody in healthy subjects: a potential novel treatment for autoimmune diseases. *Eur J Clin Pharmacol,* 74: 161-169.

De Genst et al., 2006, "Antibody repertoire development in camelids," *Dev Comp Immunol.* 30(1-2):187-198.

Deschacht et al., 2010, "A novel promiscuous class of camelid single-domain antibody contributes to the antigen-binding repertoire," *J Immunol.* 184(10):5696-5704. Epub Apr. 19, 2010.

Tereshko et al., 2008. "Toward chaperone-assisted crystallography: protein engineering enhancement of crystal packing and X-ray phasing capabilities of a camelid single-domain antibody (VHH) scaffold," *Protein Sci.* 17(7):1175-1187.

Sircar et al., 2011, "Analysis and modeling of the variable region of camelid single-domain antibodies," *J Immunol.* 186(11):6357-6367.

"Study of HCD122 (Lucatumumab) and Bendamustine Combination Therapy in CD40+ Rituximab-Refractory Follicular Lymphoma," Clinical Trials Feeds, on the Internet at hypertext transfer protocol: clinicaltrialsfeeds.org/clinical-trials/show/NCT01275209 (last updated Jan. 11, 2011).

Yu, X et al. (2018) "Complex Interplay between Epitope Specificity and Isotype Dictates the Biological Activity of Anti-human CD40 Antibodies" Cancer Cell 33(4): 664-675.e4.

Yamniuk AP et al. (2016) "Functional Antagonism of Human CD40 Achieved by Targeting a Unique Species-Specific Epitope" J Mol Biol. 428(14):2860-2879. Epub May 21, 2016.

Okimura K et al. (2014) "Characterization of ASKP1240, a fully human antibody targeting human CD40 with potent immunosuppressive effects" Am J Transplant. 4(6):1290-1299.

Laman JD et al. (2002) "Protection of marmoset monkeys against EAE by treatment with a murine antibody blocking CD40 (mu5D12)" Eur J Immunol. 32(8):2218-2128.

Figure 1D

KD values for Antibody / FcγR interactions:

| Sample | Control-IgG1 | Y12XX-hz28-IgG1-P238K | Antibody B |
|---|---|---|---|
| hCD64 | 0.2 nM | 25 nM | 150 nM |
| hCD32a-H131 | 600 nM | >50 uM | >50 uM |
| hCD32a-R131 | 840 nM | >50 uM | >50 uM |
| hCD32b | 3.9 uM | >50 uM | >50 uM |
| hCD16a-V158 | 270 nM | >50 uM | 7 uM |
| hCD16a-F158 | 11 uM | >50 uM | >50 uM |

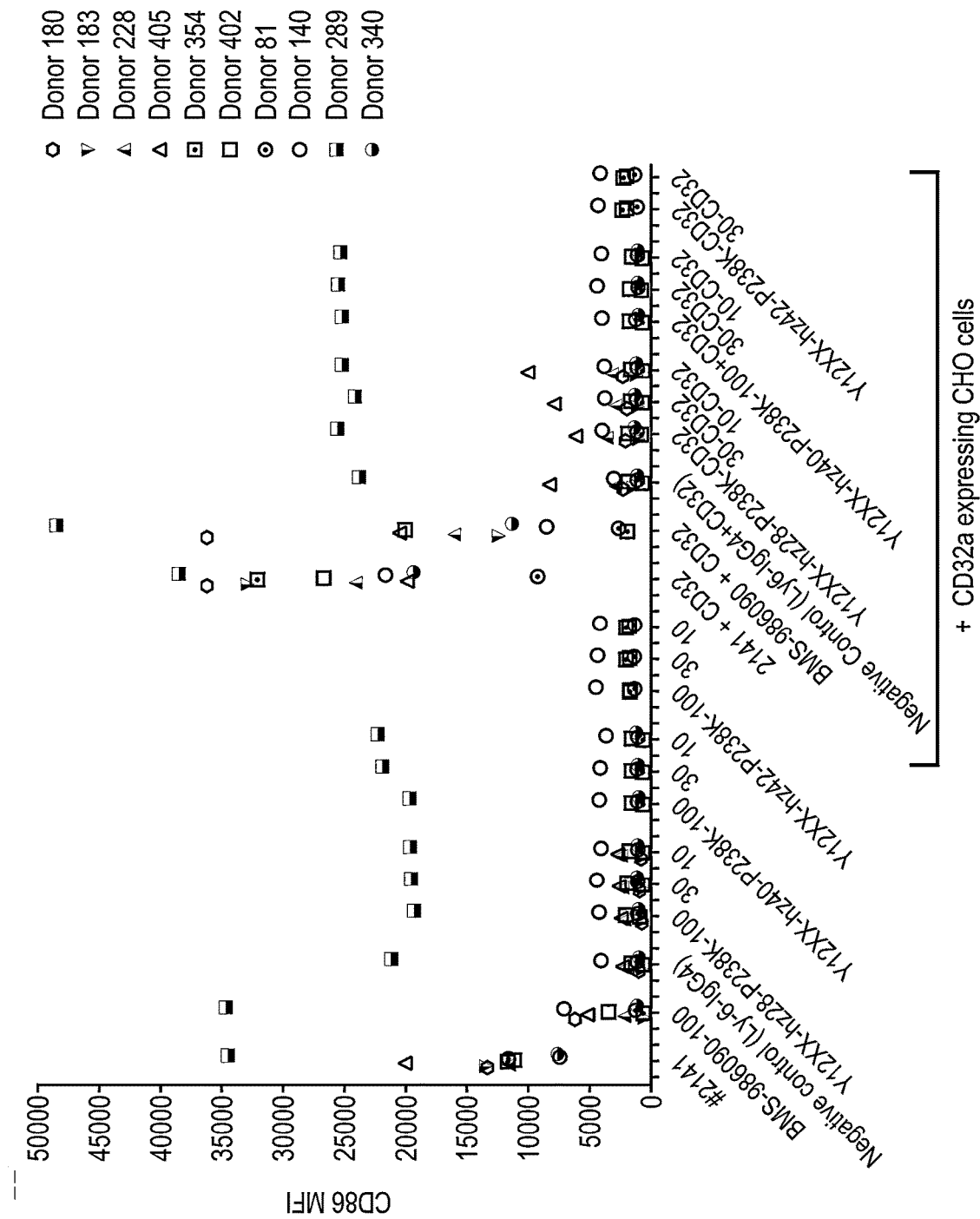

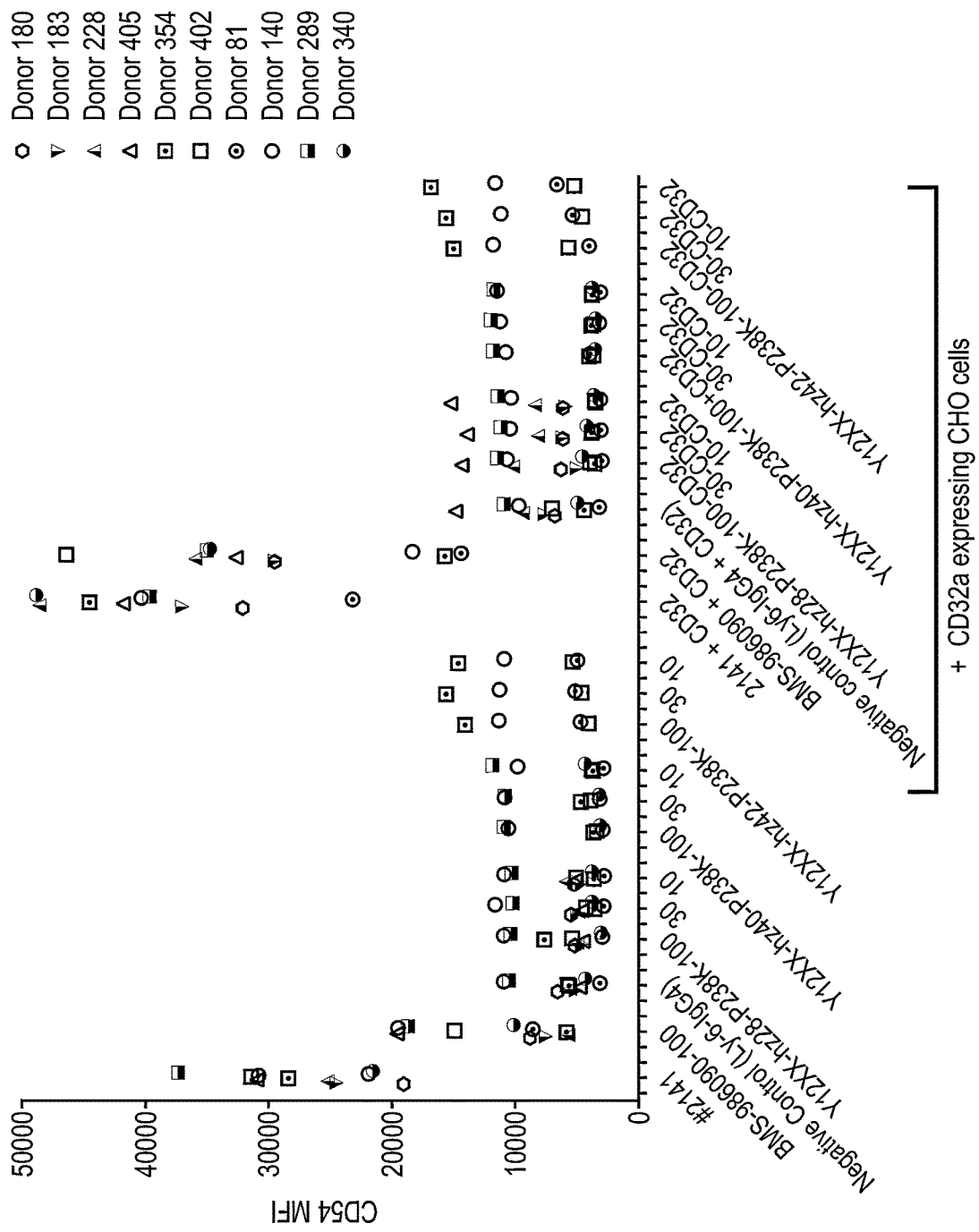

SEQUENCE LISTING

```
Sequence total quantity: 120
SEQ ID NO: 1           moltype = AA  length = 5
FEATURE                Location/Qualifiers
REGION                 1..5
                       note = Synthetic polypeptide: VH-CDR1
source                 1..5
                       mol_type = protein
                       organism = synthetic construct
SEQUENCE: 1
SYWMH                                                                5

SEQ ID NO: 2           moltype = AA  length = 17
FEATURE                Location/Qualifiers
REGION                 1..17
                       note = Synthetic polypeptide: VH-CDR2
source                 1..17
                       mol_type = protein
                       organism = synthetic construct
SEQUENCE: 2
QINPTTGRSQ YNEKFKT                                                  17

SEQ ID NO: 3           moltype = AA  length = 8
FEATURE                Location/Qualifiers
REGION                 1..8
                       note = Synthetic polypeptide: VH-CDR3
source                 1..8
                       mol_type = protein
```

```
                            organism = synthetic construct
SEQUENCE: 3
WGLQPFAY                                                                    8

SEQ ID NO: 4            moltype = AA   length = 117
FEATURE                 Location/Qualifiers
REGION                  1..117
                        note = Synthetic polypeptide: Vh-hz14
source                  1..117
                        mol_type = protein
                        organism = synthetic construct
SEQUENCE: 4
QVQLVQSGAE VKKPGSSVKV SCKASGYAFT SYWMHWVRQA PGQGLEWMGQ INPTTGRSQY     60
NEKFKTRVTI TADKSTSTAY MELSSLRSED TAVYYCARWG LQPFAYWGQG TLVTVSS       117

SEQ ID NO: 5            moltype = AA   length = 446
FEATURE                 Location/Qualifiers
REGION                  1..446
                        note = Synthetic polypeptide: HC_Y12XX-hz28-CH1-IgG1-P238K
                         (is IgG1 without C-terminal lysine)
source                  1..446
                        mol_type = protein
                        organism = synthetic construct
SEQUENCE: 5
QVQLVQSGAE VKKPGSSVKV SCKASGYAFT SYWMHWVRQA PGQGLEWMGQ INPTTGRSQY     60
NEKFKTRVTI TADKSTSTAY MELSSLRSED TAVYYCARWG LQPFAYWGQG TLVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKRVEPKSC DKTHTCPPCP APELLGGKSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSRDELTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPG                                        446

SEQ ID NO: 6            moltype = AA   length = 447
FEATURE                 Location/Qualifiers
REGION                  1..447
                        note = Synthetic polypeptide: HC_Y12XX-hz28-CH1-IgG1-P238K
                         (is IgG1 with C-terminal lysine)
source                  1..447
                        mol_type = protein
                        organism = synthetic construct
SEQUENCE: 6
QVQLVQSGAE VKKPGSSVKV SCKASGYAFT SYWMHWVRQA PGQGLEWMGQ INPTTGRSQY     60
NEKFKTRVTI TADKSTSTAY MELSSLRSED TAVYYCARWG LQPFAYWGQG TLVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKRVEPKSC DKTHTCPPCP APELLGGKSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSRDELTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPGK                                       447

SEQ ID NO: 7            moltype = AA   length = 11
FEATURE                 Location/Qualifiers
REGION                  1..11
                        note = Synthetic polypeptide: VL-CDR1
source                  1..11
                        mol_type = protein
                        organism = synthetic construct
SEQUENCE: 7
KASQDVSTAV A                                                         11

SEQ ID NO: 8            moltype = AA   length = 7
FEATURE                 Location/Qualifiers
REGION                  1..7
                        note = Synthetic polypeptide: VL-CDR2
source                  1..7
                        mol_type = protein
                        organism = synthetic construct
SEQUENCE: 8
SASYRYT                                                               7

SEQ ID NO: 9            moltype = AA   length = 9
FEATURE                 Location/Qualifiers
REGION                  1..9
                        note = Synthetic polypeptide: VL-CDR3
source                  1..9
                        mol_type = protein
                        organism = synthetic construct
SEQUENCE: 9
```

```
QQHYSTPWT                                                                9

SEQ ID NO: 10            moltype = AA  length = 107
FEATURE                  Location/Qualifiers
REGION                   1..107
                         note = Synthetic polypeptide: Vk-hz2
source                   1..107
                         mol_type = protein
                         organism = synthetic construct
SEQUENCE: 10
DIQMTQSPSF LSASVGDRVT ITCKASQDVS TAVAWYQQKP GKAPKLLIYS ASYRYTGVPS    60
RFSGSGSGTD FTLTISSLQP EDFATYYCQQ HYSTPWTFGG GTKVEIK                 107

SEQ ID NO: 11            moltype = AA  length = 214
FEATURE                  Location/Qualifiers
REGION                   1..214
                         note = Synthetic polypeptide: LC_ Y12XX-hz28
source                   1..214
                         mol_type = protein
                         organism = synthetic construct
SEQUENCE: 11
DIQMTQSPSF LSASVGDRVT ITCKASQDVS TAVAWYQQKP GKAPKLLIYS ASYRYTGVPS    60
RFSGSGSGTD FTLTISSLQP EDFATYYCQQ HYSTPWTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 12            moltype = AA  length = 17
FEATURE                  Location/Qualifiers
REGION                   1..17
                         note = Synthetic polypeptide: VH-CDR2 (Vh-hz12)
source                   1..17
                         mol_type = protein
                         organism = synthetic construct
SEQUENCE: 12
QINPSQGRSQ YNEKFKT                                                   17

SEQ ID NO: 13            moltype = AA  length = 117
FEATURE                  Location/Qualifiers
REGION                   1..117
                         note = Synthetic polypeptide: Vh-hz12
source                   1..117
                         mol_type = protein
                         organism = synthetic construct
SEQUENCE: 13
QVQLVQSGAE VKKPGSSVKV SCKASGYAFT SYWMHWVRQA PGQGLEWMGQ INPSQGRSQY    60
NEKFKTRVTI TADKSTSTAY MELSSLRSED TAVYYCARWG LQPFAYWGQG TLVTVSS      117

SEQ ID NO: 14            moltype = AA  length = 446
FEATURE                  Location/Qualifiers
REGION                   1..446
                         note = Synthetic polypeptide: HC_Y12XX-hz40-P238K -IgG1a
                          without C-terminal lysine
source                   1..446
                         mol_type = protein
                         organism = synthetic construct
SEQUENCE: 14
QVQLVQSGAE VKKPGSSVKV SCKASGYAFT SYWMHWVRQA PGQGLEWMGQ INPSQGRSQY    60
NEKFKTRVTI TADKSTSTAY MELSSLRSED TAVYYCARWG LQPFAYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC DKTHTCPPCP APELLGGKSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 15            moltype = AA  length = 447
FEATURE                  Location/Qualifiers
REGION                   1..447
                         note = Synthetic polypeptide: HC_Y12XX-hz40-P238K -IgG1a
                          with C-terminal lysine
source                   1..447
                         mol_type = protein
                         organism = synthetic construct
SEQUENCE: 15
QVQLVQSGAE VKKPGSSVKV SCKASGYAFT SYWMHWVRQA PGQGLEWMGQ INPSQGRSQY    60
NEKFKTRVTI TADKSTSTAY MELSSLRSED TAVYYCARWG LQPFAYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC DKTHTCPPCP APELLGGKSV   240
FLFPPKPKDT LMISRTPEVT CVVVDVSHED PEVKFNWYVD GVEVHNAKTK PREEQYNSTY   300
```

```
RVVSVLTVLH QDWLNGKEYK CKVSNKALPA PIEKTISKAK GQPREPQVYT LPPSRDELTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPGK                                       447

SEQ ID NO: 16            moltype = AA   length = 107
FEATURE                  Location/Qualifiers
REGION                   1..107
                         note = Synthetic polypeptide: Vk-hz3
source                   1..107
                         mol_type = protein
                         organism = synthetic construct
SEQUENCE: 16
EIVMTQSPAT LSVSPGERAT LSCKASQDVS TAVAWYQQKP GQAPRLLIYS ASYRYTGIPA    60
RFSGSGSGTE FTLTISSLQS EDFAVYYCQQ HYSTPWTFGG GTKVEIK                 107

SEQ ID NO: 17            moltype = AA   length = 214
FEATURE                  Location/Qualifiers
REGION                   1..214
                         note = Synthetic polypeptide: LC_ Y12XX-hz40
source                   1..214
                         mol_type = protein
                         organism = synthetic construct
SEQUENCE: 17
EIVMTQSPAT LSVSPGERAT LSCKASQDVS TAVAWYQQKP GQAPRLLIYS ASYRYTGIPA    60
RFSGSGSGTE FTLTISSLQS EDFAVYYCQQ HYSTPWTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 18            moltype = AA   length = 98
FEATURE                  Location/Qualifiers
REGION                   1..98
                         note = Synthetic polypeptide: heavy chain CH1=amino acids
                          118-215 of SEQ ID NO: 5
source                   1..98
                         mol_type = protein
                         organism = synthetic construct
SEQUENCE: 18
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRV                            98

SEQ ID NO: 19            moltype = AA   length = 107
FEATURE                  Location/Qualifiers
REGION                   1..107
                         note = Synthetic polypeptide: light chain CL = amino acids
                          108-214 of SEQ ID NO: 11
source                   1..107
                         mol_type = protein
                         organism = synthetic construct
SEQUENCE: 19
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 20            moltype = AA   length = 277
FEATURE                  Location/Qualifiers
source                   1..277
                         mol_type = protein
                         organism = Homo sapiens
SEQUENCE: 20
MVRLPLQCVL WGCLLTAVHP EPPTACREKQ YLINSQCCSL CQPGQKLVSD CTEFTETECL    60
PCGESEFLDT WNRETHCHQH KYCDPNLGLR VQQKGTSETD TICTCEEGWH CTSEACESCV   120
LHRSCSPGFG VKQIATGVSD TICEPCPVGF FSNVSSAFEK CHPWTSCETK DLVVQQAGTN   180
KTDVVCGPQD RLRALVVIPI IFGILFAILL VLVFIKKVAK KPTNKAPHPK QEPQEINFPD   240
DLPGSNTAAP VQETLHGCQP VTQEDGKESR ISVQERQ                            277

SEQ ID NO: 21            moltype = AA   length = 232
FEATURE                  Location/Qualifiers
REGION                   1..232
                         note = Synthetic polypeptide: Fc consensus
VARIANT                  23
                         note = P or K
VARIANT                  82
                         note = N or A
VARIANT                  141
                         note = D or E
VARIANT                  143
                         note = L or M
VARIANT                  232
                         note = K or residue is absent
source                   1..232
```

```
                        mol_type = protein
                        organism = synthetic construct
SEQUENCE: 21
EPKSCDKTHT CPPCPAPELL GGXSVFLFPP KPKDTLMISR TPEVTCVVVD VSHEDPEVKF  60
NWYVDGVEVH NAKTKPREEQ YXSTYRVVSV LTVLHQDWLN GKEYKCKVSN KALPAPIEKT 120
ISKAKGQPRE PQVYTLPPSR XEXTKNQVSL TCLVKGFYPS DIAVEWESNG QPENNYKTTP 180
PVLDSDGSFF LYSKLTVDKS RWQQGNVFSC SVMHEALHNH YTQKSLSLSP GX         232

SEQ ID NO: 22           moltype = AA  length = 231
FEATURE                 Location/Qualifiers
REGION                  1..231
                        note = Synthetic polypeptide: IgG1-P238K(-C-term Lys)
source                  1..231
                        mol_type = protein
                        organism = synthetic construct
SEQUENCE: 22
EPKSCDKTHT CPPCPAPELL GGKSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT 120
ISKAKGQPRE PQVYTLPPSR DELTKNQVSL TCLVKGFYPS DIAVEWESNG QPENNYKTTP 180
PVLDSDGSFF LYSKLTVDKS RWQQGNVFSC SVMHEALHNH YTQKSLSLSP G          231

SEQ ID NO: 23           moltype = AA  length = 232
FEATURE                 Location/Qualifiers
REGION                  1..232
                        note = Synthetic polypeptide: IgG1-P238K
source                  1..232
                        mol_type = protein
                        organism = synthetic construct
SEQUENCE: 23
EPKSCDKTHT CPPCPAPELL GGKSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT 120
ISKAKGQPRE PQVYTLPPSR DELTKNQVSL TCLVKGFYPS DIAVEWESNG QPENNYKTTP 180
PVLDSDGSFF LYSKLTVDKS RWQQGNVFSC SVMHEALHNH YTQKSLSLSP GK         232

SEQ ID NO: 24           moltype = AA  length = 329
FEATURE                 Location/Qualifiers
REGION                  1..329
                        note = Synthetic polypeptide: CH1-IgG1-P238K(-C-term Lys)
source                  1..329
                        mol_type = protein
                        organism = synthetic construct
SEQUENCE: 24
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG 120
KSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LPAPIEKTIS KAKGQPREPQ VYTLPPSRDE 240
LTKNQVSLTC LVKGFYPSDI AVEWESNGQP ENNYKTTPPV LDSDGSFFLY SKLTVDKSRW 300
QQGNVFSCSV MHEALHNHYT QKSLSLSPG                                   329

SEQ ID NO: 25           moltype = AA  length = 330
FEATURE                 Location/Qualifiers
REGION                  1..330
                        note = Synthetic polypeptide: CH1-IgG1-P238K
source                  1..330
                        mol_type = protein
                        organism = synthetic construct
SEQUENCE: 25
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG 120
KSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LPAPIEKTIS KAKGQPREPQ VYTLPPSRDE 240
LTKNQVSLTC LVKGFYPSDI AVEWESNGQP ENNYKTTPPV LDSDGSFFLY SKLTVDKSRW 300
QQGNVFSCSV MHEALHNHYT QKSLSLSPGK                                  330

SEQ ID NO: 26           moltype = AA  length = 231
FEATURE                 Location/Qualifiers
REGION                  1..231
                        note = Synthetic polypeptide: IgG1f-P238K(-C-term Lys)
source                  1..231
                        mol_type = protein
                        organism = synthetic construct
SEQUENCE: 26
EPKSCDKTHT CPPCPAPELL GGKSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT 120
ISKAKGQPRE PQVYTLPPSR EEMTKNQVSL TCLVKGFYPS DIAVEWESNG QPENNYKTTP 180
PVLDSDGSFF LYSKLTVDKS RWQQGNVFSC SVMHEALHNH YTQKSLSLSP G          231

SEQ ID NO: 27           moltype = AA  length = 232
FEATURE                 Location/Qualifiers
```

```
REGION                          1..232
                                note = Synthetic polypeptide: IgG1f-P238K
source                          1..232
                                mol_type = protein
                                organism = synthetic construct
SEQUENCE: 27
EPKSCDKTHT CPPCPAPELL GGKSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR EEMTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 28                   moltype = AA  length = 329
FEATURE                         Location/Qualifiers
REGION                          1..329
                                note = Synthetic polypeptide: CH1-IgG1f-P238K(-C-term Lys)
source                          1..329
                                mol_type = protein
                                organism = synthetic construct
SEQUENCE: 28
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
KSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 29                   moltype = AA  length = 330
FEATURE                         Location/Qualifiers
REGION                          1..330
                                note = Synthetic polypeptide: CH1-IgG1f-P238K
source                          1..330
                                mol_type = protein
                                organism = synthetic construct
SEQUENCE: 29
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
KSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 30                   moltype = AA  length = 446
FEATURE                         Location/Qualifiers
REGION                          1..446
                                note = Synthetic polypeptide:
                                HC_Y12XX-hz28-CH1-IgG1f-P238K- no terminal lysine)
source                          1..446
                                mol_type = protein
                                organism = synthetic construct
SEQUENCE: 30
QVQLVQSGAE VKKPGSSVKV SCKASGYAFT SYWMHWVRQA PGQGLEWMGQ INPTTGRSQY    60
NEKFKTRVTI TADKSTSTAY MELSSLRSED TAVYYCARWG LQPFAYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC DKTHTCPPCP APELLGGKSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                       446

SEQ ID NO: 31                   moltype = AA  length = 447
FEATURE                         Location/Qualifiers
REGION                          1..447
                                note = Synthetic polypeptide:
                                HC_Y12XX-hz28-CH1-IgG1f-P238K- with terminal lysine)
source                          1..447
                                mol_type = protein
                                organism = synthetic construct
SEQUENCE: 31
QVQLVQSGAE VKKPGSSVKV SCKASGYAFT SYWMHWVRQA PGQGLEWMGQ INPTTGRSQY    60
NEKFKTRVTI TADKSTSTAY MELSSLRSED TAVYYCARWG LQPFAYWGQG TLVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC DKTHTCPPCP APELLGGKSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPSREEMTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPGK                                      447

SEQ ID NO: 32                   moltype = AA  length = 231
FEATURE                         Location/Qualifiers
```

| | | |
|---|---|---|
| REGION | 1..231<br>note = Synthetic polypeptide: IgG1-N297A(-C-term Lys) | |
| source | 1..231<br>mol_type = protein<br>organism = synthetic construct | |

SEQUENCE: 32

```
EPKSCDKTHT CPPCPAPELL GGPSVFLFPP KPKDTLMISR TPEVTCVVVD VSHEDPEVKF   60
NWYVDGVEVH NAKTKPREEQ YASTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP G          231
```

| | | |
|---|---|---|
| SEQ ID NO: 33 | moltype = AA   length = 232 | |
| FEATURE | Location/Qualifiers | |
| REGION | 1..232<br>note = Synthetic polypeptide: IgG1-N297A | |
| source | 1..232<br>mol_type = protein<br>organism = synthetic construct | |

SEQUENCE: 33

```
EPKSCDKTHT CPPCPAPELL GGPSVFLFPP KPKDTLMISR TPEVTCVVVD VSHEDPEVKF   60
NWYVDGVEVH NAKTKPREEQ YASTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GK         232
```

| | | |
|---|---|---|
| SEQ ID NO: 34 | moltype = AA   length = 329 | |
| FEATURE | Location/Qualifiers | |
| REGION | 1..329<br>note = Synthetic polypeptide: CH1-IgG1-N297A(-C-term Lys) | |
| source | 1..329<br>mol_type = protein<br>organism = synthetic construct | |

SEQUENCE: 34

```
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329
```

| | | |
|---|---|---|
| SEQ ID NO: 35 | moltype = AA   length = 330 | |
| FEATURE | Location/Qualifiers | |
| REGION | 1..330<br>note = Synthetic polypeptide: CH1-IgG1-N297A | |
| source | 1..330<br>mol_type = protein<br>organism = synthetic construct | |

SEQUENCE: 35

```
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330
```

| | | |
|---|---|---|
| SEQ ID NO: 36 | moltype = AA   length = 231 | |
| FEATURE | Location/Qualifiers | |
| REGION | 1..231<br>note = Synthetic polypeptide: IgG1f-N297A(-C-term Lys) | |
| source | 1..231<br>mol_type = protein<br>organism = synthetic construct | |

SEQUENCE: 36

```
EPKSCDKTHT CPPCPAPELL GGPSVFLFPP KPKDTLMISR TPEVTCVVVD VSHEDPEVKF   60
NWYVDGVEVH NAKTKPREEQ YASTYRVVSV LTVLHQDWLN GKEYKCKVSN KALPAPIEKT  120
ISKAKGQPRE PQVYTLPPSR EEMTKNQVSL TCLVKGFYPS DIAVEWESNG QPENNYKTTP  180
PVLDSDGSFF LYSKLTVDKS RWQQGNVFSC SVMHEALHNH YTQKSLSLSP G          231
```

| | | |
|---|---|---|
| SEQ ID NO: 37 | moltype = AA   length = 232 | |
| FEATURE | Location/Qualifiers | |
| REGION | 1..232<br>note = Synthetic polypeptide: IgG1f-N297A | |
| source | 1..232<br>mol_type = protein<br>organism = synthetic construct | |

SEQUENCE: 37

```
EPKSCDKTHT CPPCPAPELL GGPSVFLFPP KPKDTLMISR TPEVTCVVVD VSHEDPEVKF   60
NWYVDGVEVH NAKTKPREEQ YASTYRVVSV LTVLHQDWLN GKEYKCKVSN KALPAPIEKT  120
ISKAKGQPRE PQVYTLPPSR EEMTKNQVSL TCLVKGFYPS DIAVEWESNG QPENNYKTTP  180
PVLDSDGSFF LYSKLTVDKS RWQQGNVFSC SVMHEALHNH YTQKSLSLSP GK         232
```

```
SEQ ID NO: 38            moltype = AA   length = 329
FEATURE                  Location/Qualifiers
REGION                   1..329
                         note = Synthetic polypeptide: CH1-IgG1f-N297A(-C-term Lys)
source                   1..329
                         mol_type = protein
                         organism = synthetic construct
SEQUENCE: 38
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 39            moltype = AA   length = 330
FEATURE                  Location/Qualifiers
REGION                   1..330
                         note = Synthetic polypeptide: CH1-IgG1f-N297A
source                   1..330
                         mol_type = protein
                         organism = synthetic construct
SEQUENCE: 39
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 40            moltype = AA   length = 5
FEATURE                  Location/Qualifiers
REGION                   1..5
                         note = Synthetic polypeptide: Linker
source                   1..5
                         mol_type = protein
                         organism = synthetic construct
SEQUENCE: 40
GGGGS                                                                5

SEQ ID NO: 41            moltype = AA   length = 10
FEATURE                  Location/Qualifiers
REGION                   1..10
                         note = Synthetic polypeptide: Linker
source                   1..10
                         mol_type = protein
                         organism = synthetic construct
SEQUENCE: 41
GGGGSGGGGS                                                          10

SEQ ID NO: 42            moltype = AA   length = 15
FEATURE                  Location/Qualifiers
REGION                   1..15
                         note = Synthetic polypeptide: Linker
source                   1..15
                         mol_type = protein
                         organism = synthetic construct
SEQUENCE: 42
GGGGSGGGGS GGGGS                                                    15

SEQ ID NO: 43            moltype = AA   length = 20
FEATURE                  Location/Qualifiers
REGION                   1..20
                         note = Synthetic polypeptide: Linker
source                   1..20
                         mol_type = protein
                         organism = synthetic construct
SEQUENCE: 43
GGGGSGGGGS GGGGSGGGGS                                               20

SEQ ID NO: 44            moltype = AA   length = 25
FEATURE                  Location/Qualifiers
REGION                   1..25
                         note = Synthetic polypeptide: Linker
source                   1..25
                         mol_type = protein
                         organism = synthetic construct
SEQUENCE: 44
```

```
GGGGSGGGGS GGGGSGGGGS GGGGS                                       25

SEQ ID NO: 45           moltype =    length =
SEQUENCE: 45
000

SEQ ID NO: 46           moltype = AA   length = 6
FEATURE                 Location/Qualifiers
REGION                  1..6
                        note = Synthetic polypeptide: Linker
source                  1..6
                        mol_type = protein
                        organism = synthetic construct
SEQUENCE: 46
TVAAPS                                                            6

SEQ ID NO: 47           moltype =    length =
SEQUENCE: 47
000

SEQ ID NO: 48           moltype = AA   length = 7
FEATURE                 Location/Qualifiers
REGION                  1..7
                        note = Synthetic polypeptide: Linker
source                  1..7
                        mol_type = protein
                        organism = synthetic construct
SEQUENCE: 48
ASTSGPS                                                           7

SEQ ID NO: 49           moltype = DNA   length = 1392
FEATURE                 Location/Qualifiers
misc_feature            1..1392
                        note = Synthetic polypeptide: representative nucleic acid
                          sequence encoding the Y12XX heavy chain variable domain of
                          Y12XX-hz28 including a constant region CH1 and Fc domain
                          IgG1-P238K
source                  1..1392
                        mol_type = other DNA
                        organism = synthetic construct
SEQUENCE: 49
atgagggctt ggatcttctt tctgctctgc ctggccggga gagcgctcgc acaggtgcag   60
ctggtgcagt ctggtgccga ggtcaaaaag ccaggctcca gcgtgaaggt gagctgcaag  120
gcctctggct acgctttcac ctcttattgg atgcactggg tgagacaggc tcctggacag  180
ggcctggagt ggatgggcca gatcaaccca accaccggca gaagccagta caatgagaag  240
tttaagaccc gcgtgaccat cacagccgac aagtccacca gcacagctta tatggagctg  300
tcttccctga ggtccgagga tacagccgtg tactattgcg ctcggtgggg cctgcagcct  360
ttcgcttact ggggccaggg caccctggtg acagtgagct ctgctagcac caagggccca  420
tcggtcttcc ccctggcacc ctcctccaag agcacctctg gggcacagc ggccctgggc  480
tgcctggtca aggactactt ccccgaaccg gtgacggtgt cgtggaactc aggcgccctg  540
accagcggcg tgcacacctt cccggccgtc ctacagtcct caggactcta ctccctcagc  600
agcgtggtga ccgtgccctc cagcagcttg gcacccaga cctacatctg caacgtgaat  660
cacaagccca gcaacaccaa ggtggacaag agagttgagc ccaaatcttg tgacaaaact  720
cacacatgcc caccgtgccc agcacctgaa ctcctggggg gaaagtcagt cttcctcttc  780
cccccaaaac ccaaggacac cctcatgatc tcccggaccc ctgaggtcac atgcgtggtg  840
gtggacgtga gccacgaaga ccctgaggtc aagttcaact ggtacgtgga cggcgtggag  900
gtgcataatg ccaagacaaa gccgcgggag gagcagtaca acagcacgta ccgtgtggtc  960
agcgtcctca ccgtcctgca ccaggactgg ctgaatggca aggagtacaa gtgcaaggtc 1020
tccaacaaag ccctcccagc ccccatcgag aaaaccatct ccaaagccaa agggcagccc 1080
cgagaaccac aggtgtacac cctgccccca tcccgggatg agctgaccaa gaaccaggtc 1140
agcctgacct gcctggtcaa aggcttctat cccagcgaca tcgccgtgga gtgggagagc 1200
aatgggcagc cggagaacaa ctacaagacc acgcctcccg tgctggactc cgacggctcc 1260
ttcttcctct acagcaagct caccgtggac aagagcaggt ggcagcaggg gaacgtcttc 1320
tcatgctccg tgatgcatga ggctctgcac aaccactaca cgcagaagag cctctccctg 1380
tctccgggtt ga                                                    1392

SEQ ID NO: 50           moltype = DNA   length = 696
FEATURE                 Location/Qualifiers
misc_feature            1..696
                        note = Synthetic polypeptide: representative nucleic acid
                          sequence encoding the Y12XX light chain variable domain of
                          Y12XX-hz28 including a constant region CL
source                  1..696
                        mol_type = other DNA
                        organism = synthetic construct
SEQUENCE: 50
atgagggctt ggatcttctt tctgctctgc ctggccgggc gcgccttggc cgacatccag   60
atgacccagt ccccctcctt cctgtctgcc tccgtgggcg acagagtgac catcacctgt  120
aaggcttcc aggatgtgag cacagccgtg gcttggtacc agcagaagcc aggcaaggcc  180
```

```
cccaagctgc tgatctattc cgcctcttac aggtataccg gcgtgccctc tcggttctcc  240
ggcagcggct ctggcacaga ctttacccctg acaatctcca gcctgcagcc tgaggatttc  300
gccacctact attgccagca gcactactcc accccatgga catttggcgg cggcaccaag  360
gtggagatca agcgtacggt ggctgcacca tctgtcttca tcttcccgcc atctgatgag  420
cagttgaaat ctggaactgc ctctgttgtg tgcctgctga ataacttcta tcccagagag  480
gccaaagtac agtggaaggt ggataacgcc ctccaatcgg gtaactccca ggagagtgtc  540
acagagcagg acagcaagga cagcacctac agcctcagca gcaccctgac gctgagcaaa  600
gcagactacg agaaacacaa agtctacgcc tgcgaagtca cccatcaggg cctgagctcg  660
cccgtcacaa agagcttcaa caggggagag tgttag                           696

SEQ ID NO: 51          moltype = AA   length = 17
FEATURE                Location/Qualifiers
REGION                 1..17
                       note = Synthetic polypeptide: signal peptide
source                 1..17
                       mol_type = protein
                       organism = synthetic construct
SEQUENCE: 51
MRAWIFFLLC LAGRALA                                                17

SEQ ID NO: 52          moltype = DNA   length = 51
FEATURE                Location/Qualifiers
misc_feature           1..51
                       note = Synthetic polypeptide: coding sequence for signal
                        peptide
source                 1..51
                       mol_type = other DNA
                       organism = synthetic construct
SEQUENCE: 52
atgagggctt ggatcttctt tctgctctgc ctggccggga gagcgctcgc a          51

SEQ ID NO: 53          moltype = AA   length = 126
FEATURE                Location/Qualifiers
REGION                 1..126
                       note = Synthetic polypeptide: ADX_Y1060.ZZ0-1-Vh
source                 1..126
                       mol_type = protein
                       organism = synthetic construct
SEQUENCE: 53
QVQLVQSGAE VKKPGASVKV SCKASGYTFT GYYMHWVRQA PGQGLEWMGW INPDSGGTNY  60
AQKFQGRVTM TRDTSISTAY MELNRLRSDD TAVYYCARDQ PLGYCTNGVC SYFDYWGQGT  120
LVTVSS                                                            126

SEQ ID NO: 54          moltype = AA   length = 122
FEATURE                Location/Qualifiers
REGION                 1..122
                       note = Synthetic polypeptide: ADX_Y1072.ZZ0-1-Vh
source                 1..122
                       mol_type = protein
                       organism = synthetic construct
SEQUENCE: 54
QVQFQQSGAE LARPGASVKL SCKASGYTFT SYWMQWVKQR PGQGLEWIGT IYPGDGDSRY  60
NQKFKGKALL TADKSSSIAY MQLNSLASED SAVYFCARFS LYDGYPYYFD YWGQGTTLTV  120
SS                                                                122

SEQ ID NO: 55          moltype = AA   length = 118
FEATURE                Location/Qualifiers
REGION                 1..118
                       note = Synthetic polypeptide: ADX_Y1234.ZZ0-1-Vh
source                 1..118
                       mol_type = protein
                       organism = synthetic construct
SEQUENCE: 55
EVQLVESGGG LVKPGGSLKL SCAASGFAFS SYDMSWVRQT PEKRLEWVAY INSGVGNTYY  60
PDTVKGRFTI SRDNAKNTLY LQMSSLKSED TAMYYCARHG NYAWFAYWGQ GTLVTVSA   118

SEQ ID NO: 56          moltype = AA   length = 117
FEATURE                Location/Qualifiers
REGION                 1..117
                       note = Synthetic polypeptide: ADX_Y1236.ZZ0-1-Vh
source                 1..117
                       mol_type = protein
                       organism = synthetic construct
SEQUENCE: 56
DVQLVESGGG LVQPGGSRKL SCAASGFTFS SFGMHWVRQA PEKGLEWVAY ISSGSSTIYY  60
ADTVKGRFTI SRDNPKNTLF LQMTSLRSED TAMYYCARYG NYAMDYWGQG TSVTVSS    117

SEQ ID NO: 57          moltype = AA   length = 118
FEATURE                Location/Qualifiers
```

```
REGION                  1..118
                        note = Synthetic polypeptide: ADX_Y1238.ZZ0-1-Vh
source                  1..118
                        mol_type = protein
                        organism = synthetic construct
SEQUENCE: 57
QVQLQQSGAE LVRPGTSVKV SCKASGYAFT NYLIEWVKQR PGQGLEWIGV INPGSGGTNY   60
NEKFKGKATL TADKSSSTAY MQLSSLTSDD SAVYFCARSQ LGRRFDYWGQ GTTLTVSS    118

SEQ ID NO: 58           moltype = AA  length = 115
FEATURE                 Location/Qualifiers
REGION                  1..115
                        note = Synthetic polypeptide: ADX_Y1241.ZZ0-1-Vh
source                  1..115
                        mol_type = protein
                        organism = synthetic construct
SEQUENCE: 58
EFQLQQSGPE LVKPGASVKM SCKASGYTFT NYIIQWVKKQ PGQGLEWIGY INPYSSETNY   60
NEKFKGKATL TSDKSSSTAY MELSSLTSED SAIYFCARDL IGNYWGQGTT LTVSS       115

SEQ ID NO: 59           moltype = AA  length = 117
FEATURE                 Location/Qualifiers
REGION                  1..117
                        note = Synthetic polypeptide: ADX_Y1242.ZZ0-1-Vh
source                  1..117
                        mol_type = protein
                        organism = synthetic construct
SEQUENCE: 59
EFQLQQSGPE LVKPGASVKM SCKASGYSFT SYVMHWVKQK PGQALEWIGY INPSNDGSEY   60
NERFKGKATL TSDKSSTTAY MELSSLTSED SAVYYCARWA PYPFAYWGQG TLVTVSA     117

SEQ ID NO: 60           moltype = AA  length = 120
FEATURE                 Location/Qualifiers
REGION                  1..120
                        note = Synthetic polypeptide: ADX_Y1249.ZZ0-1-Vh
source                  1..120
                        mol_type = protein
                        organism = synthetic construct
SEQUENCE: 60
QVQLQQSGAE LARPGASVKM SCKASGYTFT SYTMHWVKQR PGQGLEWIGY IDPSSHYTNY   60
NQKFKGTATL TADKSSNTAY MQLSSLTSED SAVYYCARDY RYAYWYFDVW GAGTTLTVSS  120

SEQ ID NO: 61           moltype = AA  length = 117
FEATURE                 Location/Qualifiers
REGION                  1..117
                        note = Synthetic polypeptide: ADX_Y1256.ZZ0-1-Vh
source                  1..117
                        mol_type = protein
                        organism = synthetic construct
SEQUENCE: 61
QVQLQQSGAE LAKPGSSVKM SCKASGYAFT SYWMHWVKQR PGQGLEWIGY INPTTGYSAY   60
NQKFKDKATL TADKSSSTAY LQLTSLTSED SAVYFCSRWG LPPFAYWGQG TLVTVSA     117

SEQ ID NO: 62           moltype = AA  length = 117
FEATURE                 Location/Qualifiers
REGION                  1..117
                        note = Synthetic polypeptide: ADX_Y1257.ZZ0-1-Vh
source                  1..117
                        mol_type = protein
                        organism = synthetic construct
SEQUENCE: 62
QVQLQQSGAE LAKPGSSVKM SCKASGYAFT SYWMHWVKQR PGQGLEWIGY INPTTGYSAY   60
NQKFKAKTTL TADKSSSTAY MQLTSLTFED SAVYFCSRWG LPPFAYWGQG TLVTVSA     117

SEQ ID NO: 63           moltype = AA  length = 117
FEATURE                 Location/Qualifiers
REGION                  1..117
                        note = Synthetic polypeptide: ADX_Y1258.ZZ0-1-Vh
source                  1..117
                        mol_type = protein
                        organism = synthetic construct
SEQUENCE: 63
QVQLQQSGAE LAKPGSSVKM SCKASGYAFT SYWMHWIKQR PGQGLEWIGF INPTTGYSEY   60
NQKFKDKATL TADKSSSTAY MQLNSLTSED SAVYFCARWG LPPFAYWGQG TLVTVSA     117

SEQ ID NO: 64           moltype = AA  length = 117
FEATURE                 Location/Qualifiers
REGION                  1..117
                        note = Synthetic polypeptide: ADX_Y1259.ZZ0-1-Vh
```

```
source                  1..117
                        mol_type = protein
                        organism = synthetic construct
SEQUENCE: 64
QVQLQQSGAE LAKPGASVKM SCKTSGYSFT SYWMHWIKQR PGQGLEWIGF INPTTGYTEY    60
NQKFKDKATL TADKSSSTAY MQLSSLSSED SAVYYCSRWG LPPFAYWGQG TLVTVSA     117

SEQ ID NO: 65           moltype = AA  length = 117
FEATURE                 Location/Qualifiers
REGION                  1..117
                        note = Synthetic polypeptide: ADX_Y1260.ZZ0-1-Vh
source                  1..117
                        mol_type = protein
                        organism = synthetic construct
SEQUENCE: 65
QVQLQQSGAE LTKPGASVKM SCKASGYSFT SYWMHWVKQR PGQGLEWIGS INPSTGYTED    60
NQKFKDKATL TADKSSTTAY MQLSSLTSED SAVYYCARWG LPPFAYWGQG TLVTVSA     117

SEQ ID NO: 66           moltype = AA  length = 117
FEATURE                 Location/Qualifiers
REGION                  1..117
                        note = Synthetic polypeptide: ADX_Y1261.ZZ0-1-Vh
source                  1..117
                        mol_type = protein
                        organism = synthetic construct
SEQUENCE: 66
QVQLQQSGAE RAKPGASVKM SCKASGYSFT SYWMHWIKQR PGQGLEWIGF INPNTGHTDY    60
NQKFKDKATL TADKSSSTAY MQLSSLTSED SAVYFCSRWG LPPFAYWGQG TLVTVSA     117

SEQ ID NO: 67           moltype = AA  length = 117
FEATURE                 Location/Qualifiers
REGION                  1..117
                        note = Synthetic polypeptide: ADX_Y1262.ZZ0-1-Vh
source                  1..117
                        mol_type = protein
                        organism = synthetic construct
SEQUENCE: 67
QVQLQQSGAE LAKPGSSVKM SCKASGYAFT SYWMHWVKQR PGQGLEWIGY INPTTGYSAY    60
NQKFKDKATL TADKSSSTAY MQLNSLTSED SAVYYCARWD PRPFAYWGQG TLVTVSA     117

SEQ ID NO: 68           moltype = AA  length = 117
FEATURE                 Location/Qualifiers
REGION                  1..117
                        note = Synthetic polypeptide: ADX_Y1263.ZZ0-1-Vh
source                  1..117
                        mol_type = protein
                        organism = synthetic construct
SEQUENCE: 68
QVQLQQSGAE LAKPGTSVKM SCKASGYSFT SYWVHWVKER PGQGLEWIGH TNPNTGYTEY    60
NQKFKDKATL TVDRSSSTAY MQLNSLTSED SAVYYCARWD PRPFAYWGQG TLVTVSA     117

SEQ ID NO: 69           moltype = AA  length = 117
FEATURE                 Location/Qualifiers
REGION                  1..117
                        note = Synthetic polypeptide: ADX_Y1264.ZZ0-1-Vh
source                  1..117
                        mol_type = protein
                        organism = synthetic construct
SEQUENCE: 69
EVQLQQSGTV LARPGASVKM SCRASGYSFS SYWMHWVKQR PGQGLEWIGS INPGNSDAFY    60
NQQFKGKAKL TAVTSASTAY MELSSLTNED SAVYYCTRWG LPPFAYWGQG TLVTVSA     117

SEQ ID NO: 70           moltype = AA  length = 117
FEATURE                 Location/Qualifiers
REGION                  1..117
                        note = Synthetic polypeptide: ADX_Y1265.ZZ0-1-Vh
source                  1..117
                        mol_type = protein
                        organism = synthetic construct
SEQUENCE: 70
EVQLQQSGTV LAGPGASVKM SCKASGYSFT SYWMHWVKQR PGQDLEWIGT INPGKGDSNY    60
NQKFKGKAKL TAVTSASTAY MELSSLTNED SAVYYCTRWG LPPFAYWGQG TLVTVSA     117

SEQ ID NO: 71           moltype = AA  length = 117
FEATURE                 Location/Qualifiers
REGION                  1..117
                        note = Synthetic polypeptide: ADX_Y1266.ZZ0-1-Vh
source                  1..117
                        mol_type = protein
```

```
                        organism = synthetic construct
SEQUENCE: 71
QVQLQQPGAE LVKPGASVRL SCKASGYSFT SYWMHWVKQR PGQGLEWIGQ INPSNGRTQY    60
NEKFKSMATL TVDKSSSTAY IQLSSLTSED SAVYYCARWG LQPFAYWGQG TLVTVSA      117

SEQ ID NO: 72           moltype = AA   length = 117
FEATURE                 Location/Qualifiers
REGION                  1..117
                        note = Synthetic polypeptide: ADX_Y1267.ZZ0-1-Vh
source                  1..117
                        mol_type = protein
                        organism = synthetic construct
SEQUENCE: 72
QVQLQQPGAE LVKPGASVRL SCEASGYSFT SYWMHWVKQR PGQGLEWIGQ INPSNGRTQY    60
NEKFKSMATL TVDKSSSTAY IQLNSLTSED SAVYYCARWG LQPFAYWGQG TLVTVSA      117

SEQ ID NO: 73           moltype = AA   length = 117
FEATURE                 Location/Qualifiers
REGION                  1..117
                        note = Synthetic polypeptide: ADX_Y1268.ZZ0-1-Vh
source                  1..117
                        mol_type = protein
                        organism = synthetic construct
SEQUENCE: 73
QVQLQQPGAE LVKPGASVRL SCKASGYAFT SYWMHWVKQR PGQGLEWIGQ INPSNGRSQY    60
NEKFKTMATL TVDKSSSTAY IQLSSLTSED SAVYYCARWG LQPFAYWGQG TLVTVSA      117

SEQ ID NO: 74           moltype = AA   length = 118
FEATURE                 Location/Qualifiers
REGION                  1..118
                        note = Synthetic polypeptide: ADX_Y1269.ZZ0-1-Vh
source                  1..118
                        mol_type = protein
                        organism = synthetic construct
SEQUENCE: 74
QVQLQQSGAE LPRPGASVKM SCKASGYTFT DYTVHWVKQR PGQGLEWIGY INPSSSYTSY    60
DQKFKDKATV TADKSSSTAY MQLSSLTSED SAVYYCARRT MYWYFDIWGA GTTVTVSS     118

SEQ ID NO: 75           moltype = AA   length = 120
FEATURE                 Location/Qualifiers
REGION                  1..120
                        note = Synthetic polypeptide: ADX_Y1297.ZZ0-1-Vh
source                  1..120
                        mol_type = protein
                        organism = synthetic construct
SEQUENCE: 75
QVQLQQSGAE LVKPGASVKL SCKASGYTFT SYWMHWVKQR PGQGLEWIGE IDPSDSYTNY    60
NQNFKGKATL TVDKSSSTAY MQLSSLTSED SAVYYCARET YYYGSRFPYW GQGTLVTVSA   120

SEQ ID NO: 76           moltype = AA   length = 107
FEATURE                 Location/Qualifiers
REGION                  1..107
                        note = Synthetic polypeptide: ADX_Y1060.ZZ0-1-Vk
source                  1..107
                        mol_type = protein
                        organism = synthetic construct
SEQUENCE: 76
DIQMTQSPSS VSASVGDRVT ITCRASQGIY SWLAWYQQKP GKAPNLLIYT ASTLQSGVPS    60
RFSGSGSGTD FTLTISSLQP EDFATYYCQQ ANIFPLTFGG GTKVEIK                 107

SEQ ID NO: 77           moltype = AA   length = 112
FEATURE                 Location/Qualifiers
REGION                  1..112
                        note = Synthetic polypeptide: ADX_Y1072.ZZ0-1-Vk
source                  1..112
                        mol_type = protein
                        organism = synthetic construct
SEQUENCE: 77
DVVMTQTPLS LPVSLGDQAS ISCRSSQSLV HRNGNTYLHW YLQKPGQSPK LLIYRVSNRF    60
SGVPDRFSGS GSGTDFTLKI SRVEAEDLGI YFCSQSTHFP YTFGGGTKLE IK           112

SEQ ID NO: 78           moltype = AA   length = 107
FEATURE                 Location/Qualifiers
REGION                  1..107
                        note = Synthetic polypeptide: ADX_Y1234.ZZ0-1-Vk
source                  1..107
                        mol_type = protein
                        organism = synthetic construct
SEQUENCE: 78
```

```
DILLTQSPAI LSVSPGERVS FSCRASQSIG TSIHWYQQRT IGSPRLLIKY ASESISGIPS    60
RFSGSGSGTD FTLSINSVES EDIADYYCQQ INSWPLTFGA GTKLELK                107

SEQ ID NO: 79           moltype = AA   length = 107
FEATURE                 Location/Qualifiers
REGION                  1..107
                        note = Synthetic polypeptide: ADX_Y1236.ZZ0-1-Vk
source                  1..107
                        mol_type = protein
                        organism = synthetic construct
SEQUENCE: 79
DIVMTQSQKF MSTSVGDRIS ITCKASQNVR TAVAWYQQKP GQSPKALIYL ASNRHTGVPA    60
RFSGSGSGTS YSLTISRMEA EDAATYYCQQ RSSYPLTFGA GTKLELK                107

SEQ ID NO: 80           moltype = AA   length = 107
FEATURE                 Location/Qualifiers
REGION                  1..107
                        note = Synthetic polypeptide: ADX_Y1238.ZZ0-1-Vk
source                  1..107
                        mol_type = protein
                        organism = synthetic construct
SEQUENCE: 80
DIVMTQSHKF MSTSVGDRVS ITCKASQDVR TGVAWYQQKP GQSPKLLIYS ASYRNTGVPD    60
RFTGSRSGTD FTFTISSVQA EDLAVYYCQQ HYSPPYTFGG GTKLEIK                107

SEQ ID NO: 81           moltype = AA   length = 107
FEATURE                 Location/Qualifiers
REGION                  1..107
                        note = Synthetic polypeptide: ADX_Y1241.ZZ0-1-Vk
source                  1..107
                        mol_type = protein
                        organism = synthetic construct
SEQUENCE: 81
DIVMTQSHKF MSTSVGDRVS ITCKASQDVG TAVAWYQQKP GQSPKLLIYW ASTRHTGVPD    60
RFTGSGSGTD FTLTISNVQS EDLADYFCQQ YSSYPLTFGA GTKLELK                107

SEQ ID NO: 82           moltype = AA   length = 107
FEATURE                 Location/Qualifiers
REGION                  1..107
                        note = Synthetic polypeptide: ADX_Y1242.ZZ0-1-Vk
source                  1..107
                        mol_type = protein
                        organism = synthetic construct
SEQUENCE: 82
DIVMTQSHKF MSTSVGDRVS ITCKASQDVS TAVAWYQQKP GQSPKLLIYS ASYRYTGVPD    60
RFTGSGSGTD FTFTISSVQA EDLAVYYCQQ HYSTPYTFGG GTKLEIK                107

SEQ ID NO: 83           moltype = AA   length = 107
FEATURE                 Location/Qualifiers
REGION                  1..107
                        note = Synthetic polypeptide: ADX_Y1249.ZZ0-1-Vk
source                  1..107
                        mol_type = protein
                        organism = synthetic construct
SEQUENCE: 83
DIVMTQSHKF MSTSVGDRVS ITCKASQDVS TAVAWYQQKP GQSPKLLIYS ASYRYTGVPD    60
RFTGSGSGTD FTFTISSVQA EDLAVYYCQQ HYSTPWTFGG GTKLEIK                107

SEQ ID NO: 84           moltype = AA   length = 107
FEATURE                 Location/Qualifiers
REGION                  1..107
                        note = Synthetic polypeptide: ADX_Y1256.ZZ0-1-Vk
source                  1..107
                        mol_type = protein
                        organism = synthetic construct
SEQUENCE: 84
DIVMTQSHKF MSTSVGDRVS ITCKASQDVS TAVAWYQQKP GQSPKLLIYS ASYRYTGVPD    60
RFTGSGSGTD FTFTISSVQA EDLAVYYCQQ HYSTPWTFGG GTKLEIK                107

SEQ ID NO: 85           moltype = AA   length = 107
FEATURE                 Location/Qualifiers
REGION                  1..107
                        note = Synthetic polypeptide: ADX_Y1257.ZZ0-1-Vk
source                  1..107
                        mol_type = protein
                        organism = synthetic construct
SEQUENCE: 85
DIVMTQSHKF MSTSVGDRVS ITCKASQDVS TAVAWYQQKP GQSPKLLIYS ASYRYTGVPD    60
RFTGSGSGTD FTFTISSVQA EDLAVYYCQQ HYSTPWTFGG GTKLEIK                107
```

```
SEQ ID NO: 86              moltype = AA   length = 107
FEATURE                    Location/Qualifiers
REGION                     1..107
                           note = Synthetic polypeptide: ADX_Y1258.ZZ0-1-Vk
source                     1..107
                           mol_type = protein
                           organism = synthetic construct
SEQUENCE: 86
DIVMTQSHKF MSTSVGDRVS ITCKASQDVS TAVAWYQQKP GQSPKLLIYS ASYRYTGVPD    60
RFTGSGSGTD FTFTISSVQA EDLAVYYCQQ HYSTPWTFGG GTKLEIK                 107

SEQ ID NO: 87              moltype = AA   length = 107
FEATURE                    Location/Qualifiers
REGION                     1..107
                           note = Synthetic polypeptide: ADX_Y1259.ZZ0-1-Vk
source                     1..107
                           mol_type = protein
                           organism = synthetic construct
SEQUENCE: 87
DIVMTQSHKF MSTSVGDRVS ITCKASQDVS TAVAWYQQKP GQSPKLLIYS ASYRYTGVPD    60
RFTGSGSGTD FTFTISSVQA EDLAVYYCQQ HYSTPWTFGG GTKLEIK                 107

SEQ ID NO: 88              moltype = AA   length = 107
FEATURE                    Location/Qualifiers
REGION                     1..107
                           note = Synthetic polypeptide: ADX_Y1260.ZZ0-1-Vk
source                     1..107
                           mol_type = protein
                           organism = synthetic construct
SEQUENCE: 88
DIVMTQSHKF MSTSVGDRVS ITCKASQDVS TAVAWYQQKP GQSPKLLIYS ASYRYTGVPD    60
RFTGSGSGTD FTFTISSVQA EDLAVYYCQQ HYSTPWTFGG GTKLEIK                 107

SEQ ID NO: 89              moltype = AA   length = 107
FEATURE                    Location/Qualifiers
REGION                     1..107
                           note = Synthetic polypeptide: ADX_Y1261.ZZ0-1-Vk
source                     1..107
                           mol_type = protein
                           organism = synthetic construct
SEQUENCE: 89
DIVMTQSHKF MSTSVGDRVS ITCKASQDVS TAVAWYQQKP GQSPKLLIYS ASYRYTGVPD    60
RFTGSGSGTD FTFTISSVQA EDLAVYYCQQ HYSTPWTFGG GTKLEIK                 107

SEQ ID NO: 90              moltype = AA   length = 107
FEATURE                    Location/Qualifiers
REGION                     1..107
                           note = Synthetic polypeptide: ADX_Y1262.ZZ0-1-Vk
source                     1..107
                           mol_type = protein
                           organism = synthetic construct
SEQUENCE: 90
DIVMTQSHKF MSTSVGDRVS ITCKASQDVS TAVAWYQQKP GQSPKLLIYS ASYRYTGVPD    60
RFTGSGYGTD FTFTISSVQA EDLAVYYCQQ HYSTPWTFGG GTKLEIK                 107

SEQ ID NO: 91              moltype = AA   length = 107
FEATURE                    Location/Qualifiers
REGION                     1..107
                           note = Synthetic polypeptide: ADX_Y1263.ZZ0-1-Vk
source                     1..107
                           mol_type = protein
                           organism = synthetic construct
SEQUENCE: 91
DIVMTQSHKF MSTSVGDRVS ITCKASQDVS TAVAWYQQKP GQSPKLLIYS ASYRYTGVPD    60
RFTGSGSGTD FTFTISSVQA EDLAVYYCQQ HYSTPWTFGG GTKLEIK                 107

SEQ ID NO: 92              moltype = AA   length = 107
FEATURE                    Location/Qualifiers
REGION                     1..107
                           note = Synthetic polypeptide: ADX_Y1264.ZZ0-1-Vk
source                     1..107
                           mol_type = protein
                           organism = synthetic construct
SEQUENCE: 92
DIVMTQSHKF MSTSVGDRVS ITCKASQDVS TAVAWYQQKP GQSPKLLIYS ASYRYTGVPD    60
RFTGSGSGTD FTFTISSVQA EDLAVYYCHQ HYSTPWTFGG GTKLEIK                 107

SEQ ID NO: 93              moltype = AA   length = 107
```

```
FEATURE                 Location/Qualifiers
REGION                  1..107
                        note = Synthetic polypeptide: ADX_Y1265.ZZ0-1-Vk
source                  1..107
                        mol_type = protein
                        organism = synthetic construct
SEQUENCE: 93
DIVMTQSHKF MSTSVGDRVS ITCKASQDVS TAVAWYQQKP GQSPKLLIYS ASYRYTGVPD  60
RFTGSGSGTD FTFTISSVQA EDLAVYYCQQ HYSTPWTFGG GTKLEIK              107

SEQ ID NO: 94           moltype = AA   length = 107
FEATURE                 Location/Qualifiers
REGION                  1..107
                        note = Synthetic polypeptide: ADX_Y1266.ZZ0-1-Vk
source                  1..107
                        mol_type = protein
                        organism = synthetic construct
SEQUENCE: 94
DIVMTQSHKF MSTSVGDRVS ITCKASQDVS TAVAWYQQKP GQSPKLLIYS ASYRYTGVPD  60
RFTGSGSGTD FTFTISSVQA EDLAVYYCQQ HYSTPWTFGG GTKLEIK              107

SEQ ID NO: 95           moltype = AA   length = 107
FEATURE                 Location/Qualifiers
REGION                  1..107
                        note = Synthetic polypeptide: ADX_Y1267.ZZ0-1-Vk
source                  1..107
                        mol_type = protein
                        organism = synthetic construct
SEQUENCE: 95
DIVMTQSHKF MSTSVGDRVS ITCKASQDVS TAVAWYQQKP GQSPKLLIYS ASYRYTGVPD  60
RFTGSGSGTD FTFTISSVQA EDLAVYYCLQ HYTTPWTFGG GTKLEIK              107

SEQ ID NO: 96           moltype = AA   length = 107
FEATURE                 Location/Qualifiers
REGION                  1..107
                        note = Synthetic polypeptide: ADX_Y1268.ZZ0-1-Vk
source                  1..107
                        mol_type = protein
                        organism = synthetic construct
SEQUENCE: 96
DIVMTQSHKF MSTSVGDRVS ITCKASQDVS TAVAWYQQKP GQSPKLLIYS ASYRYTGVPD  60
RFTGSGSGTD FTFTISSVQA EDLAVYYCQQ HYSTPWTFGG GTKLEIK              107

SEQ ID NO: 97           moltype = AA   length = 107
FEATURE                 Location/Qualifiers
REGION                  1..107
                        note = Synthetic polypeptide: ADX_Y1269.ZZ0-1-Vk
source                  1..107
                        mol_type = protein
                        organism = synthetic construct
SEQUENCE: 97
DIVMTQSHKF MSTSVGDRVS ITCKASQDVS PNVAWYQQKP GQSPKLLIYS TSYRYTGVPD  60
RFTGSRSGTD FTFTISSVQA EDLAIYYCQQ HYSTPLTFGA GTKLELK              107

SEQ ID NO: 98           moltype = AA   length = 107
FEATURE                 Location/Qualifiers
REGION                  1..107
                        note = Synthetic polypeptide: ADX_Y1297.ZZ0-1-Vk
source                  1..107
                        mol_type = protein
                        organism = synthetic construct
SEQUENCE: 98
DIVMTQSHKF MSTSVGDRVS VTCKASQNVR INVAWYQQKP GQSPKALIYS ASYRYSGVPD  60
RFTGSGSGTD FTLTITNVQS EDLAEYFCQQ YNTYPLTFGA GTKLELK              107

SEQ ID NO: 99           moltype = AA   length = 117
FEATURE                 Location/Qualifiers
REGION                  1..117
                        note = Synthetic polypeptide: Vh-C1
source                  1..117
                        mol_type = protein
                        organism = synthetic construct
SEQUENCE: 99
QVQLQQSGAE LAKPGSSVKM SCKASGYAFT SYWMHWIKQR PGQGLEWIGF INPTTGYSEY  60
NQKFKDKATL TADKSSSTAY MQLNSLTSED SAVYFCARWG LPPPFAYWGQ GTLVTVSA   117

SEQ ID NO: 100          moltype = AA   length = 117
FEATURE                 Location/Qualifiers
REGION                  1..117
```

```
                        note = Synthetic polypeptide: Vh-hz1
source                  1..117
                        mol_type = protein
                        organism = synthetic construct
SEQUENCE: 100
QVQLVQSGAE VKKPGSSVKV SCKASGYAFT SYWMHWVRQA PGQGLEWMGF INPTTGYSEY    60
NQKFKDRVTI TADKSTSTAY MELSSLRSED TAVYYCARWG LPPFAYWGQG TLVTVSS      117

SEQ ID NO: 101          moltype = AA  length = 117
FEATURE                 Location/Qualifiers
REGION                  1..117
                        note = Synthetic polypeptide: Vh-hz2
source                  1..117
                        mol_type = protein
                        organism = synthetic construct
SEQUENCE: 101
QVQLVQSGAE VKKPGSSVKV SCKASGYAFT SYWMHWVRQR PGQGLEWMGF INPTTGYSEY    60
NQKFKDRVTI TADKSTSTAY MELSSLRSED TAVYYCARWG LPPFAYWGQG TLVTVSS      117

SEQ ID NO: 102          moltype = AA  length = 117
FEATURE                 Location/Qualifiers
REGION                  1..117
                        note = Synthetic polypeptide: Vh-hz3
source                  1..117
                        mol_type = protein
                        organism = synthetic construct
SEQUENCE: 102
QVQLVQSGAE VKKPGSSVKV SCKASGYAFT SYWMHWVRQR PGQGLEWIGF INPTTGYSEY    60
NQKFKDRVTI TADKSTSTAY MELNSLRSED TAVYYCARWG LPPFAYWGQG TLVTVSS      117

SEQ ID NO: 103          moltype = AA  length = 117
FEATURE                 Location/Qualifiers
REGION                  1..117
                        note = Synthetic polypeptide: Vh-C2
source                  1..117
                        mol_type = protein
                        organism = synthetic construct
SEQUENCE: 103
QVQLQQSGAE LAKPGSSVKM SCKASGYAFT SYWMHWVKQR PGQGLEWIGY INPTTGYSAY    60
NQKFKDKATL TADKSSSTAY MQLNSLTSED SAVYYCARWD PRPFAYWGQG TLVTVSA      117

SEQ ID NO: 104          moltype = AA  length = 117
FEATURE                 Location/Qualifiers
REGION                  1..117
                        note = Synthetic polypeptide: Vh-hz4
source                  1..117
                        mol_type = protein
                        organism = synthetic construct
SEQUENCE: 104
QVQLVQSGAE VKKPGSSVKV SCKASGYAFT SYWMHWVRQA PGQGLEWMGY INPTTGYSAY    60
NQKFKDKATL TADKSTSTAY MELSSLRSED TAVYYCARWD PRPFAYWGQG TLVTVSS      117

SEQ ID NO: 105          moltype = AA  length = 117
FEATURE                 Location/Qualifiers
REGION                  1..117
                        note = Synthetic polypeptide: Vh-hz5
source                  1..117
                        mol_type = protein
                        organism = synthetic construct
SEQUENCE: 105
QVQLVQSGAE VKKPGSSVKV SCKASGYAFT SYWMHWVRQR PGQGLEWMGY INPTTGYSAY    60
NQKFKDKATL TADKSTSTAY MELSSLRSED TAVYYCARWD PRPFAYWGQG TLVTVSS      117

SEQ ID NO: 106          moltype = AA  length = 117
FEATURE                 Location/Qualifiers
REGION                  1..117
                        note = Synthetic polypeptide: Vh-hz6
source                  1..117
                        mol_type = protein
                        organism = synthetic construct
SEQUENCE: 106
QVQLVQSGAE VKKPGSSVKV SCKASGYAFT SYWMHWVRQR PGQGLEWIGY INPTTGYSAY    60
NQKFKDKATL TADKSTSTAY MELNSLRSED TAVYYCARWD PRPFAYWGQG TLVTVSS      117

SEQ ID NO: 107          moltype = AA  length = 117
FEATURE                 Location/Qualifiers
REGION                  1..117
                        note = Synthetic polypeptide: Vh-hz7
source                  1..117
```

```
                        mol_type = protein
                        organism = synthetic construct
SEQUENCE: 107
QVQLVQSGAE VKKPGSSVKV SCKASGYAFT SYWMHWVRQA PGQGLEWMGY INPTTGYSAY      60
NQKFKDKATL TADKSTSTAY MELSSLRSED TAVYYCARWQ PRPFAYWGQG TLVTVSS        117

SEQ ID NO: 108          moltype = AA   length = 117
FEATURE                 Location/Qualifiers
REGION                  1..117
                        note = Synthetic polypeptide: Vh-hz8
source                  1..117
                        mol_type = protein
                        organism = synthetic construct
SEQUENCE: 108
QVQLVQSGAE VKKPGSSVKV SCKASGYAFT SYWMHWVRQA PGQGLEWMGY INPTTGYSAY      60
NQKFKDKATL TADKSTSTAY MELSSLRSED TAVYYCARWD ARPFAYWGQG TLVTVSS        117

SEQ ID NO: 109          moltype = AA   length = 117
FEATURE                 Location/Qualifiers
REGION                  1..117
                        note = Synthetic polypeptide: Vh-C3
source                  1..117
                        mol_type = protein
                        organism = synthetic construct
SEQUENCE: 109
QVQLQQPGAE LVKPGASVRL SCKASGYAFT SYWMHWVKQR PGQGLEWIGQ INPSNGRSQY      60
NEKFKTMATL TVDKSSSTAY IQLSSLTSED SAVYYCARWG LQPFAYWGQG TLVTVSA        117

SEQ ID NO: 110          moltype = AA   length = 117
FEATURE                 Location/Qualifiers
REGION                  1..117
                        note = Synthetic polypeptide: Vh-hz9
source                  1..117
                        mol_type = protein
                        organism = synthetic construct
SEQUENCE: 110
QVQLVQSGAE VKKPGSSVKV SCKASGYAFT SYWMHWVRQA PGQGLEWMGQ INPSNGRSQY      60
NEKFKTRVTI TADKSTSTAY MELSSLRSED TAVYYCARWG LQPFAYWGQG TLVTVSS        117

SEQ ID NO: 111          moltype = AA   length = 117
FEATURE                 Location/Qualifiers
REGION                  1..117
                        note = Synthetic polypeptide: Vh-hz10
source                  1..117
                        mol_type = protein
                        organism = synthetic construct
SEQUENCE: 111
QVQLVQSGAE VKKPGSSVKV SCKASGYAFT SYWMHWVRQR PGQGLEWMGQ INPSNGRSQY      60
NEKFKTRVTI TADKSTSTAY MELSSLRSED TAVYYCARWG LQPFAYWGQG TLVTVSS        117

SEQ ID NO: 112          moltype = AA   length = 117
FEATURE                 Location/Qualifiers
REGION                  1..117
                        note = Synthetic polypeptide: Vh-hz11
source                  1..117
                        mol_type = protein
                        organism = synthetic construct
SEQUENCE: 112
QVQLVQSGAE VKKPGSSVKV SCKASGYAFT SYWMHWVRQR PGQGLEWIGQ INPSNGRSQY      60
NEKFKTRVTI TADKSTSTAY MELSSLRSED TAVYYCARWG LQPFAYWGQG TLVTVSS        117

SEQ ID NO: 113          moltype = AA   length = 117
FEATURE                 Location/Qualifiers
REGION                  1..117
                        note = Synthetic polypeptide: Vh-hz13
source                  1..117
                        mol_type = protein
                        organism = synthetic construct
SEQUENCE: 113
QVQLVQSGAE VKKPGSSVKV SCKASGYAFT SYWMHWVRQA PGQGLEWMGQ INPSNARSQY      60
NEKFKTRVTI TADKSTSTAY MELSSLRSED TAVYYCARWG LQPFAYWGQG TLVTVSS        117

SEQ ID NO: 114          moltype = AA   length = 107
FEATURE                 Location/Qualifiers
REGION                  1..107
                        note = Synthetic polypeptide: Vk-C1
source                  1..107
                        mol_type = protein
                        organism = synthetic construct
```

```
SEQUENCE: 114
DIVMTQSHKF MSTSVGDRVS ITCKASQDVS TAVAWYQQKP GQSPKLLIYS ASYRYTGVPD    60
RFTGSGSGTD FTFTISSVQA EDLAVYYCQQ HYSTPWTFGG GTKLEIK                107

SEQ ID NO: 115          moltype = AA   length = 107
FEATURE                 Location/Qualifiers
REGION                  1..107
                        note = Synthetic polypeptide: Vk-C2
source                  1..107
                        mol_type = protein
                        organism = synthetic construct
SEQUENCE: 115
DIVMTQSHKF MSTSVGDRVS ITCKASQDVS TAVAWYQQKP GQSPKLLIYS ASYRYTGVPD    60
RFTGSGSGTD FTFTISSVQA EDLAVYYCQQ HYSTPWTFGG GTKLEIK                107

SEQ ID NO: 116          moltype = AA   length = 107
FEATURE                 Location/Qualifiers
REGION                  1..107
                        note = Synthetic polypeptide: Vk-hz1
source                  1..107
                        mol_type = protein
                        organism = synthetic construct
SEQUENCE: 116
DIQMTQSPSS LSASVGDRVT ITCKASQDVS TAVAWYQQKP GKAPKLLIYS ASYRYTGVPS    60
RFSGSGSGTD FTFTISSLQP EDIATYYCQQ HYSTPWTFGG GTKVEIK                107

SEQ ID NO: 117          moltype = AA   length = 330
FEATURE                 Location/Qualifiers
source                  1..330
                        mol_type = protein
                        organism = Homo sapiens
SEQUENCE: 117
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 118          moltype = AA   length = 232
FEATURE                 Location/Qualifiers
REGION                  1..232
                        note = Synthetic polypeptide: Fc consensus
VARIANT                 23
                        note = L, S, A, R, or W
VARIANT                 141
                        note = D or E
VARIANT                 143
                        note = L or M
VARIANT                 232
                        note = K or residue is absent
source                  1..232
                        mol_type = protein
                        organism = synthetic construct
SEQUENCE: 118
EPKSCDKTHT CPPCPAPELL GGXSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR XEXTKNQVSL TCLVKGFYPS DIAVEWESNG QPENNYKTTP   180
PVLDSDGSFF LYSKLTVDKS RWQQGNVFSC SVMHEALHNH YTQKSLSLSP GX          232

SEQ ID NO: 119          moltype = AA   length = 232
FEATURE                 Location/Qualifiers
REGION                  1..232
                        note = Synthetic polypeptide: Fc consensus
VARIANT                 141
                        note = D or E
VARIANT                 143
                        note = L or M
VARIANT                 232
                        note = K or residue is absent
source                  1..232
                        mol_type = protein
                        organism = synthetic construct
SEQUENCE: 119
EPKSCDKTHT CPPCPAPELL GGPSVFLFPP KPKDTLMISR TPEVTCVVVD VSHEDPEVKF    60
NWYVDGVEVH NAKTKPREEQ YASTYRVVSV LTVLHQDWLN GKEYKCKVSN KALPAPIEKT   120
ISKAKGQPRE PQVYTLPPSR XEXTKNQVSL TCLVKGFYPS DIAVEWESNG QPENNYKTTP   180
PVLDSDGSFF LYSKLTVDKS RWQQGNVFSC SVMHEALHNH YTQKSLSLSP GX          232
```

```
SEQ ID NO: 120          moltype = AA  length = 232
FEATURE                 Location/Qualifiers
REGION                  1..232
                        note = Synthetic polypeptide: Fc consensus
VARIANT                 23
                        note = L, S, A,  R, or W
VARIANT                 82
                        note = N or A
VARIANT                 141
                        note = D or E
VARIANT                 143
                        note = L or M
VARIANT                 232
                        note = K or residue is absent
source                  1..232
                        mol_type = protein
                        organism = synthetic construct
SEQUENCE: 120
EPKSCDKTHT  CPPCPAPELL  GGXSVFLFPP  KPKDTLMISR  TPEVTCVVVD  VSHEDPEVKF   60
NWYVDGVEVH  NAKTKPREEQ  YXSTYRVVSV  LTVLHQDWLN  GKEYKCKVSN  KALPAPIEKT  120
ISKAKGQPRE  PQVYTLPPSR  XEXTKNQVSL  TCLVKGFYPS  DIAVEWESNG  QPENNYKTTP  180
PVLDSDGSFF  LYSKLTVDKS  RWQQGNVFSC  SVMHEALHNH  YTQKSLSLSP  GX          232
```

ANTAGONISTIC CD40 MONOCLONAL ANTIBODIES AND USES THEREOF

CROSS REFERENCE TO RELATED APPLICATIONS

This application is a continuation of U.S. patent application Ser. No. 17/588,518, filed Jan. 31, 2022, now U.S. Pat. No. 11,773,178, issued on Oct. 3, 2023, which is a divisional of U.S. patent application Ser. No. 16/686,596, filed Nov. 18, 2019, now U.S. Pat. No. 11,261,258, issued on Mar. 1, 2022, which claims the benefit of U.S. Provisional Application No. 62/769,514, filed Nov. 19, 2018, each of which is hereby incorporated in its entirety for all purposes.

SEQUENCE LISTING

The instant application contains a Sequence Listing which has been submitted electronically in XML format and is hereby incorporated by reference in its entirety. Said XML copy, created on Aug. 21, 2023, is named 009616-00265-US.xml and is 175,082 bytes in size.

FIELD

The disclosure provides antibodies that bind CD40. The antibody polypeptides bind CD40 and do not exhibit CD40 agonist activity. The antibodies may comprise a modified IgG1 Fc domain, and exhibit minimal activation of immature dendritic cells. Compositions comprising antibodies, methods of use for treatment of diseases involving CD40 activity, and use in the preparation of a medicament for treatment of a disease involving CD40 activity are provided.

BACKGROUND

CD40 is a co-stimulatory molecule belonging to the tumor necrosis factor (TNF) receptor superfamily that is present on antigen presenting cells (APC), including dendritic cells, B cells, and macrophages. APCs are activated when CD40 binds its ligand, CD154 (CD40L), on $T_H$ cells. CD40-mediated APC activation is involved in a variety of immune responses, including cytokine production, up-regulation of co-stimulatory molecules (such as CD86), and enhanced antigen presentation and B cell proliferation. CD40 can also be expressed by endothelial cells, smooth muscle cells, fibroblasts, and epithelial cells.

CD40 activation is also involved in a variety of undesired T cell responses related to autoimmunity, transplant rejection, or allergic responses, for example. One strategy for controlling undesirable T cell responses is to target CD40 with an antagonistic antibody. For example, monoclonal antibody HCD122 (Lucatumumab), formerly known as Chiron 1212, is currently in clinical trials for the treatment of certain CD40-mediated inflammatory diseases. See "Study of HCD122 (Lucatumumab) and Bendamustine Combination Therapy in CD40+ Rituximab-Refractory Follicular Lymphoma," Clinical Trials Feeds, on the Internet at hypertext transfer protocol: clinicaltrialsfeeds.org/clinical-trials/show/NCT01275209 (last updated Jan. 11, 2011). Monoclonal antibodies, however, can display agonist activity. For example, the usefulness of the anti-CD40 antibody, Chi220, is limited by its weak stimulatory potential. See Adams, et al., "Development of a chimeric anti-CD40 monoclonal antibody that synergizes with LEA29Y to prolong islet allograft survival," *J. Immunol.* 174: 542-50 (2005).

SUMMARY

In a first embodiment, the present invention provides an isolated antibody, or antigen binding portion thereof, that specifically binds to human CD40, wherein the antibody comprises a first polypeptide portion comprising a heavy chain variable region, and a second polypeptide portion comprising a light chain variable region, wherein:
the heavy chain variable region comprises one of (i) a CDR1 comprising SYWMH (SEQ ID NO: 1), a CDR2 comprising QINPTTGRSQYNEKFKT (SEQ ID NO: 2), a CDR3 comprising WGLQPFAY (SEQ ID NO: 3); and (ii) a CDR1 comprising SYWMH (SEQ ID NO: 1), a CDR2 comprising QINPSQGRSQYNEKFKT (SEQ ID NO: 12), a CDR3 comprising WGLQPFAY (SEQ ID NO: 3); and
the light chain variable region comprises a CDR1 comprising KASQDVSTAVA (SEQ ID NO: 7), a CDR2 comprising SASYRYT (SEQ ID NO: 8), and a CDR3 comprising

```
                                        (SEQ ID NO: 9)
QQHYSTPWT.
```

The present invention further provides an isolated antibody or antigen binding portion thereof, that specifically binds to human CD40, wherein the antibody comprises a first polypeptide portion comprising a heavy chain variable region, and a second polypeptide portion comprising a light chain variable region, wherein:
the heavy chain variable region comprises one of (i) a CDR1 consisting of SYWMH (SEQ ID NO: 1), a CDR2 consisting of QINPTTGRSQYNEKFKT (SEQ ID NO: 2), a CDR3 consisting of WGLQPFAY (SEQ ID NO: 3); and (ii) a CDR1 consisting of SYWMH (SEQ ID NO: 1), a CDR2 consisting of QINPSQGR-SQYNEKFKT (SEQ ID NO: 12), a CDR3 consisting of WGLQPFAY (SEQ ID NO: 3); and
the light chain variable region comprises a CDR1 consisting of KASQDVSTAVA (SEQ ID NO: 7), a CDR2 consisting of SASYRYT (SEQ ID NO: 8), and a CDR3 consisting of

```
                                        (SEQ ID NO: 9)
QQHYSTPWT.
```

The present invention further provides an isolated antibody or antigen binding portion thereof, that specifically binds to human CD40, wherein the antibody comprises a first polypeptide portion comprising a heavy chain variable region, and a second polypeptide portion comprising a light chain variable region, wherein:
the heavy chain variable region comprises a CDR1 consisting of SYWMH (SEQ ID NO: 1), a CDR2 consisting QINPTTGRSQYNEKFKT (SEQ ID NO: 2), a CDR3 consisting of WGLQPFAY (SEQ ID NO: 3); and
the light chain variable region comprises a CDR1 consisting of KASQDVSTAVA (SEQ ID NO: 7), a CDR2 consisting of SASYRYT (SEQ ID NO: 8), and a CDR3 consisting of

```
                                        (SEQ ID NO: 9)
QQHYSTPWT.
```

The present invention further provides an isolated antibody or antigen binding portion thereof, that specifically binds to human CD40, wherein the antibody comprises a first polypeptide portion comprising a heavy chain variable region, and a second polypeptide portion comprising a light chain variable region, wherein:

the heavy chain variable region comprises the amino acid sequence of (SEQ ID NO: 4)
QVQLVQSGAEVKKPGSSVKVSCKASGYAFTSYWMHWVRQAP

GQGLEWMGQINPTTGRSQYNEKFKTRVTITADKSTSTAYME

LSSLRSEDTAVYYCARWGLQPFAYWGQGTLVTVSS, and the light chain variable region comprises the amino acid sequence of (SEQ ID NO: 10)
DIQMTQSPSFLSASVGDRVTITCKASQDVSTAVAWYQQKPG

KAPKLLIYSASYRYTGVPSRFSGSGSGTDFTLTISSLQPEDFA

TYYCQQHYSTPWTFGGGTKVEIK.

The present invention further provides an isolated antibody or antigen binding portion thereof, that specifically binds to human CD40, wherein the antibody comprises a first polypeptide portion comprising a heavy chain variable region, and a second polypeptide portion comprising a light chain variable region, wherein the heavy chain variable region comprises the amino acid sequence of (SEQ ID NO: 13)
QVQLVQSGAEVKKPGSSVKVSCKASGYAFTSYWMHWVRQAPG

QGLEWMGQINPSQGRSQYNEKFKTRVTITADKSTSTAYMELS

SLRSEDTAVYYCARWGLQPFAYWGQGTLVTVSS, and the light chain variable region comprises the amino acid sequence of (SEQ ID NO: 16)
EIVMTQSPATLSVSPGERATLSCKASQDVSTAVAWYQQKPGQAPRLLI

YSASYRYTGIPARFSGSGSGTEFTLTISSLQSEDFAVYYCQQHYSTPW

TFGGGTKVEIK.

The present invention further provides an isolated antibody or antigen binding portion thereof, that specifically binds to human CD40, wherein the antibody comprises a first polypeptide portion comprising a heavy chain variable region, and a second polypeptide portion comprising a light chain variable region, wherein the heavy chain variable region comprises the amino acid sequence of (SEQ ID NO: 4)
QVQLVQSGAEVKKPGSSVKVSCKASGYAFTSYWMHWVRQAPGQGLEWM

GQINPTTGRSQYNEKFKTRVTITADKSTSTAYMELSSLRSEDTAVYYC

ARWGLQPFAYWGQGTLVTVSS, and the light chain variable region comprises the amino acid sequence of (SEQ ID NO: 16)
EIVMTQSPATLSVSPGERATLSCKASQDVSTAVAWYQQKPGQAPRLLI

YSASYRYTGIPARFSGSGSGTEFTLTISSLQSEDFAVYYCQQHYSTPW

TFGGGTKVEIK.

In certain embodiments, the isolated antibody or antigen binding portion thereof comprises the first polypeptide portion comprising a human heavy chain constant region; and the second polypeptide portion comprising a human light chain constant region. The isolated antibody or antigen binding portion thereof described herein can comprise a human IgG1 Fc domain comprising either (1) a mutation at Kabat position 238 that reduces binding to Fc-gamma-receptors (FcγRs), wherein proline 238 (P238) is mutated to one of the residues selected from the group consisting of lysine, serine, alanine, arginine, and tryptophan, and wherein the antibody or antigen binding portion thereof has reduced FcγR binding; or (2) an alanine substituted at Kabat position 297.

The isolated antibody or antigen binding portion thereof described herein can comprise a human IgG1 Fc domain comprising a mutation at Kabat position 238 that reduces binding to Fc-gamma-receptors (FcγRs), wherein proline 238 (P238) is mutated to one of the residues selected from the group consisting of lysine, serine, alanine, arginine, and tryptophan, and wherein the antibody or antigen binding portion has reduced FcγR binding. In certain embodiments, P238 is mutated to lysine.

The isolated antibody or antigen binding portion thereof described herein can comprise an Fc domain which comprises an amino acid sequence selected from:

EPKSCDKTHTCPPCPAPELLGGKSVFLFPPKPKDTLMISRTPEVTCVV

VDVSHEDPEVKFNWYVDGVEVHNAKTKPREEQYNSTYRVVSVLTVLHQ

DWLNGKEYKCKVSNKALPAPIEKTISKAKGQPREPQVYTLPPSRDELT

KNQVSLTCLVKGFYPSDIAVEWESNGQPENNYKTTPPVLDSDGSFFLY

SKLTVDKSRWQQGNVFSCSVMHEALHNHYTQKSLSLSPG (SEQ ID

NO: 22; IgG1-P238K (-C-term Lys)),

EPKSCDKTHTCPPCPAPELLGGKSVFLFPPKPKDTLMISRTPEVTCVV

VDVSHEDPEVKFNWYVDGVEVHNAKTKPREEQYNSTYRVVSVLTVLHQ

DWLNGKEYKCKVSNKALPAPIEKTISKAKGQPREPQVYTLPPSRDELT

KNQVSLTCLVKGFYPSDIAVEWESNGQPENNYKTTPPVLDSDGSFFLY

SKLTVDKSRWQQGNVFSCSVMHEALHNHYTQKSLSLSPGK (SEQ ID

NO: 23; IgG1-P238K),

*ASTKGPSVFPLAPSSKSTSGGTAALGCLVKDYFPEPVTVSWNSGALTS*

*GVHTFPAVLQSSGLYSLSSVVTVPSSSLGTQTYICNVNHKPSNTKVDK*

*RVE*PKSCDKTHTCPPCPAPELLGGKSVFLFPPKPKDTLMISRTPEVTC

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFF

LYSKLTVDKSRWQQGNVFSCSVMHEALHNHYTQKSLSLSPG (SEQ

ID NO: 24; CH1-IgG1-P238K (-C-term Lys)),

*ASTKGPSVFPLAPSSKSTSGGTAALGCLVKDYFPEPVTVSWNSGALTS*

*GVHTFPAVLQSSGLYSLSSVVTVPSSSLGTQTYICNVNHKPSNTKVDK*

*RVEPKSCDKTHTCPPCPAPELLGG*K*SVFLFPPKPKDTLMISRTPEVTC*

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFF

LYSKLTVDKSRWQQGNVFSCSVMHEALHNHYTQKSLSLSPGK (SEQ

ID NO: 25; CH1-IgG1-P238K),

EPKSCDKTHTCPPCPAPELLGGKSVFLFPPKPKDTLMISRTPEVTCVV

VDVSHEDPEVKFNWYVDGVEVHNAKTKPREEQYNSTYRVVSVLTVLHQ

DWLNGKEYKCKVSNKALPAPIEKTISKAKGQPREPQVYTLPPSREEMT

KNQVSLTCLVKGFYPSDIAVEWESNGQPENNYKTTPPVLDSDGSFFLY

SKLTVDKSRWQQGNVFSCSVMHEALHNHYTQKSLSLSPG (SEQ ID

NO: 26; IgG1f-P238K (-C-term Lys)),

EPKSCDKTHTCPPCPAPELLGGKSVFLFPPKPKDTLMISRTPEVTCVV

VDVSHEDPEVKFNWYVDGVEVHNAKTKPREEQYNSTYRVVSVLTVLHQ

DWLNGKEYKCKVSNKALPAPIEKTISKAKGQPREPQVYTLPPSREEMT

KNQVSLTCLVKGFYPSDIAVEWESNGQPENNYKTTPPVLDSDGSFFLY

SKLTVDKSRWQQGNVFSCSVMHEALHNHYTQKSLSLSPGK (SEQ ID

NO: 27; IgG1f-P238K),

*ASTKGPSVFPLAPSSKSTSGGTAALGCLVKDYFPEPVTVSWNSGALTS*

*GVHTFPAVLQSSGLYSLSSVVTVPSSSLGTQTYICNVNHKPSNTKVDK*

*RVEPKSCDKTHTCPPCPAPELLGG*K*SVFLFPPKPKDTLMISRTPEVTC*

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSREE

MTKNQVSLTCLVKGFYPSDIAVEWESNGQPENNYKTTPPVLDSDGSFF

LYSKLTVDKSRWQQGNVFSCSVMHEALHNHYTQKSLSLSPG (SEQ

ID NO: 28; CH1-IgG1f-P238K (-C-term Lys)),
or

*ASTKGPSVFPLAPSSKSTSGGTAALGCLVKDYFPEPVTVSWNSGALTS*

*GVHTFPAVLQSSGLYSLSSVVTVPSSSLGTQTYICNVNHKPSNTKVDK*

*RVEPKSCDKTHTCPPCPAPELLGG*K*SVFLFPPKPKDTLMISRTPEVTC*

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSREE

MTKNQVSLTCLVKGFYPSDIAVEWESNGQPENNYKTTPPVLDSDGSFF

LYSKLTVDKSRWQQGNVFSCSVMHEALHNHYTQKSLSLSPGK (SEQ

ID No: 29; CH1-IgG1f-P238K).

In certain embodiments, the isolated antibody or antigen binding portion thereof described herein comprises a human IgG1 Fc domain comprising either (1) a mutation at Kabat position 238 that reduces binding to Fc-gamma-receptors (FcγRs), wherein proline 238 (P238) is mutated to one of the residues selected from the group consisting of lysine, serine, alanine, arginine, and tryptophan, and wherein the antibody or antigen binding portion thereof has reduced FcγR binding; or (2) an alanine substituted at Kabat position 297, comprises a heavy chain variable region comprising a CDR1 comprising SYWMH (SEQ ID NO: 1), a CDR2 comprising QINPTTGRSQYNEKFKT (SEQ ID NO: 2), a CDR3 comprising WGLQPFAY (SEQ ID NO: 3); and a light chain variable region comprising a CDR1 comprising KASQDVSTAVA (SEQ ID NO: 7), a CDR2 comprising SASYRYT (SEQ ID NO: 8), and a CDR3 comprising QQHYSTPWT (SEQ ID NO: 9).

The isolated antibody or antigen binding portion thereof can comprise a human IgG1 Fc domain comprising the amino acid sequence of SEQ ID NO: 22 or SEQ ID NO: 23.

In some embodiments of the isolated antibody or antigen binding portion thereof described herein, the first polypeptide portion comprises or consists of an amino acid sequence selected from the group consisting of:

QVQLVQSGAEVKKPGSSVKVSCKASGYAFTSYWMHWVRQAPGQGLEWM

GQINPTTGRSQYNEKFKTRVTITADKSTSTAYMELSSLRSEDTAVYYC

ARWGLQPFAYWGQGTLVTVSS*ASTKGPSVFPLAPSSKSTSGGTAALGC*

*LVKDYFPEPVTVSWNSGALTSGVHTFPAVLQSSGLYSLSSVVTVPSSS*

*LGTQTYICNVNHKPSNTKVDKRVEPKSCDKTHTCPPCPAPELLGG*K*SV*

FLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEAL

HNHYTQKSLSLSPG (SEQ ID NO: 5; HC_Y12XX-hz28-CH1-

IgG1-P238K- no terminal lysine),

QVQLVQSGAEVKKPGSSVKVSCKASGYAFTSYWMHWVRQAPGQGLEWM

GQINPTTGRSQYNEKFKTRVTITADKSTSTAYMELSSLRSEDTAVYYC

ARWGLQPFAYWGQGTLVTVSS*ASTKGPSVFPLAPSSKSTSGGTAALGC*

*LVKDYFPEPVTVSWNSGALTSGVHTFPAVLQSSGLYSLSSVVTVPSSS*

*LGTQTYICNVNHKPSNTKVDKRVEPKSCDKTHTCPPCPAPELLGG*K*SV*

FLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEAL

HNHYTQKSLSLSPGK (SEQ ID NO: 6; HC_Y12XX-hz28-

CH1-IgG1-P238K- with terminal lysine),

QVQLVQSGAEVKKPGSSVKVSCKASGYAFTSYWMHWVRQAPGQGLEWM

GQINPTTGRSQYNEKFKTRVTITADKSTSTAYMELSSLRSEDTAVYYC

ARWGLQPFAYWGQGTLVTVSS*ASTKGPSVFPLAPSSKSTSGGTAALGC*

-continued

LVKDYFPEPVTVSWNSGALTSGVHTFPAVLQSSGLYSLSSVVTVPSSS

LGTQTYICNVNHKPSNTKVDKRVEPKSCDKTHTCPPCPAPELLGGKSV

FLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEAL

HNHYTQKSLSLSPG (SEQ ID NO: 30; HC_Y12XX-hz28-

CH1-IgG1f-P238K- no terminal lysine), and

QVQLVQSGAEVKKPGSSVKVSCKASGYAFTSYWMHWVRQAPGQGLEWM

GQINPTTGRSQYNEKFKTRVTITADKSTSTAYMELSSLRSEDTAVYYC

ARWGLQPFAYWGQGTLVTVSSASTKGPSVFPLAPSSKSTSGGTAALGC

LVKDYFPEPVTVSWNSGALTSGVHTFPAVLQSSGLYSLSSVVTVPSSS

LGTQTYICNVNHKPSNTKVDKRVEPKSCDKTHTCPPCPAPELLGGKSV

FLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTI

SKAKGQPREPQVYTLPPSREEMTKNQVSLTCLVKGFYPSDIAVEWESN

GQPENNYKTTPPVLDSDGSFFLYSKLTVDKSRWQQGNVFSCSVMHEAL

HNHYTQKSLSLSPGK (SEQ ID NO: 31; HC_Y12XX-hz28-

CH1-IgG1f-P238K- with terminal lysine);

and the second polypeptide portion comprises or consists of the amino acid sequence of

DIQMTQSPSFLSASVGDRVTITCKASQDVSTAVAWYQQKPGKAPKLLI

YSASYRYTGVPSRFSGSGSGTDFTLTISSLQPEDFATYYCQQHYSTPW

TFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC (SEQ ID NO: 11;

LC_Y12XX-hz28-CL).

In some embodiments of the isolated antibody or antigen binding portion thereof described herein, the first polypeptide portion comprises or consists of an amino acid sequence of

QVQLVQSGAEVKKPGSSVKVSCKASGYAFTSYWMHWVRQAPGQGLEWM

GQINPTTGRSQYNEKFKTRVTITADKSTSTAYMELSSLRSEDTAVYYC

ARWGLQPFAYWGQGTLVTVSSASTKGPSVFPLAPSSKSTSGGTAALGC

LVKDYFPEPVTVSWNSGALTSGVHTFPAVLQSSGLYSLSSVVTVPSSS

LGTQTYICNVNHKPSNTKVDKRVEPKSCDKTHTCPPCPAPELLGGKSV

FLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEAL

HNHYTQKSLSLSPG (SEQ ID NO: 5; HC_Y12XX-hz28-CH1-

IgG1-P238K- no terminal lysine);

and the second polypeptide portion comprises or consists of the amino acid sequence of

DIQMTQSPSFLSASVGDRVTITCKASQDVSTAVAWYQQKPGKAPKLLI

YSASYRYTGVPSRFSGSGSGTDFTLTISSLQPEDFATYYCQQHYSTPW

TFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC (SEQ ID NO: 11;

LC_Y12XX-hz28-CL).

In certain embodiments, the isolated antibody or antigen binding portion thereof described herein comprises a human IgG1 Fc domain comprises a human IgG1 Fc domain comprising an alanine substituted at Kabat position 297.

The isolated antibody or antigen binding portion thereof as described herein can antagonize activities of CD40. The isolated antibody or antigen binding portion thereof described herein can be a chimeric antibody. The isolated antibody or antigen binding portion thereof described herein can be a humanized antibody. The isolated antibody or antigen binding portion thereof described herein can comprise a human heavy chain constant region and a human light chain constant region.

The antibody or antigen binding portion thereof disclosed herein, is an antigen binding portion selected from the group consisting of Fv, Fab, F(ab')2, Fab', dsFv, scFv, sc(Fv)2, diabodies, and scFv-Fc. The isolated antibody or antigen binding portion thereof as described herein is an scFv-Fc.

The antibody or antigen binding portion thereof disclosed herein can linked to a therapeutic agent.

The antibody or antigen binding portion thereof disclosed herein can be linked to a second functional moiety having a different binding specificity than said antibody or antigen binding portion thereof.

The antibody or antigen binding portion thereof disclosed herein can further comprise an additional moiety.

A nucleic acid molecule encoding an isolated antibody or antigen binding portion thereof is disclosed herein. An expression vector comprising the nucleic acid molecule is disclosed herein. Also contemplated is a cell transformed with the expression vector. Also disclosed is a method of preparing an anti-human CD40 antibody, or antigen binding portion thereof, comprising:

a) expressing the antibody, or antigen binding portion thereof, in the cell transformed with the expression vector comprising the nucleic acid molecule encoding an isolated antibody or antigen binding portion thereof disclosed herein; and b) isolating the antibody, or antigen binding portion thereof, from the cell.

Also provided is a pharmaceutical composition comprising: a) the antibody, or antigen binding portion thereof disclosed herein; and b) a pharmaceutically acceptable carrier.

A method is provided of treating or preventing an immune response in a subject comprising administering to the subject the antibody, or the antigen binding portion thereof, disclosed herein. Further provided is a method of treating or preventing an autoimmune or inflammatory disease in a subject, comprising administering to the subject the antibody, or the antigen binding portion, disclosed herein. Optionally, the antibody, or the antigen binding portion thereof, is administered with an immunosuppressive/immunomodulatory and/or anti-inflammatory agent. Administration may be simultaneous or sequential. An exemplary agent is a CTLA4 mutant molecule, such as L104EA29Y-Ig (belatacept). In such method of treating or preventing an immune response in the subject, and in such method of treating or preventing an autoimmune or inflammatory disease in a subject, preferably the subject has a disease selected from the group consisting of: Addison's disease, allergies, anaphylaxis, ankylosing spondylitis, asthma, atherosclerosis, atopic allergy, autoimmune diseases of the ear, autoimmune diseases of the eye, autoimmune hepatitis, autoimmune parotitis, bronchial asthma, coronary heart disease, Crohn's disease, diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products (e.g., Factor VII in hemophiliacs), lupus nephritis, lupus nephritis, systemic lupus erythematosus, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, vasculitis, and ulcerative colitis.

Also contemplated is an antibody, or antigen binding portion thereof as disclosed here, for use as a medicament. Further contemplated is an antibody, or antigen binding portion thereof as disclosed here, or a medicament comprising the same, for use to treat a subject in need thereof. Further contemplated is an antibody, or antigen binding portion thereof as disclosed herein in a therapeutically-effective amount, for use in treating or preventing an immune response, wherein the antibody or antigen binding portion thereof is for administering to a patient in need thereof.

BRIEF DESCRIPTION OF THE FIGURES

FIGS. 1A-1D depict SPR sensorgram data of binding of antibodies to human FcγRs. FIG. 1A depicts data for a control antibody, control IgG1. FIG. 1B depicts data for Y12XX-hx28-IgG1-P238K, control IgG1. FIG. 1C depicts data for a control antibody, Antibody B. FIG. 1D is a table summarizing the KD values for Antibody/FcγRs interactions. The KD values were obtained from either a 1:1 Langmuir fit (hCD64) or 1:1 steady state fit (hCD32a-H131, hCD32a-R131, hCD32b, hCD16a-V158, and hCD16a-F158).

FIGS. 2A-2C depict iDC activation data for treatment of iDCs with humanized Y12XX antibodies or control antibodies with or without the addition of CD32a-expressing CHO cells. Increases in IL-6 (interleukin-6) from the cell culture media and cell surface marker expression, as indicated by flow cytometry mean fluorescence staining with anti-CD86 and anti-CD54 antibodies, were assessed. FIG. 2A depicts IL-6 data. FIG. 2B depicts CD86 data. FIG. 2C depicts CD54 data. The mean fluorescence intensity (MFI) is measured on the Y-axis in both FIG. 2B and FIG. 2C. Each symbol represents data for iDC from an individual donor. Y12XX-hz42-P238K was tested in cells from 4 donors, Y12XX-hz40-P238K was tested in cells from 6 donors, and Y12XX-hz28-P238K was tested in 10 donors. Concentration of antibody in μg/ml is indicated (10, 30, or 100 μg/ml). Inclusion of CHO-CD32 cells in the assay is as indicated to mediate FcγR mediated cross-linking or clustering. Ly6-IgG was used as a negative control. Partial CD40 agonist 2141 and BMS986090-100 were used as positive controls.

FIG. 3A depicts the data from the first iteration of the assay, and FIG. 3B depicts the data from the second iteration of the assay.

FIG. 4A depicts data obtained with donor #8 CD14+ monocytes as effector cells. FIG. 4B depicts data obtained with donor #65 CD14+ monocytes as effector cells.

FIG. 5A depicts data obtained with donor #38 NK cells as effector cells. FIG. 5B depicts data obtained with donor #55 NK cells as effector cells.

FIGS. 6C and 6D depict data for the positive control, CD40L-IZ. AIMV: AIM V™ medium (1×) (Thermo Fisher Scientific, Waltham, MA).

DETAILED DESCRIPTION

Figure 1A:
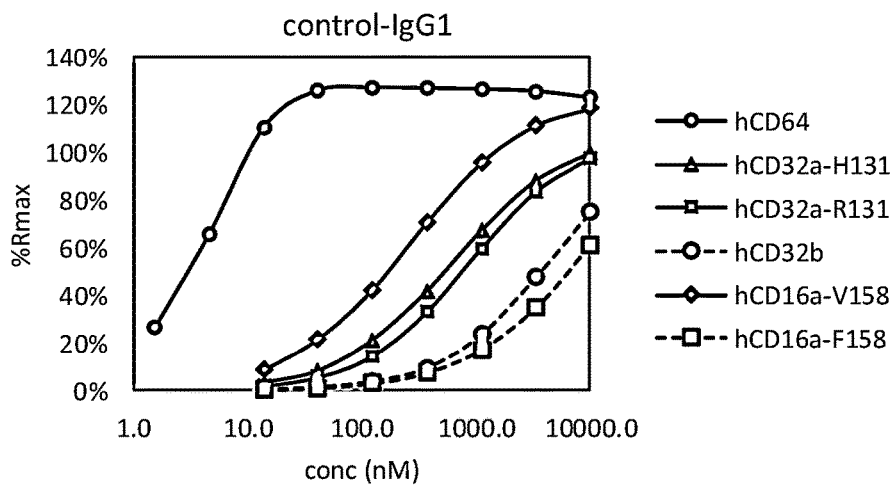

The present disclosure is directed to anti-CD40 antibodies, and in particular, antagonistic anti-CD40 antibodies. For therapeutic targets such as CD40, FcγR-mediated cross-linking of anti-CD40 antibodies has the potential to lead to undesirable agonist signaling and potential for toxicity. The present disclosure also describes antagonistic anti-CD40 antibodies having reduced engagement of the "low affinity" FcγRs: hCD32a/FcγRIIa, hCD32b/FcγRIIb, and hCD16a/FcγRIIIa, as well as reduced engagement to "high affinity" FcγR hCD64. Reduced engagement of low affinity FcγRs is expected to reduce the likelihood of undesirable agonist signaling and undesirable potential for toxicity.

DEFINITIONS & ABBREVIATIONS

Further abbreviations and definitions are provided below.

| | |
|---|---|
| APC | antigen presenting cells |
| CD54 | also referred to as ICAM-1 |
| CDR | complementarity determining regions |
| $C_H$ or CH | constant heavy chain |
| $C_L$ or CL | constant light chain |
| CHO cell | Chinese hamster ovary cell |
| dAb | domain antibody |
| DC | dendritic cell |
| FcgR | interchangeable with FcγR |
| FcγR | Fc-gamma-receptor |
| FR | Framework region |
| GM-CSF | granulocyte macrophage colony stimulating factor |
| HC | heavy chain |

| | |
|---|---|
| ICAM-1 | intracellular adhesion molecule 1 |
| iDC | immature dendritic cells |
| IFN | interferon |
| IgG | immunoglobulin G |
| IL-6 | interleukin-6 |
| LC | light chain |
| mAb | monoclonal antibody |
| mg | milligram |
| ml or mL | milliliter |
| ng | nanogram |
| nM | nanomolar |
| pI | isoelectric point |
| SPR | surface plasmon resonance |
| TNF | tumor necrosis factor |
| μg | microgram |
| μM | micromolar |
| $V_L$ or VL | variable light chain domain |
| $V_k$ or VK | kappa variable light chain domain |
| $V_H$ or VH | variable heavy chain domain |

In accordance with this detailed description, the following abbreviations and definitions apply. It must be noted that as used herein, the singular forms "a", "an", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

As used here, the term "about" is understood by persons of ordinary skill in the art and will vary to some extent on the context in which it is used. Generally, "about" encompasses a range of values that are plus/minus 10% of a referenced value unless indicated otherwise in the specification.

It is understood that any and all whole or partial integers between the ranges set forth are included herein.

CD40 is also known and referred to as B-cell surface antigen CD40, Bp50, CD40L receptor, CDw40, CDW40, MGC9013, p50, TNFRSF5, and Tumor necrosis factor receptor superfamily member 5. "Human CD40" refers to the CD40 comprising the following amino acid sequence:

```
                                        (SEQ ID NO: 20)
MVRLPLQCVL WGCLLTAVHP EPPTACREKQ YLINSQCCSL

CQPGQKLVSD CTEFTETECL PCGESEFLDT WNRETHCHQH

KYCDPNLGLR VQQKGTSETD TICTCEEGWH CTSEACESCV

LHRSCSPGFG VKQIATGVSD TICEPCPVGF FSNVSSAFEK

CHPWTSCETK DLVVQQAGTN KTDVVCGPQD RLRALVVIPI

IFGILFAILL VLVFIKKVAK KPTNKAPHPK QEPQEINFPD

DLPGSNTAAP VQETLHGCQP VTQEDGKESR ISVQERQ.
```

As used herein, the term "variable domain" refers to immunoglobulin variable domains defined by Kabat et al., Sequences of Immunological Interest, 5th ed., U.S. Dept. Health & Human Services, Washington, D.C. (1991). The numbering and positioning of CDR amino acid residues within the variable domains is in accordance with the well-known Kabat numbering convention. VH, "variable heavy chain" and "variable heavy chain domain" refer to the variable domain of a heavy chain. VL, "variable light chain" and "variable light chain domain" refer to the variable domain of a light chain.

The term "human," when applied to antibodies, means that the antibody has a sequence, e.g., FR and/or CH domains, derived from a human immunoglobulin. A sequence is "derived from" a human immunoglobulin coding sequence when the sequence is either: (a) isolated from a human individual or from a cell or cell line from a human individual; (b) isolated from a library of cloned human antibody gene sequences or of human antibody variable domain sequences; or (c) diversified by mutation and selection from one or more of the polypeptides above.

An "isolated" compound as used herein means that the compound is removed from at least one component with which the compound is naturally associated with in nature.

The anti-CD40 antibody of the present disclosure comprise a variable heavy chain and a variable light chain, each of which contains three complementarity-determining regions (CDRs) and four framework regions (FRs), arranged from amino-terminus to carboxy-terminus in the following order: FR1, CDR1, FR2, CDR2, FR3, CDR3, FR4. The CDRs contain most of the residues that form specific interactions with the antigen and are primarily responsible for antigen recognition.

The anti-CD40 antibody of the present disclosure can comprise CDRs of humanized antibody Y12XX-hz28 (Vh-hz14; Vk-hz2), Y12XX-hz40 (Vh-hz12; Vk-hz3), or Y12XX-hz42 (Vh-hz14; Vk-hz3). An overview of the amino acid sequences of the heavy chain variable region and light chain variable region is provided in Table 1. The table includes a short hand name and a more detailed name for each amino acid sequence, as well as the sequence identifiers.

TABLE 1

| Antibody | HC Variable Region | LC Variable Region |
|---|---|---|
| Y12XX-hz28 | Vh-hz14 (Y1268_IGHV1.6908-S54T-N55T-Vh) (SEQ ID NO: 4) | Vk-hz2 (Y1258_IGKV1.3902-Vk) (SEQ ID NO: 10) |
| Y12XX-hz40 | Vy-hz12 (Y1268_IGHV1.6908-N55Q-Vh) (SEQ ID NO: 13) | Vk-hz3 (Y1258_IGKV3.1501-Vk) (SEQ ID NO: 16) |
| Y12XX-hz42 | Vh-hz14 (Y1268_IGHV1.6908-S54T-N55T-Vh) (SEQ ID NO: 4) | Vk-hz3 (Y1258_IGKV3.1501-Vk) (SEQ ID NO: 16) |

In a specific embodiment, the anti-CD40 antibodies of the present disclosure comprises the CDRs of humanized antibody Y12XX-hz28 (Vh-hz14; Vk-hz2). Detail of the amino acid sequences of Y12XX-hz28 is provided in Table 2.

TABLE 2

Y12XX-hz28 sequences (Vh-hz14; Vk-hz2)

| Heavy chain variable region | QVQLVQSGAEVKKPGSSVKVSCKASGYAFTSYWMHWVRQ APGQGLEWMGQINPTTGRSQYNEKFKTRVTITADKSTST AYMELSSLRSEDTAVYYCARWGLQPFAYWGQGTLVTVSS SEQ ID NO: 4) | Vh-hz14 (SEQ. ID NO: 4; CDRs underlined) |
|---|---|---|

TABLE 2-continued

Y12XX-hz28 sequences (Vh-hz14; Vk-hz2)

| | | |
|---|---|---|
| VH-CDR1 | SYWMH<br>SEQ ID NO: 1) | Amino acids 31-35 of SEQ ID NO: 4 |
| VH-CDR2 | QINPTTGRSQYNEKFKT<br>(SEQ ID NO: 2) | Amino acids 50-66 of SEQ ID NO: 4 |
| VH-CDR3 | WGLQPFAY<br>(SEQ ID NO: 3) | Amino acids 99-106 of SEQ ID NO: 4 |
| HC_Y12XX-hz28-CH1-IgG1-P238K (is IgG1 with and without C-terminal lysine) | QVQLVQSGAEVKKPGSSVKVSCKASGYAFTSYWMHWVRQ APGQGLEWMGQINPTTGRSQYNEKFKTRVTITADKSTST AYMELSSLRSEDTAVYYCARWGLQPFAYWGQGTLVTVSS *ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKR*VEPKSCDKTHTCPPCPAPEL LGGKSVFLFPPKPKDTLMISRTPEVTCVVVDVSHEDPEV KFNWYVDGVEVHNAKTKPREEQYNSTYRVVSVLTVLHQD WLNGKEYKCKVSNKALPAPIEKTISKAKGQPREPQVYTL PPSRDELTKNQVSLTCLVKGFYPSDIAVEWESNGQPENN YKTTPPVLDSDGSFFLYSKLTVDKSRWQQGNVFSCSVMH EALHNHYTQKSLSLSPG<br>(SEQ ID NO: 5) | CDRs underlined;<br>CH1 = amino acids 118-215 (italicized); IgG1-P238K = amino acids 216-446; P238K underlined;<br>no C-terminal lysine |
| | QVQLVQSGAEVKKPGSSVKVSCKASGYAFTSYWMHWVRQ APGQGLEWMGQINPTTGRSQYNEKFKTRVTITADKSTST AYMELSSLRSEDTAVYYCARWGLQPFAYWGQGTLVTVSS *ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKR*VEPKSCDKTHTCPPCPAPEL LGGKSVFLFPPKPKDTLMISRTPEVTCVVVDVSHEDPEV KFNWYVDGVEVHNAKTKPREEQYNSTYRVVSVLTVLHQD WLNGKEYKCKVSNKALPAPIEKTISKAKGQPREPQVYTL PPSRDELTKNQVSLTCLVKGFYPSDIAVEWESNGQPENN YKTTPPVLDSDGSFFLYSKLTVDKSRWQQGNVFSCSVMH EALHNHYTQKSLSLSPGK (SEQ ID NO: 6) | CDRs underlined;<br>CH1 = amino acids 118-215 (italicized); IgG1-P238K = amino acids 216-447; P238K underlined;<br>C-terminal lysine present |
| Light chain variable region | DIQMTQSPSFLSASVGDRVTITCKASQDVSTAVAWYQQK PGKAPKLLIYSASYRYTGVPSRFSGSGSGTDFTLTISSL QPEDFATYYCQQHYSTPWTFGGGTKVEIK<br>(SEQ ID NO: 10) | Vk-hz2<br>(SEQ ID NO: 10; CDRs underlined) |
| VL-CDR1 | KASQDVSTAVA<br>(SEQ ID NO: 7) | Amino acids 24-34 of SEQ ID NO: 10 |
| VL-CDR2 | SASYRYT<br>(SEQ ID NO: 8) | Amino acids 50-56 of SEQ ID NO: 10 |
| VL-CDR3 | QQHYSTPWT<br>(SEQ ID NO: 9) | Amino acids 89-97 of SEQ ID NO: 10 |
| LC_Y12XX-hz28 | DIQMTQSPSFLSASVGDRVTITCKASQDVSTAVAWYQQK PGKAPKLLIYSASYRYTGVPSRFSGSGSGTDFTLTISSL QPEDFATYYCQQHYSTPWTFGGGTKVEIK*RTVAAPSVFI FPPSDEQLKSGTASVVCLLNNFYPREAKVQWKVDNALQS GNSQESVTEQDSKDSTYSLSSTLTLSKADYEKHKVYACE VTHQGLSSPVTKSFNRGEC*<br>(SEQ ID NO: 11) | CDRs underlined;<br>CL = amino acids 108-214 (italicized) |

In a specific embodiment, the anti-CD40 antibody of the present disclosure comprises the CDRs of humanized antibody Y12XX-hz40 (Vh-hz12; Vk-hz3). Amino acid sequences of Y12XX-hz40 are provided in Table 3.

TABLE 3

Y12XX-hz40 sequences (Vh-hz12; Vk-hz3)

| | | |
|---|---|---|
| Heavy chain variable region | QVQLVQSGAEVKKPGSSVKVSCKASGYAFTSYWMHWVRQ APGQGLEWMGQINPSQGRSQYNEKFKTRVTITADKSTST AYMELSSLRSEDTAVYYCARWGLQPFAYWGQGTLVTVSS<br>(SEQ ID NO: 13) | Vh-hz12 (SEQ ID NO: 13; CDRs underlined) |
| VH-CDR1 | SYWMH<br>(SEQ ID NO: 1) | Amino acids 31-35 of SEQ ID NO: 13 |

TABLE 3-continued

Y12XX-hz40 sequences (Vh-hz12; Vk-hz3)

| | | |
|---|---|---|
| VH-CDR2 | QINPSQGRSQYNEKFKT<br>(SEQ ID NO: 12) | Amino acids 50-66 of SEQ ID NO: 13 |
| VH-CDR3 | WGLQPFAY<br>(SEQ ID NO: 3) | Amino acids 99-106 of SEQ ID NO: 13 |
| HC_Y12XX-hz40-P238K-IgG1a with and without C-terminal lysine | QVQLVQSGAEVKKPGSSVKVSCKASGYAFTSYWMHWVRQ APGQGLEWMGQINPSQGRSQYNEKFKTRVTITADKSTST AYMELSSLRSEDTAVYYCARWGLQPFAYWGQGTLVTVSS *ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKR*VEPKSCDKTHTCPPCPAPEL LGGKSVFLPPKPKDTLMISRTPEVTCVVVDVSHEDPEV KFNWYVDGVEVHNAKTKPREEQYNSTYRVVSVLTVLHQD WLNGKEYKCKVSNKALPAPIEKTISKAKGQPREPQVYTL PPSRDELTKNQVSLTCLVKGFYPSDIAVEWESNGQPENN YKTTPPVLDSDGSFFLYSKLTVDKSRWQQGNVFSCSVMH EALHNHYTQKSLSLSPG<br>(SEQ ID NO: 14) | CDRs underlined;<br>CH1 = amino acids 118-215 (italicized); IgG1-P238K = amino acids 216-446; P238K underlined; no C-terminal lysine |
| | QVQLVQSGAEVKKPGSSVKVSCKASGYAFTSYWMHWVRQ APGQGLEWMGQINPSQGRSQYNEKFKTRVTITADKSTST AYMELSSLRSEDTAVYYCARWGLQPFAYWGQGTLVTVSS *ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKR*VEPKSCDKTHTCPPCPAPEL LGGKSVFLPPKPKDTLMISRTPEVTCVVVDVSHEDPEV KFNWYVDGVEVHNAKTKPREEQYNSTYRVVSVLTVLHQD WLNGKEYKCKVSNKALPAPIEKTISKAKGQPREPQVYTL PPSRDELTKNQVSLTCLVKGFYPSDIAVEWESNGQPENN YKTTPPVLDSDGSFFLYSKLTVDKSRWQQGNVFSCSVMH EALHNHYTQKSLSLSPGK<br>(SEQ ID NO: 15) | CDRs underlined;<br>CH1 = amino acids 118-215 (italicized); IgG1-P238K = amino acids 216-447; P238K underlined; C-terminal lysine present |
| Light chain variable region | EIVMTQSPATLSVSPGERATLSCKASQDVSTAVAWYQQK PGQAPRLLIYSASYRYTGIPARFSGSGSGTEFTLTISSL QSEDFAVYYCQQHYSTPWTFGGGTKVEIK<br>(SEQ ID NO: 16) | Vk-hz3 (SEQ ID NO: 16; CDRs underlined) |
| VL-CDR1 | KASQDVSTAVA<br>(SEQ ID NO: 7) | Amino acids 24-34 of SEQ ID NO: 16 |
| VL-CDR2 | SASYRYT<br>(SEQ ID NO: 8) | Amino acids 50-56 of SEQ ID NO: 16 |
| VL-CDR3 | QQHYSTPWT<br>(SEQ ID NO: 9) | Amino acids 89-97 of SEQ ID NO: 16 |
| LC_Y12XX-hz40 | EIVMTQSPATLSVSPGERATLSCKASQDVSTAVAWYQQK PGQAPRLLIYSASYRYTGIPARFSGSGSGTEFTLTISSL QSEDFAVYYCQQHYSTPWTFGGGTKVEIK*RTVAAPSVFI FPPSDEQLKSGTASVVCLLNNFYPREAKVQWKVDNALQS GNSQESVTEQDSKDSTYSISSTLTLSKADYEKHKVYACE VTHQGLSSPVTKSFNRGEC*<br>(SEQ ID NO: 17) | CDRs underlined;<br>CL = amino acids 108-214 (italicized) |

In a specific embodiment, the anti-CD40 antibody of the present disclosure comprises the CDRs of humanized antibody Y12XX-hz42 (Vh-hz14; Vk-hz3). Detail of the amino acid sequences of Y12XX-hz42 is provided in Table 4.

TABLE 4

Y12XX-hz42 sequences (Vh-hz14;Vk-hz3)

| | | |
|---|---|---|
| Heavy chain variable region | QVQLVQSGAEVKKPGSSVKVSCKASGYAFTSYWMHWVRQ APGQGLEWMGQINPTTGRSQYNEKFKTRVTITADKSTST AYMELSSLRSEDTAVYYCARWGLQPFAYWGQGTLVTVSS<br>SEQ ID NO: 4) | Vh-hz14<br>(SEQ ID NO: 4; CDRs underlined) |
| VH-CDR1 | SYWMH<br>SEQ ID NO: 1) | Amino acids 31-35 of SEQ ID NO: 4 |
| VH-CDR2 | QINPTTGRSQYNEKFKT<br>(SEQ ID NO: 2) | Amino acids 50-66 of SEQ ID NO: 4 |

TABLE 4-continued

Y12XX-hz42 sequences (Vh-hz14;Vk-hz3)

| | | |
|---|---|---|
| VH-CDR3 | WGLQPFAY<br>(SEQ ID NO: 3) | Amino acids 99-106 of<br>SEQ ID NO: 4 |
| HC_Y12XX-<br>hz42-P238K-<br>IgG1a with<br>and without<br>C-terminal<br>lysine | QVQLVQSGAEVKKPGSSVKVSCKASGYAFTSYWMHWVRQ<br>APGQGLEWMGQINPTTGRSQYNEKFKTRVTITADKSTST<br>AYMELSSLRSEDTAVYYCARWGLQPFAYWGQGTLVTVSS<br>*ASTKGPSVFPLAPSSKSTSGGTAALGCLVKDYFPEPVTV<br>SWNSGALTSGVHTFFPAVLQSSGLYSLSSVVTVPSSSLGT<br>QTYICNVNHKPSNTKVDKR*VEPKSCDKTHTCPPCPAPEL<br>LGG<u>K</u>SVFLFPPKPKDTLMISRTPEVTCVVVDVSHEDPEV<br>KFN<u>W</u>YVDGVEVHNAKTKPREEQYNSTYRVVSVLTVLHQD<br>WLNGKEYKCKVSNKALPAPIEKTISKAKGQPREPQVYTL<br>PPSRDELTKNQVSLTCLVKGFYPSDIAVEWESNGQPENN<br>YKTTPPVLDSDGSFFLYSKLTVDKSRWQQGNVFSCSVMH<br>EALHNHYTQKSLSLSPG<br>(SEQ ID NO: 5) | CDRs underlined;<br>CH1 = amino acids 118-<br>215 (italicized); IgG1-<br>P238K = amino acids 216-<br>446; P238K underlined;<br>no C-terminal lysine |
| | QVQLVQSGAEVKKPGSSVKVSCKASGYAFTSYWMHWVRQ<br>APGQGLEWMGQINPTTGRSQYNEKFKTRVTITADKSTST<br>AYMELSSLRSEDTAVYYCARWGLQPFAYWGQGTLVTVSS<br>*ASTKGPSVFPLAPSSKSTSGGTAALGCLVKDYFPEPVTV<br>SWNSGALTSGVHTFFPAVLQSSGLYSLSSVVTVPSSSLGT<br>QTYICNVNHKPSNTKVDKR*VEPKSCDKTHTCPPCPAPEL<br>LGG<u>K</u>SVFLEPPKPKDTLMISRTPEVTCVVVDVSHEDPEV<br>KFN<u>W</u>YVDGVEVHNAKTKPREEQYNSTYRVVSVLTVLHQD<br>WLNGKEYKCKVSNKALPAPIEKTISKAKGQPREPQVYTL<br>PPSRDELTKNQVSLTCLVKGFYPSDIAVEWESNGQPENN<br>YKTTPPVLDSDGSFFLYSKLTVDKSRWQQGNVFSCSVMH<br>EALHNHYTQKSLSLSPGK<br>(SEQ ID NO: 6) | CDRs underlined;<br>CH1 = amino acids 118-<br>215 (italicized); IgG1-<br>P238K = amino acids 216-<br>447; P238K underlined;<br>C-terminal lysine present |
| Light chain<br>variable<br>region | EIVMTQSPATLSVSPGERATLSCKASQDVSTAVAWYQQK<br>PGQAPRLLIYSASYRYTGIPARFSGSGSGTEFTLTISSL<br>QSEDFAVYYCQQHYSTPWTFGGGTKVEIK<br>(SEQ ID NO: 16) | Vk-hz3 (SEQ ID NO: 16;<br>CDRs underlined) |
| VL-CDR1 | KASQDVSTAVA<br>(SEQ ID NO: 7) | Amino acids 24-34 of SEQ<br>ID NO: 16 |
| VL-CDR2 | SASYRYT<br>(SEQ ID NO: 8) | Amino acids 50-56 of SEQ<br>ID NO: 16 |
| VL-CDR3 | QQHYSTPWT<br>(SEQ ID NO: 9) | Amino acids 89-97 of SEQ<br>ID NO: 16 |
| LC_Y12XX-<br>hz42 | EIVMTQSPATLSVSPGERATLSCKASQDVSTAVAWYQQK<br>PGQAPRLLIYSASYRYTGIPARFSGSGSGTEFTLTISSL<br>QSEDFAVYYCQQHYSTPWTFGGGTKVEIK*RTVAAPSVFI<br>FPPSDEQLKSGTASVVCLLNNFYPREAKVQWKVDNALQS<br>GNSQESVTEQDSKDSTYSLSSTLTLSKADYEKHKVYACE<br>VTHQGLSSPVTKSFNRGEC*<br>(SEQ ID NO: 17) | CDRs underlined;<br>CL = amino acids 108-214<br>(italicized) |

In one embodiment, the antibodies of the disclosure can comprise the amino acid sequences of the CDR1, CDR2, and CDR3 regions of the humanized Y12XX-hz28 variable heavy and light chains sequences (see e.g., SEQ ID NOS: 4 and 10 respectively, as an example). Monoclonal antibodies contain all 6 CDRs (3 for the V$_H$ and 3 for the V$_L$), for example, SYWMH (SEQ ID NO: 1), QINPTTGRSQYNEKFKT (SEQ ID NO: 2), and WGLQPFAY (SEQ ID NO: 3) for the variable heavy chain CDRs 1-3 respectively and KASQDVSTAVA (SEQ ID NO: 7), SASYRYT (SEQ ID NO: 8), and QQHYSTPWT (SEQ ID NO: 9) for the variable light chain CDRs 1-3 respectively.

In one embodiment, the antibodies of the disclosure can comprise the amino acid sequences of the CDR1, CDR2, and CDR3 regions of the humanized Y12XX-hz40 variable heavy and light chains sequences (see e.g., SEQ ID NOS: 13 and 16 respectively, as an example). Monoclonal antibodies contain all 6 CDRs (3 for the V$_H$ and 3 for the V$_L$), for example, SYWMH (SEQ ID NO: 1), QINPSQGRSQYNEKFKT (SEQ ID NO: 12), and WGLQPFAY (SEQ ID NO: 3) for the variable heavy chain CDRs 1-3 respectively and KASQDVSTAVA (SEQ ID NO: 7), SASYRYT (SEQ ID NO: 8), and QQHYSTPWT (SEQ ID NO: 9) for the variable light chain CDRs 1-3 respectively.

In one embodiment, the antibodies of the disclosure can comprise the amino acid sequences of the CDR1, CDR2, and CDR3 regions of the humanized Y12XX-hz42 variable heavy and light chains sequences (see e.g., SEQ ID NOS: 4 and 16 respectively, as an example). Monoclonal antibodies contain all 6 CDRs (3 for the V$_H$ and 3 for the V$_L$), for example, SYWMH (SEQ ID NO: 1), QINPTTGRSQYNEKFKT (SEQ ID NO: 2), and WGLQPFAY (SEQ ID NO: 3) for the variable heavy chain CDRs 1-3 respectively and KASQDVSTAVA (SEQ ID NO: 7), SASYRYT (SEQ ID NO: 8), and QQHYSTPWT (SEQ ID NO: 9) for the variable light chain CDRs 1-3 respectively.

An "antibody" (Ab) shall include, without limitation, an immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen.

An "antigen binding portion" of an Ab (also called an "antigen-binding fragment") or antigen binding portion thereof refers to one or more sequences of an Ab (full length or fragment of the full length antibody) that retain the ability to bind specifically to the antigen bound by the whole Ab. Examples of an antigen-binding fragment include Fab, F(ab')₂, scFv (single-chain variable fragment), Fab', dsFv, sc(Fv)2, and scFv-Fc.

A "humanized" antibody refers to an Ab in which some, most or all of the amino acids outside the CDR domains of a non-human Ab are replaced with corresponding amino acids derived from human immunoglobulins. In one embodiment of a humanized form of an Ab, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the Ab to bind to a particular antigen. A "humanized" Ab retains an antigenic specificity similar to that of the original Ab.

A "chimeric antibody" refers to an Ab in which the variable regions are derived from one species and the constant regions are derived from another species, such as an Ab in which the variable regions are derived from a mouse Ab and the constant regions are derived from a human Ab.

As used herein, "specific binding" refers to the binding of an antigen by an antibody with a dissociation constant ($K_d$) of about 1 μM or lower as measured, for example, by surface plasmon resonance (SPR). Suitable assay systems include the BIAcore™ (GE Healthcare Life Sciences, Marlborough, MA) surface plasmon resonance system and BIAcore™ kinetic evaluation software (e.g., version 2.1).

Binding of the present antibodies to CD40 antagonizes at least one CD40 activity. "CD40 activities" include, but are not limited to, T cell activation (e.g., induction of T cell proliferation or cytokine secretion), macrophage activation (e.g., the induction of reactive oxygen species and nitric oxide in the macrophage), and B cell activation (e.g., B cell proliferation, antibody isotype switching, or differentiation to plasma cells). CD40 activities can be mediated by interaction with other molecules. "CD40 activities" include the functional interaction between CD40 and the following molecules, which are identified by their Uniprot Accession Number in parentheses:

| | |
|---|---|
| CALR | (P27797); |
| ERP44 | (Q9BS26); |
| FBL | (P22087); |
| POLR2H | (P52434); |
| RFC5 | (P40937); |
| SGK1 | (O00141); |
| SLC30A7 | (Q8NEW0); |
| SLC39A7 | (Q92504); |
| TRAF2 | (Q5T1L5); |
| TRAF3 | (Q13114); |
| TRAF6 | (Q9Y4K3); |
| TXN | (Q5T937); |
| UGGT1 | (Q9NYU2); and |
| USP15 | (Q9Y4E8). |

For example, a CD40 "activity" includes an interaction with TRAF2. CD40/ TRAF2 interaction activates NF-κB and JNK. See Davies et al., Mol. Cell Biol. 25: 9806-19 (2005). This CD40 activity thus can be determined by CD40-dependent cellular NF-κB and JNK activation, relative to a reference.

As used herein, the terms "activate," "activates," and "activated" refer to an increase in a given measurable CD40 activity by at least 10% relative to a reference, for example, at least 10%, 25%, 50%, 75%, or even 100%, or more. A CD40 activity is "antagonized" if the CD40 activity is reduced by at least 10%, and in an exemplary embodiment, at least about 20%, 30%, 40%, 50%, 60%, 70%, 80%, 90%, 95%, 97%, or even 100% (i.e., no detectable activity), relative to the absence of the antagonist. For example, an antibody may antagonize some or all CD40 activity, while not activating CD40. For example, the antibody may not activate B cell proliferation. The antibody may not activate cytokine secretion by T cells, where the cytokine is at least one cytokine selected from the group consisting of IL-2, IL-6, IL-10, IL-13, TNF-α, and IFN-γ.

Variable domains may comprise one or more framework regions (FR) with the same amino acid sequence as a corresponding framework region encoded by a human germline antibody gene segment. Preferred framework sequences for use in the antibodies described herein are those that are structurally similar to the framework sequences used by antibodies described herein. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain up to 20, preferably conservative, amino acid substitutions as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al.).

Exemplary framework regions include but are not limited to those in Tables 5 and 6 below.

TABLE 5

| Heavy Framework Region | Sequence |
|---|---|
| FR1 | Amino acid residues 1-30 of any VH sequence in Table 8 (SEQ ID NOs: 53-75) or Table 10 (SEQ ID NOs: 4, 13, and 99-113) in the Examples |
| FR2 | Amino acid residues 36-49 of any VH sequence in Table 8 (SEQ ID NOs: 53-75) or Table 10 (SEQ ID NOs: 4, 13, and 99-113) in the Examples |

TABLE 5-continued

| Heavy Framework Region | Sequence |
|---|---|
| FR3 | Amino acid residues 67-98 of any VH sequence in Table 8 (SEQ ID NOs: 53-75) or Table 10 (SEQ ID NOs: 4, 13, and 99-113) in the Examples |
| FR4 | Amino acid residues 107-117 of any VH sequence in Table 8 (SEQ ID NOs: 53-75) or Table 10 (SEQ ID NOs: 4, 13, and 99-113) in the Examples |

TABLE 6

| Light Framework Region | Sequence |
|---|---|
| FR1 | Amino acid residues 1-23 of any VL sequence in Table 8 (SEQ ID NOs: 76-98) or Table 10 (SEQ ID NOs: 10, 16, and 114-116) in the Examples |
| FR2 | Amino acid residues 35-49 of any VL sequence in Table 8 (SEQ ID NOs: 76-98) or Table 10 (SEQ ID NOs: 10, 16, and 114-116) in the Examples |
| FR3 | Amino acid residues 57-88 of any VL sequence in Table 8 (SEQ ID NOs: 76-98) or Table 10 (SEQ ID NOs: 10, 16, and 114-116) in the Examples |
| FR4 | Amino acid residues 98-107 of any VL sequence in Table 8 (SEQ ID NOs: 76-98) or Table 10 (SEQ ID NOs: 10, 16, and 114-116) in the Examples |

A variant variable domain may differ from the variable domain of the humanized Y12XX-hz28, Y12XX-hz40, or Y12XX-hz42 sequence by up to 10 amino acids or any integral value between, where the variant variable domain specifically binds CD40. Alternatively, the variant variable domain may have at least 90% sequence identity (e.g., at least 92%, 95%, 98%, or 99% sequence identity) relative to the sequence of the humanized Y12XX-hz28, Y12XX-hz40, or Y12XX-hz42 sequence, respectively. Non-identical amino acid residues or amino acids that differ between two sequences may represent amino acid substitutions, additions, or deletions. Residues that differ between two sequences appear as non-identical positions, when the two sequences are aligned by an appropriate amino acid sequence alignment algorithm, such as BLAST® (a registered trademark of the U.S. National Library of Medicine).

Exemplary CD40 antibodies of the present invention can include an isolated antibody, or antigen binding portion thereof, that specifically binds to human CD40, wherein said antibody comprises a first polypeptide portion comprising a heavy chain variable region, and a second polypeptide portion comprising a light chain variable region, wherein:
said heavy chain variable region comprises one of (i) a CDR1 comprising SYWMH (SEQ ID NO: 1), a CDR2 comprising QINPTTGRSQYNEKFKT (SEQ ID NO: 2), a CDR3 comprising WGLQPFAY (SEQ ID NO: 3) and (ii) a CDR1 comprising SYWMH (SEQ ID NO: 1), a CDR2 comprising QINPSQGRSQYNEKFKT (SEQ ID NO: 12), a CDR3 comprising WGLQPFAY (SEQ ID NO: 3); and
said light chain variable region comprises a CDR1 comprising KASQDVSTAVA (SEQ ID NO: 7), a CDR2 comprising SASYRYT (SEQ ID NO: 8), and a CDR3 comprising QQHYSTPWT (SEQ ID NO: 9).

The isolated antibody or antigen binding portion thereof can antagonize one or more activities of CD40. The isolated antibody or antigen binding portion thereof can be a chimeric antibody. Exemplary heavy and light variable chains for a chimeric antibody are in Table 8 of the Examples. The isolated antibody or antigen binding portion thereof can be a humanized antibody. Exemplary humanized heavy and light variable chains are in Table 10 of the Examples. The isolated antibody or antigen binding portion thereof can comprise a human heavy chain constant region and a human light chain constant region.

Fc Domain and Constant Region

The carboxyl-terminal "half" of a heavy chain defines a constant region (Fc) and which is primarily responsible for effector function. As used herein, the term "Fc domain" refers to the constant region antibody sequences comprising CH2 and CH3 constant domains as delimited according to Kabat et al., Sequences of Immunological Interest, 5$^{th}$ ed., U.S. Dept. Health & Human Services, Washington, D.C. (1991). The Fc region may be derived from a human IgG. For instance, the Fc region may be derived from a human IgG1 or a human IgG4 Fc region. A heavy variable domain can be fused to an Fc domain. The carboxyl terminus of the variable domain may be linked or fused to the amino terminus of the Fc CH2 domain. Alternatively, the carboxyl terminus of the variable domain may be linked or fused to the amino terminus of a linker amino acid sequence, which itself is fused to the amino terminus of an Fc domain. Alternatively, the carboxyl terminus of the variable domain may be linked or fused to the amino terminus of a CH1 domain, which itself is fused to the Fc CH2 domain. Optionally, the protein may comprise the hinge region after the CH1 domain in whole or in part. Optionally an amino acid linker sequence is present between the variable domain and the Fc domain. The carboxyl terminus of the light variable domain may be linked or fused to the amino terminus of a CL domain.

An exemplary sequence for a heavy chain CH1 is amino acids 118-215 of SEQ ID NO: 5 (ASTKGPSVFPLAPSS-KSTSGGTAALGCLVKDYFPEPVTVSWNSGALTSGV-HTFPAVLQSSGLYSLSSVVTVPSSSLGTQTYICNVNH-KPSNTKVDKRV; SEQ ID NO: 18). An exemplary sequence for a light chain CL is amino acids 108-214 of SEQ ID NO: 11

(RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVT

KSFNRGEC; SEQ ID NO: 19).

The antibody can be a fusion antibody comprising a first variable domain that specifically binds human CD40, and a second domain comprising an Fc domain.

Exemplary Fc domains used in the fusion protein can include human IgG domains. Exemplary human IgG Fc domains include IgG4 Fc domain and IgG1 Fc domain. While human IgG heavy chain genes encode a C-terminal lysine, the lysine is often absent from endogenous antibodies as a result of cleavage in blood circulation. Antibodies having IgG heavy chains including a C-terminal lysine, when expressed in mammalian cell cultures, may also have variable levels of C-terminal lysine present (Cai et al, 2011, Biotechnol Bioeng. 108(2): 404-12). Accordingly, the C-terminal lysine of any IgG heavy chain Fc domain disclosed herein may be omitted.

The isolated antibody or antigen binding portion thereof described herein, can comprise an Fc domain which comprises an amino acid sequence of:

EPKSCDKTHTCPPCPAPELLGG(P/K)SVFLFPPKPKDTLMISRTPEVT

CVVVDVSHEDPEVKFNWYVDGVEVHNAKTKPREEQY(N/A)STYRVVSV

LTVLHQDWLNGKEYKCKVSNKALPAPIEKTISKAKGQPREPQVYTLPPS

R(D/E)E(L/M)TKNQVSLTCLVKGFYPSDIAVEWESNGQPENNYKTTP

PVLDSDGSFFLYSKLTVDKSRWQQGNVFSCSVMHEALHNHYTQKSLSLS

PG(K/not present) (Fc consensus; SEQ ID NO: 21).

The parenthetical notation indicates possible amino acid identities at the position. For instance, Kabat position 238 can be either Proline (P) or Lysine (K), which is notated as (P/K). Additional exemplary, non-limiting consensus sequences are SEQ ID NOs: 118-120.

The isolated antibody or antigen binding portion thereof described herein can comprise a human IgG1 Fc domain comprising a mutation at Kabat position 238 that reduces binding to Fc-gamma-receptors (FcγRs), wherein proline 238 (P238) is mutated to one of the residues selected from the group consisting of lysine (K), serine (S), alanine (A), arginine (R) and tryptophan (W), and wherein the antibody or antigen binding portion thereof has reduced FcγR binding. The isolated antibody or antigen binding portion thereof described herein can have P238 mutated to lysine in a human IgG1 Fc domain.

The isolated antibody or antigen binding portion thereof comprises an Fc domain which comprises an amino acid sequence selected from: SEQ ID NOs: 22-29.

Exemplary sequences comprising the IgG1 Fc domains above include: SEQ ID NO: 5, SEQ ID NO: 6, SEQ ID NO: 30, and SEQ ID NO: 31.

The isolated antibody or antigen binding portion thereof described herein can comprise a human IgG1 Fc domain comprising an alanine substituted at Kabat position 297. For example, the isolated antibody or antigen binding portion thereof comprises an Fc domain which comprises an amino acid sequence selected from: SEQ ID NOs: 32-39.

The isolated antibody or antigen binding portion described herein may comprise (1) a variable heavy chain (V$_H$) selected from Table 8 or Table 10 in the Examples, or the CDRs thereof, and/or (2) a variable light chain (V$_L$) selected from Table 8 or Table 10 in the Examples, or the CDRs thereof.

The isolated antibody or antigen binding portion thereof disclosed herein may comprise a heavy chain amino acid sequence selected from Vh-hz12 (SEQ ID NO: 13) and Vh-hz14 (SEQ ID NO: 4).

The isolated antibody or antigen binding portion thereof disclosed herein may comprise a light chain amino acid sequence selected from Vk-hz2 (SEQ ID NO: 10) and Vk-hz3 (SEQ ID NO: 16).

The isolated antibody or antigen binding portion thereof disclosed herein may be an antibody selected from the group consisting of:
  a) Y12XX-hz28-P238K having a heavy chain of SEQ ID NO: 5 or 6 and light chain of SEQ ID NO: 11;
  b) Y12XX-hz40-P238K having a heavy chain of SEQ ID NO: 14 or 15 and light chain of SEQ ID NO: 17; and
  c) Y12XX-hz42-P238K having a heavy chain of SEQ ID NO: 5 or 6 and light chain of SEQ ID NO: 17.

The antibody or antigen binding portion thereof disclosed herein, wherein the antigen binding portion is selected from the group consisting of Fv, Fab, F(ab')2, Fab', dsFv, scFv, sc(Fv)$_2$, diabodies, and scFv-Fc.

The antibody or antigen binding portion thereof disclosed herein can be an immunoconjugate, wherein the antibody or antigen-binding portion thereof is linked to a therapeutic agent.

The antibody or antigen binding portion thereof disclosed herein can be a bispecific antibody, wherein the antibody or antigen-binding portion thereof is linked to a second functional moiety having a different binding specificity than said antibody or antigen binding portion thereof.

The antibody or antigen binding portion thereof disclosed herein can further comprise an additional moiety.

The variable regions of the present antibodies may optionally be linked to the Fc domain by an "amino acid linker" or "linker." For example, the C-terminus of a variable heavy chain domain may be fused to the N-terminus of an amino acid linker, and an Fc domain may be fused to the C-terminus of the linker. Although amino acid linkers can be any length and consist of any combination of amino acids, the linker length may be relatively short (e.g., five or fewer amino acids) to reduce interactions between the linked domains. The amino acid composition of the linker also may be adjusted to reduce the number of amino acids with bulky side chains or amino acids likely to introduce secondary structure. Suitable amino acid linkers include, but are not limited to, those up to 3, 4, 5, 6, 7, 10, 15, 20, or 25 amino acids in length. Representative amino acid linker sequences include GGGGS (SEQ ID NO: 40), and a linker comprising 2, 3, 4, or 5 copies of GGGGS (SEQ ID NOs: 41 to 44, respectively). TABLE 7 lists suitable linker sequences for use in the present disclosure.

TABLE 7

| Representative Linker Sequences | |
| --- | --- |
| GGGGS | SEQ ID NO: 40 |
| (GGGGS)$_2$ | SEQ ID NO: 41 |
| (GGGGS)$_3$ | SEQ ID NO: 42 |
| (GGGGS)$_4$ | SEQ ID NO: 43 |
| (GGGGS)$_5$ | SEQ ID NO: 44 |
| AST | SEQ ID NO: 45 |
| TVAAPS | SEQ ID NO: 46 |
| TVA | SEQ ID NO: 47 |
| ASTSGPS | SEQ ID NO: 48 |

Antibody Preparation

The antibody can be produced and purified using ordinary skill in a suitable mammalian host cell line, such as CHO, 293, COS, NSO, and the like, followed by purification using one or a combination of methods, including protein A affinity chromatography, ion exchange, reverse phase techniques, or the like.

As well known in the art, multiple codons can encode the same amino acid. Nucleic acids encoding a protein sequence thus include nucleic acids having codon degeneracy. The polypeptide sequences disclosed herein can be encoded by a variety of nucleic acids. The genetic code is universal and well known. Nucleic acids encoding any polypeptide sequence disclosed herein can be readily conceived based on conventional knowledge in the art as well as optimized for production. While the possible number of nucleic acid sequence encoding a given polypeptide is large, given a standard table of the genetic code, and aided by a computer, the ordinarily skilled artisan can easily generate every possible combination of nucleic acid sequences that encode a given polypeptide.

A representative nucleic acid sequence encoding the Y12XX heavy chain variable domain of Y12XX-hz28 including a constant region CH1 and Fc domain IgG1-P238K is:

(SEQ ID NO: 49)
ATGAGGGCTTGGATCTTCTTTCTGCTCTGCCTGGCCGGGAGAGCGCTCGC

ACAGGTGCAGCTGGTGCAGTCTGGTGCCGAGGTCAAAAAGCCAGGCTCCA

GCGTGAAGGTGAGCTGCAAGGCCTCTGGCTACGCTTTCACCTCTTATTGG

ATGCACTGGGTGAGACAGGCTCCTGGACAGGGCCTGGAGTGGATGGGCCA

GATCAACCCAACCACCGGCAGAAGCCAGTACAATGAGAAGTTTAAGACCC

GCGTGACCATCACAGCCGACAAGTCCACCAGCACAGCTTATATGGAGCTG

TCTTCCCTGAGGTCCGAGGATACAGCCGTGTACTATTGCGCTCGGTGGGG

CCTGCAGCCTTTCGCTTACTGGGGCCAGGGCACCCTGGTGACAGTGAGCT

CTGCTAGCACCAAGGGCCCATCGGTCTTCCCCCTGGCACCCTCCTCCAAG

AGCACCTCTGGGGGCACAGCGGCCCTGGGCTGCCTGGTCAAGGACTACTT

CCCCGAACCGGTGACGGTGTCGTGGAACTCAGGCGCCCTGACCAGCGGCG

TGCACACCTTCCCGGCCGTCCTACAGTCCTCAGGACTCTACTCCCTCAGC

AGCGTGGTGACCGTGCCCTCCAGCAGCTTGGGCACCCAGACCTACATCTG

CAACGTGAATCACAAGCCCAGCAACACCAAGGTGGACAAGAGAGTTGAGC

CCAAATCTTGTGACAAAACTCACACATGCCCACCGTGCCCAGCACCTGAA

CTCCTGGGGGGAAAGTCAGTCTTCCTCTTCCCCCCAAAACCCAAGGACAC

CCTCATGATCTCCCGGACCCCTGAGGTCACATGCGTGGTGGTGGACGTGA

GCCACGAAGACCCTGAGGTCAAGTTCAACTGGTACGTGGACGGCGTGGAG

GTGCATAATGCCAAGACAAAGCCGCGGGAGGAGCAGTACAACAGCACGTA

CCGTGTGGTCAGCGTCCTCACCGTCCTGCACCAGGACTGGCTGAATGGCA

AGGAGTACAAGTGCAAGGTCTCCAACAAAGCCCTCCCAGCCCCCATCGAG

AAAACCATCTCCAAAGCCAAAGGGCAGCCCCGAGAACCACAGGTGTACAC

CCTGCCCCCATCCCGGGATGAGCTGACCAAGAACCAGGTCAGCCTGACCT

GCCTGGTCAAAGGCTTCTATCCCAGCGACATCGCCGTGGAGTGGGAGAGC

AATGGGCAGCCGGAGAACAACTACAAGACCACGCCTCCCGTGCTGGACTC

CGACGGCTCCTTCTTCCTCTACAGCAAGCTCACCGTGGACAAGAGCAGGT

GGCAGCAGGGGAACGTCTTCTCATGCTCCGTGATGCATGAGGCTCTGCAC

AACCACTACACGCAGAAGAGCCTCTCCCTGTCTCCGGGTTGA.

In this sequence, nucleotides 1-51 encode a signal peptide (optional), nucleotides 52-402 encode the heavy chain variable region in which nucleotides 141-155 encode CDR1, nucleotides 198-249 encode CDR2, and nucleotides 346-369 encode CDR3 of the Y12XX variable domain of the heavy chain. Nucleotides 403-696 encode a CH1 domain, and nucleotides 697-1399 encode IgG1-P238K. Nucleotides 1400-1402 are a stop codon.

A representative nucleic acid sequence encoding the Y12XX light chain variable domain of Y12XX-hz28 including a constant region CL is:

(SEQ ID NO: 50)
ATGAGGGCTTGGATCTTCTTTCTGCTCTGCCTGGCCGGGCGCGCCTTGGC

CGACATCCAGATGACCCAGTCCCCCTCCTTCCTGTCTGCCTCCGTGGGCG

ACAGAGTGACCATCACCTGTAAGGCTTCCCAGGATGTGAGCACAGCCGTG

GCTTGGTACCAGCAGAAGCCAGGCAAGGCCCCCAAGCTGCTGATCTATTC

CGCCTCTTACAGGTATACCGGCGTGCCCTCTCGGTTCTCCGGCAGCGGCT

CTGGCACAGACTTTACCCTGACAATCTCCAGCCTGCAGCCTGAGGATTTC

GCCACCTACTATTGCCAGCAGCACTACTCCACCCCATGGACATTTGGCGG

CGGCACCAAGGTGGAGATCAAGCGTACGGTGGCTGCACCATCTGTCTTCA

TCTTCCCGCCATCTGATGAGCAGTTGAAATCTGGAACTGCCTCTGTTGTG

TGCCTGCTGAATAACTTCTATCCCAGAGAGGCCAAAGTACAGTGGAAGGT

GGATAACGCCCTCCAATCGGGTAACTCCCAGGAGAGTGTCACAGAGCAGG

ACAGCAAGGACAGCACCTTACGCCTGCGAAGTCACCCATCAGGGCCTGAG

CTCGCCCGTCACAAAGAGCTTCAACAGGGGAGAGTGTTAG.

In this sequence, nucleotides 1-51 encode a signal peptide (optional), nucleotides 52-372 encode the light chain variable region in which nucleotides 121-153 encode CDR1, nucleotides 199-219 encode CDR2, and nucleotides 316-342 encode CDR3. Nucleotides 373-693 encode a CL. Nucleotides 694-696 are a stop codon The coding sequence for the heavy and/or light chain optionally may encode a signal peptide, such as MRAWIFFLLCLAGRALA (SEQ ID NO: 51), at the 5' end of the coding sequence. As described above, an exemplary nucleic acid coding sequence for this signal peptide is (SEQ ID NO: 52)
ATGAGGGCTTGGATCTTCTTTCTGCTCTGCCTGGCCGGGAGAGCGC

TCGCA.

Accordingly, a nucleic acid encoding an antibody disclosed herein is also contemplated. Such a nucleic acid may be inserted into a vector, such as a suitable expression vector, e.g., pHEN-1 (Hoogenboom et al. (1991) *Nucleic Acids Res.* 19: 4133-4137). Further provided is an isolated host cell comprising the vector and/or the nucleic acid.

The antibody of the disclosure can be produced and purified using only ordinary skill in any suitable mammalian host cell line, such as CHO (Chinese hamster ovary cells), 293 (human embryonic kidney 293 cells), COS cells, NSO cells, and the like, followed by purification using one or a combination of methods, including protein A affinity chromatography, ion exchange, reverse phase techniques, or the like.

Pharmaceutical Compositions and Methods of Treatment

A pharmaceutical composition comprises a therapeutically-effective amount of one or more antibodies and optionally a pharmaceutically acceptable carrier. Pharmaceutically acceptable carriers include, for example, water, saline, phosphate buffered saline, dextrose, glycerol, ethanol and the like, as well as combinations thereof. Pharmaceutically acceptable carriers can further comprise minor amounts of auxiliary substances, such as wetting or emulsifying agents, preservatives, or buffers that enhance the shelf-life or effectiveness of the fusion protein. The compositions can be formulated to provide quick, sustained, or delayed release of the active ingredient(s) after administration. Suitable pharmaceutical compositions and processes for preparing them are known in the art. See, e.g., Remington, THE SCIENCE AND PRACTICE OF PHARMACY, A. Gennaro, et al., eds., 21st ed., Mack Publishing Co. (2005).

The pharmaceutical composition may be administered alone or in combination therapy, (i.e., simultaneously or sequentially) with an immunosuppressive/immunomodulatory and/or anti-inflammatory agent. An exemplary type of agent is a cytotoxic T lymphocyte-associated protein 4 (CTLA4) mutant molecule. An exemplary CTLA4 mutant molecule is L104EA29Y-Ig (belatacept) which is a modified CTLA4-Ig. Different immune diseases can require use of specific auxiliary compounds useful for treating immune diseases, which can be determined on a patient-to-patient basis. For example, the pharmaceutical composition may be administered in combination with one or more suitable adjuvants, e.g., cytokines (IL-10 and IL-13, for example) or other immune stimulators, e.g., chemokines, tumor-associated antigens, and peptides. Suitable adjuvants are known in the art.

A method of treating an immune disease in a patient in need of such treatment may comprise administering to the patient a therapeutically effective amount of the antibody, or antigen binding portion thereof, as described herein. Further provided is a method of treating or preventing an autoimmune or inflammatory disease in a patient in need of such treatment may comprise administering to the patient a therapeutically effective amount of the antibody, or antigen binding portion thereof, as described herein. Also provided is the use of an antibody, or antigen binding portion thereof, of the disclosure, or a pharmaceutically acceptable salt thereof, for treating an immune disease in a patient in need of such treatment and/or for treating or preventing an autoimmune or inflammatory disease in a patient in need of such treatment, that may comprise administering to the patient a therapeutically effective amount of the antibody, or antigen binding portion thereof. Antagonizing CD40-mediated T cell activation could inhibit undesired T cell responses occurring during autoimmunity, transplant rejection, or allergic responses, for example. Inhibiting CD40-mediated T cell activation could moderate the progression and/or severity of these diseases.

The use of an antibody, or antigen binding portion thereof, of the disclosure, or a pharmaceutically acceptable salt thereof, in the preparation of a medicament for treatment of an immune disease and/or for treating or preventing an autoimmune or inflammatory disease in a patient in a patient in need of such treatment, is also provided. The medicament can, for example, be administered in combination with an immunosuppressive/immunomodulatory and/or anti-inflammatory agent.

As used herein, a "patient" means an animal, e.g., mammal, including a human. The patient may be diagnosed with an immune disease. "Treatment" or "treat" or "treating" refers to the process involving alleviating the progression or severity of a symptom, disorder, condition, or disease. An "immune disease" refers to any disease associated with the development of an immune reaction in an individual, including a cellular and/or a humoral immune reaction. Examples of immune diseases include, but are not limited to, inflammation, allergy, autoimmune disease, or graft-related disease. Thus, the patient may be diagnosed with an autoimmune disease or inflammatory disease. An "autoimmune disease" refers to any disease associated with the development of an autoimmune reaction in an individual, including a cellular and/or a humoral immune reaction. An example of an autoimmune disease is inflammatory bowel disease (IBD), including, but not limited to ulcerative colitis and Crohn's disease. Other autoimmune diseases include systemic lupus erythematosus, multiple sclerosis, rheumatoid arthritis, diabetes, psoriasis, scleroderma, and atherosclerosis. Graft-related diseases include graft versus host disease (GVHD), acute transplantation rejection, and chronic transplantation rejection.

Diseases that can be treated by administering the antibody of the disclosure may be selected from the group consisting of Addison's disease, allergies, anaphylaxis, ankylosing spondylitis, asthma, atherosclerosis, atopic allergy, autoimmune diseases of the ear, autoimmune diseases of the eye, autoimmune hepatitis, autoimmune parotitis, bronchial asthma, coronary heart disease, Crohn's disease, diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products (e.g., Factor VII in hemophiliacs), lupus nephritis, systemic lupus erythematosus, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, vasculitis, and ulcerative colitis.

The pharmaceutical composition may be administered alone or as a combination therapy, (i.e., simultaneously or sequentially) with an immunosuppressive/immunomodulatory and/or anti-inflammatory agent. Different immune diseases can require use of specific auxiliary compounds useful for treating immune diseases, which can be determined on a patient-to-patient basis. For example, the pharmaceutical composition may be administered in combination with one or more suitable adjuvants, e.g., cytokines (IL-10 and IL-13, for example) or other immune stimulators, e.g., chemokines, tumor-associated antigens, and peptides. Suitable adjuvants are known in the art.

Any suitable method or route can be used to administer the antibody, or antigen binding portion thereof, or the pharmaceutical composition. Routes of administration include, for example, intravenous, intraperitoneal, subcutaneous, or intramuscular administration. A therapeutically effective dose of administered antibody depends on numerous factors, including, for example, the type and severity of the immune disease being treated, the use of combination therapy, the route of administration of the antibody, or antigen binding portion thereof, or pharmaceutical composition, and the weight of the patient. A non-limiting range for a therapeutically effective amount of a domain antibody is 0.1-20 milligram/kilogram (mg/kg), and in an aspect, 1-10 mg/kg, relative to the body weight of the patient.

Kits

A kit useful for treating an immune disease in a human patient is provided. A kit useful for treating or preventing an autoimmune disease or inflammatory disease in a human patient is also provided. The kit can comprise (a) a dose of an antibody, or antigen binding portion thereof, of the present disclosure and (b) instructional material for using the antibody, or antigen binding portion thereof, in the method of treating an immune disease, or for using the antibody, or antigen binding portion thereof, in the method of treating or preventing an autoimmune or inflammatory disease, in a patient.

"Instructional material," as that term is used herein, includes a publication, a recording, a diagram, or any other medium of expression, which can be used to communicate the usefulness of the composition and/or compound of the invention in a kit. The instructional material of the kit may, for example, be affixed to a container that contains the compound and/or composition of the invention or be shipped together with a container, which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

EXAMPLES

Example 1: Binding of Mouse Anti-Human CD40 Antibodies to Human CD40

Mouse anti-human-CD40 antibodies were generated and were tested for binding to human CD40 by surface plasmon resonance (SPR). The Vh and Vk sequences for each antibody are shown in Table 8.

TABLE 8

| Mouse anti-human-CD40 variable heavy and light sequences | | |
|---|---|---|
| ID | VH Sequence | VL Sequence |
| ADX_Y1060.ZZ0-1 | ADX_Y1060.ZZ0-1-Vh<br>QVQLVQSGAEVKKPGASVKVSCKASG<br>YTFTGYYMHWVRQAPGQGLEWMGWIN<br>PDSGGTNYAQKFQGRVTMTRDTSIST<br>AYMELNRLRSDDTAVYYCARDQPLGY<br>CTNGVCSYFDYWGQGTLVTVSS<br>(SEQ ID NO: 53) | ADX_Y1060.ZZ0-1-Vk<br>DIQMTQSPSSVSASVGDRVTITCRASQ<br>GIYSWLAWYQQKPGKAPNLLIYTASTL<br>QSGVPSRFSGSGSGTDFTLTISSLQPE<br>DFATYYCQQANIFPLTFGGGTKVEIK<br>(SEQ ID NO: 76) |
| ADX_Y1072.ZZ0-1 | ADX_Y1072.ZZ0-1-Vh<br>QVQFQQSGAELARPGASVKLSCKASG<br>YTFTSYWMQWVKQRPGQGLEWIGTIY<br>PGDGDSRYNQKFKGKALLTADKSSSI<br>AYMQLNSLASEDSAVYFCARFSLYDG<br>YPYYFDYWGQGTTLTVSS<br>(SEQ ID NO: 54) | ADX_Y1072.ZZ0-1-Vk<br>DVVMTQTPLSLPVSLGDQASISCRSSQ<br>SLVHRNGNTYLHWYLQKPGQSPKLLIY<br>RVSNRFSGVPDRFSGSGSGTDFTLKIS<br>RVEAEDLGIYFCSQSTHFPYTFGGGTK<br>LEIK<br>(SEQ ID NO: 77) |
| ADX_Y1234.ZZ0-1 | ADX_Y1234.ZZ0-1-Vh<br>EVQLVESGGGLVKPGGSLKLSCAASG<br>FAFSSYDMSWVRQTPEKRLEWVAYIN<br>SGVGNTYYPDTVKGRFTISRDNAKNT<br>LYLQMSSLKSEDTAMYYCARHGNYAW<br>FAYWGQGTLVTVSA<br>(SEQ ID NO: 55) | ADX_Y1234.ZZ0-1-Vk<br>DILLTQSPAILSVSPGERVSFSCRASQ<br>SIGTSIHWYQQRTIGSPRLLIKYASES<br>ISGIPSRFSGSGSGTDFTLSINSVESE<br>DIADYYCQQINSWPLTFGAGTKLELK<br>(SEQ ID NO: 78) |
| ADX_Y1236.ZZ0-1 | ADX_Y1236.ZZ0-1-Vh<br>DVQLVESGGGLVQPGGSRKLSCAASG<br>FTFSSFGMHWVRQAPEKGLEWVAYIS<br>SGSSTIYYADTVKGRFTISRDNPKNT<br>LFLQMTSLRSEDTAMYYCARYGNYAM<br>DYWGQGTSVTVSS<br>(SEQ ID NO: 56) | ADX_Y1236.ZZ0-1-Vk<br>DIVMTQSQKFMSTSVGDRISITCKASQ<br>NVRTAVAWYQQKPGQSPKALIYLASNR<br>HTGVPARFSGSGSGTSYSLTISRMEAE<br>DAATYYCQQRSSYPLTFGAGTKLELK<br>(SEQ ID NO: 79) |
| ADX_Y1238.ZZ0-1 | ADX_Y1238.ZZ0-1-Vh<br>QVQLQQSGAELVRPGTSVKVSCKASG<br>YAFTNYLIEWVKQRPGQGLEWIGVIN<br>PGSGGTNYNEKFKGKATLTADKSSST<br>AYMQLSSLTSDDSAVYFCARSQLGRR<br>FDYWGQGTTLTVSS<br>SEQ ID NO: 57) | ADX_Y1238.ZZ0-1-Vk<br>DIVMTQSHKFMSTSVGDRVSITCKASQ<br>DVRTGVAWYQQKPGQSPKLLIYSASYR<br>NTGVPDRFTGSRSGTDFTFTISSVQAE<br>DLAVYYCQQHYSPPYTFGGGTKLEIK<br>(SEQ ID NO: 80) |
| ADX_Y1241.ZZ0-1 | ADX_Y1241.ZZ0-1-Vh<br>EFQLQQSGPELVKPGASVKMSCKASG<br>YTFTNYIIQWVKQPGQGLEWIGYIN<br>PYSSETNYNEKFKGKATLTSDKSSST<br>AYMELSSLTSEDSAIYFCARDLIGNY<br>WGQGTTLTVSS<br>(SEQ ID NO: 58) | ADX_Y1241.ZZ0-1-Vk<br>DIVMTQSHKFMSTSVGDRVSITCKASQ<br>DVGTAVAWYQQKPGQSPKLLIYWASTR<br>HTGVPDRFTGSGSGTDFTLTISNVQSE<br>DLADYFCQQYSSYPLTFGAGTKLELK<br>(SEQ ID NO: 81) |
| ADX_Y1242.ZZ0-1 | ADX_Y1242.ZZ0-1-Vh<br>EFQLQQSGPELVKPGASVKMSCKASG<br>YSFTSYVMHWVKQPGQALEWIGYIN<br>PSNDGSEYNERFKGKATLTSDKSSTT<br>AYMELSSLTSEDSAVYYCARWAPYPF<br>AYWGQGTLVTVSA<br>(SEQ ID NO: 59) | ADX_Y1242.ZZ0-1-Vk<br>DIVMTQSHKFMSTSVGDRVSITCKASQ<br>DVSTAVAWYQQKPGQSPKLLIYSASYR<br>YTGVPDRFTGSGSGTDFTFTISSVQAE<br>DLAVYYCQQHYSTPYTFGGGTKLEIK<br>(SEQ ID NO: 82) |
| ADX_Y1249.ZZ0-1 | ADX_Y1249.ZZ0-1-Vh<br>QVQLQQSGAELARPGASVKMSCKASG<br>YTFTSYTMHWVKQRPGQGLEWIGYID | ADX_Y1249.ZZ0-1-Vk<br>DIVMTQSHKFMSTSVGDRVSITCKASQ<br>DVSTAVAWYQQKPGQSPKLLIYSASYR |

TABLE 8-continued

Mouse anti-human-CD40 variable heavy and light sequences

| ID | VH Sequence | VL Sequence |
|---|---|---|
| | PSSHYTNYNQKFKGTATLTADKSSNT AYMQLSSLTSEDSAVYYCARDYRYAY WYFDVWGAGTTLTVSS (SEQ ID NO: 60) | YTGVPDRFTGSGSGTDFTFTISSVQAE DLAVYYCQQHYSTPWTFGGGTKLEIK (SEQ ID NO: 83) |
| ADX_Y1256.ZZ0-1 | ADX_Y1256.ZZ0-1-Vh QVQLQQSGAELAKPGSSVKMSCKASG YAFTSYWMHWVKQRPGQGLEWIGYIN PTTGYSAYNQKFKDKATLTADKSSST AYLQLTSLTSEDSAVYFCSRWGLPPF AYWGQGTLVTVSA (SEQ ID NO: 61) | ADX_Y1256.ZZ0-1-Vk DIVMTQSHKFMSTSVGDRVSITCKASQ DVSTAVAWYQQKPGQSPKLLIYSASYR YTGVPDRFTGSGSGTDFTFTISSVQAE DLAVYYCQQHYSTPWTFGGGTKLEIK (SEQ ID NO: 84) |
| ADX_Y1257.ZZ0-1 | ADX_Y1257.ZZ0-1-Vh QVQLQQSGAELAKPGSSVKMSCKASG YAFTSYWMHWVKQRPGQGLEWIGYIN PTTGYSAYNQKFKAKTTLTADKSSST AYMQLTSLTFEDSAVYFCSRWGLPPF AYWGQGTLVTVSA (SEQ ID NO: 62) | ADX_Y1257.ZZ0-1-Vk DIVMTQSHKFMSTSVGDRVSITCKASQ DVSTAVAWYQQKPGQSPKLLIYSASYR YTGVPDRFTGSGSGTDFTFTISSVQAE DLAVYYCQQHYSTPWTFGGGTKLEIK (SEQ ID NO: 85) |
| ADX_Y1258.ZZ0-1 | ADX_Y1258.ZZ0-1-Vh QVQLQQSGAELAKPGSSVKMSCKASG YAFTSYWMHWIKQRPGQGLEWIGFIN PTTGYSEYNQKFKDKATLTADKSSST AYMQLNSLTSEDSAVYFCARWGLPPF AYWGQGTLVTVSA (SEQ ID NO: 63) | ADX_Y1258.ZZ0-1-Vk DIVMTQSHKFMSTSVGDRVSITCKASQ DVSTAVAWYQQKPGQSPKLLIYSASYR YTGVPDRFTGSGSGTDFTFTISSVQAE DLAVYYCQQHYSTPWTFGGGTKLEIK (SEQ ID NO: 86) |
| ADX_Y1259.ZZ0-1 | ADX_Y1259.ZZ0-1-Vh QVQLQQSGAELAKPGASVKMSCKTSG YSFTSYWMHWIKQRPGQGLEWIGFIN PTTGYTEYNQKFKDKATLTADKSSST AYMQLSSLSSEDSAVYYCSRWGLPPF AYWGQGTLVTVSA (SEQ ID NO: 64) | ADX_Y1259.ZZ0-1-Vk DIVMTQSHKFMSTSVGDRVSITCKASQ DVSTAVAWYQQKPGQSPKLLIYSASYR YTGVPDRFTGSGSGTDFTFTISSVQAE DLAVYYCQQHYSTPWTFGGGTKLEIK (SEQ ID NO: 87) |
| ADX_Y1260.ZZ0-1 | ADX_Y1260.ZZ0-1-Vh QVQLQQSGAELTKPGASVKMSCKASG YSFTSYWMHWVKQRPGQGLEWIGSIN PSTGYTEDNQKFKDKATLTADKSSTT AYMQLSSLTSEDSAVYYCARWGLPPF AYWGQGTLVTVSA (SEQ ID NO: 65) | ADX_Y1260.ZZ0-1-Vk DIVMTQSHKFMSTSVGDRVSITCKASQ DVSTAVAWYQQKPGQSPKLLIYSASYR YTGVPDRFTGSGSGTDFTFTISSVQAE DLAVYYCQQHYSTPWTFGGGTKLEIK (SEQ ID NO: 88) |
| ADX_Y1261.ZZ0-1 | ADX_Y1261.ZZ0-1-Vh QVQLQQSGAERAKPGASVKMSCKASG YSFTSYWMHWIKQRPGQGLEWIGFIN PNTGHTDYNQKFKDKATLTADKSSST AYMQLSSLTSEDSAVYFCSRWGLPPF AYWGQGTLVTVSA (SEQ ID NO: 66) | ADX_Y1261.ZZ0-1-Vk DIVMTQSHKFMSTSVGDRVSITCKASQ DVSTAVAWYQQKPGQSPKLLIYSASYR YTGVPDRFTGSGSGTDFTFTISSVQAE DLAVYYCQQHYSTPWTFGGGTKLEIK (SEQ ID NO: 89) |
| ADX_Y1262.ZZ0-1 | ADX_Y1262.ZZ0-1-Vh QVQLQQSGAELAKPGSSVKMSCKASG YAFTSYWMHWVKQRPGQGLEWIGYIN PTTGYSAYNQKFKDKATLTADKSSST AYMQLNSLTSEDSAVYYCARWDPRPF AYWGQGTLVTVSA (SEQ ID NO: 67) | ADX_Y1262.ZZ0-1-Vk DIVMTQSHKFMSTSVGDRVSITCKASQ DVSTAVAWYQQKPGQSPKLLIYSASYR YTGVPDRFTGSGYGTDFTFTISSVQAE DLAVYYCQQHYSTPWTFGGGTKLEIK (SEQ ID NO: 90) |
| ADX_Y1263.ZZ0-1 | ADX_Y1263.ZZ0-1-Vh QVQLQQSGAELAKPGTSVKMSCKASG YSFTSYWVHWVKERPGQGLEWIGHTN PNTGYTEYNQKFKDKATLTVDRSSST AYMQLNSLTSEDSAVYYCARWDPRPF AYWGQGTLVTVSA (SEQ ID NO: 68) | ADX_Y1263.ZZ0-1-Vk DIVMTQSHKFMSTSVGDRVSITCKASQ DVSTAVAWYQQKPGQSPKLLIYSASYR YTGVPDRFTGSGSGTDFTFTISSVQAE DLAVYYCQQHYSTPWTFGGGTKLEIK (SEQ ID NO: 91) |
| ADX_Y1264.ZZ0-1 | ADX_Y1264.ZZ0-1-Vh EVQLQQSGTVLARPGASVKMSCRASG YSFSSYWMHWVKQRPGQGLEWIGSIN PGNSDAFYNQQFKGKAKLTAVTSAST AYMELSSLTNEDSAVYYCTRWGLPPF AYWGQGTLVTVSA (SEQ ID NO: 69) | ADX_Y1264.ZZ0-1-Vk DIVMTQSHKFMSTSVGDRVSITCKASQ DVSTAVAWYQQKPGQSPKLLIYSASYR YTGVPDRFTGSGSGTDFTFTISSVQAE DLAVYYCHQHYSTPWTFGGGTKLEIK (SEQ ID NO: 92) |

TABLE 8-continued

Mouse anti-human-CD40 variable heavy and light sequences

| ID | VH Sequence | VL Sequence |
|---|---|---|
| ADX_Y1265.ZZ0-1 | ADX_Y1265.ZZ0-1-Vh<br>EVQLQQSGTVLAGPGASVKMSCKASG<br>YSFTSYWMHWVKQRPGQDLEWIGTIN<br>PGKGDSNYNQKFKGKAKLTAVTSAST<br>AYMELSSLTNEDSAVYYCTRWGLPPF<br>AYWGQGTLVTVSA<br>(SEQ ID NO: 70) | ADX_Y1265.ZZ0-1-Vk<br>DIVMTQSHKFMSTSVGDRVSITCKASQ<br>DVSTAVAWYQQKPGQSPKLLIYSASYR<br>YTGVPDRFTGSGSGTDFTFTISSVQAE<br>DLAVYYCQQHYSTPWTFGGGTKLEIK<br>(SEQ ID NO: 93) |
| ADX_Y1266.ZZ0-1 | ADX_Y1266.ZZ0-1-Vh<br>QVQLQQPGAELVKPGASVRLSCKASG<br>YSFTSYWMHWVKQRPGQGLEWIGQIN<br>PSNGRTQYNEKFKSMATLTVDKSSST<br>AYIQLSSLTSEDSAVYYCARWGLQPF<br>AYWGQGTLVTVSA<br>(SEQ ID NO: 71) | ADX_Y1266.ZZ0-1-Vk<br>DIVMTQSHKFMSTSVGDRVSITCKASQ<br>DVSTAVAWYQQKPGQSPKLLIYSASYR<br>YTGVPDRFTGSGSGTDFTFTISSVQAE<br>DLAVYYCQQHYSTPWTFGGGTKLEIK<br>(SEQ ID NO: 94) |
| ADX_Y1267.ZZ0-1 | ADX_Y1267.ZZ0-1-Vh<br>QVQLQQPGAELVKPGASVRLSCEASG<br>YSFTSYWMHWVKQRPGQGLEWIGQIN<br>PSNGRTQYNEKFKSMATLTVDKSSST<br>AYIQLNSLTSEDSAVYYCARWGLQPF<br>AYWGQGTLVTVSA<br>(SEQ ID NO: 72) | ADX_Y1267.ZZ0-1-Vk<br>DIVMTQSHKFMSTSVGDRVSITCKASQ<br>DVSTAVAWYQQKPGQSPKLLIYSASYR<br>YTGVPDRFTGSGSGTDFTFTISSVQAE<br>DLAVYYCLQHYTTPWTFGGGTKLEIK<br>(SEQ ID NO: 95) |
| ADX_Y1268.ZZ0-1 | ADX_Y1268.ZZ0-1-Vh<br>QVQLQQPGAELVKPGASVRLSCKASG<br>YAFTSYWMHWVKQRPGQGLEWIGQIN<br>PSNGRSQYNEKFKTMATLTVDKSSST<br>AYIQLSSLTSEDSAVYYCARWGLQPF<br>AYWGQGTLVTVSA<br>(SEQ ID NO: 73) | ADX_Y1268.ZZ0-1-Vk<br>DIVMTQSHKFMSTSVGDRVSITCKASQ<br>DVSTAVAWYQQKPGQSPKLLIYSASYR<br>YTGVPDRFTGSGSGTDFTFTISSVQAE<br>DLAVYYCQQHYSTPWTFGGGTKLEIK<br>(SEQ ID NO: 96) |
| ADX_Y1269.ZZ0-1 | ADX_Y1269.ZZ0-1-Vh<br>QVQLQQSGAELPRPGASVKMSCKASG<br>YTFTDYTVHWVKQRPGQGLEWIGYIN<br>PSSSYTSYDQKFKDKATVTADKSSST<br>AYMQLSSLTSEDSAVYYCARRTMYWY<br>FDIWGAGTTVTVSS<br>(SEQ ID NO: 74) | ADX_Y1269.ZZ0-1-Vk<br>DIVMTQSHKFMSTSVGDRVSITCKASQ<br>DVSPNVAWYQQKPGQSPKLLIYSTSYR<br>YTGVPDRFTGSRSGTDFTFTISSVQAE<br>DLAIYYCQQHYSTPLTFGAGTKLELK<br>(SEQ ID NO: 97) |
| ADX_Y1297.ZZ0-1 | ADX_Y1297.ZZ0-1-Vh<br>QVQLQQSGAELVKPGASVKLSCKASG<br>YTFTSYWMHWVKQRPGQGLEWIGEID<br>PSDSYTNYNQNFKGKATLTVDKSSST<br>AYMQLSSLTSEDSAVYYCARETYYYG<br>SRFPYWGQGTLVTVSA<br>(SEQ ID NO: 75) | ADX_Y1297.ZZ0-1-Vk<br>DIVMTQSHKFMSTSVGDRVSVTCKASQ<br>NVRINVAWYQQKPGQSPKALIYSASYR<br>YSGVPDRFTGSGSGTDFTLTITNVQSE<br>DLAEYFCQQYNTYPLTFGAGTKLELK<br>(SEQ ID NO: 98) |

The CD40 kinetic and affinity data for human-CD40 monomer binding to mouse anti-human CD40 antibodies captured on a protein A sensor chip surface were assessed by SPR. The data are shown in Table 9. The data shown are for a single concentration of CD40 analyte (1 μM) and are therefore reported as apparent (app) values.

TABLE 9

SPR kinetic/affinity data

| Antibody | $ka,_{app}$ (1/Ms) | $kd,_{app}$ (1/s) | $KD_{app}$ (M) |
|---|---|---|---|
| ADX_Y1072.ZZ0-1 | 7.7E+04 | 9.2E-03 | 1.2E-07 |
| ADX_Y1238.ZZ0-1 | 5.5E+04 | 1.2E-04 | 2.2E-09 |
| ADX_Y1258.ZZ0-1 | 1.7E+04 | 1.3E-04 | 7.9E-09 |
| ADX_Y1260.ZZ0-1 | 5.2E+04 | 2.1E-04 | 4.0E-09 |
| ADX_Y1262.ZZ0-1 | 3.7E+05 | 2.5E-03 | 6.6E-09 |
| ADX_Y1264.ZZ0-1 | 1.4E+04 | 2.3E-04 | 1.7E-08 |
| ADX_Y1267.ZZ0-1 | 3.7E+05 | 4.1E-04 | 1.1E-09 |
| ADX_Y1268.ZZ0-1 | 3.2E+05 | 4.6E-04 | 1.4E-09 |

Based on the SPR data and sequence data, three antibodies, ADX_Y1258. ZZO-1, ADX_Y1262. ZZO-1, and ADX_Y1268. ZZO-1, were selected for humanization.

Example 2: Humanization and Selection of Humanized Variants of Y12XX

Humanization background/procedure is as discussed in section "II. Engineered and Modified Antibodies" in WO2017004006, which is incorporated herein by reference in its entirety. Based on this analysis, nine (9) humanized Vh sequences (Vh-hz1, Vh-hz2, Vh-hz3, Vh-hz4, Vh-hz5, Vh-hz6, Vh-hz9, Vh-hz10, and Vh-hz11) and three (3) humanized $V_κ$ sequences (Vk-hz1, Vk-hz2, and Vk-hz3), were selected for testing. In addition, five (5) humanized Vh sequences (Vh-hz7, Vh-hz8, Vh-hz12, Vh-hz13, and Vh-hz14) were designed to contain mutations intended to reduce chemical liability risk designed. The mutations include D100Q (Y1262_IGHV1.6908-D100Q) and P101A (Y1262_IGHV1.6908-P101A) mutations to mitigate potential hydrolysis risk in Y1262_IGHV1.6908. The mutations also include N55Q (Y1268_IGHV1.6908-N55Q), G56A (Y1268_IGHV1.6908-G56A), and the S54T-N55T double mutation (Y1268_IGHV1.6908-S54T-N55T) to mitigate potential deamidation risk in Y1268_IGHV1.6908. The S54T-N55T double mutation was designed based on the corresponding amino acid residues found at these positions in ADX_Y1262. ZZO-1-Vh. See Table 10.

The sequences for these variants are shown in Table 10.

TABLE 10

| ID | Variable Hz # | SEQ ID NO: | Sequence |
|---|---|---|---|
| Y1258-Vh | Vh-C1 | 99 | QVQLQQSGAELAKPGSSVKMSCKASGYAFTSYWMHWI KQRPGQGLEWIGFINPTTGYSEYNQKFKDKATLTADK SSSTAYMQLNSLTSEDSAVYFCARWGLPPFAYWGQGT LVTVSA |
| Y1258_IGHV1.6908-Vh | Vh-hz1 | 100 | QVQLVQSGAEVKKPGSSVKVSCKASGYAFTSYWMHWV RQAPGQGLEWMGFINPTTGYSEYNQKFKDRVTITADK STSTAYMELSSLRSEDTAVYYCARWGLPPFAYWGQGT LVTVSS |
| Y1258_IGHV1.6908_A40R-Vh | Vh-hz2 | 101 | QVQLVQSGAEVKKPGSSVKVSCKASGYAFTSYWMHWV RQRPGQGLEWMGFINPTTGYSEYNQKFKDRVTITADK STSTAYMELSSLRSEDTAVYYCARWGLPPFAYWGQGT LVTVSS |
| Y1258_IGHV1.6908_A40R-M48I-S84N-Vh | Vh-hz3 | 102 | QVQLVQSGAEVKKPGSSVKVSCKASGYAFTSYWMHWV RQRPGQGLEWIGFINPTTGYSEYNQKFKDRVTITADK STSTAYMELNSLRSEDTAVYYCARWGLPPFAYWGQGT LVTVSS |
| Y1262-Vh | Vh-C2 | 103 | QVQLQQSGAELAKPGSSVKMSCKASGYAFTSYWMHWV KQRPGQGLEWIGYINPTTGYSAYNQKFKDKATLTADK SSSTAYMQLNSLTSEDSAVYYCARWDPRPFAYWGQGT LVTVSA |
| Y1262_IGHV1.6908-Vh | Vh-hz4 | 104 | QVQLVQSGAEVKKPGSSVKVSCKASGYAFTSYWMHWV RQAPGQGLEWMGYINPTTGYSAYNQKFKDKATLTADK STSTAYMELSSLRSEDTAVYYCARWDPRPFAYWGQGT LVTVSS |
| Y1262_IGHV1.6908_A40R-Vh | Vh-hz5 | 105 | QVQLVQSGAEVKKPGSSVKVSCKASGYAFTSYWMHWV RQRPGQGLEWMGYINPTTGYSAYNQKFKDKATLTADK STSTAYMELSSLRSEDTAVYYCARWDPRPFAYWGQGT LVTVSS |
| Y1262_IGHV1.6908_A40R-M48I-S84N-Vh | Vh-hz6 | 106 | QVQLVQSGAEVKKPGSSVKVSCKASGYAFTSYWMHWV RQRPGQGLEWIGYINPTTGYSAYNQKFKDKATLTADK STSTAYMELNSLRSEDTAVYYCARWDPRPFAYWGQGT LVTVSS |
| Y1262_IGHV1.6908-D100Q-Vh | Vh-hz7 | 107 | QVQLVQSGAEVKKPGSSVKVSCKASGYAFTSYWMHWV RQAPGQGLEWMGYINPTTGYSAYNQKFKDKATLTADK STSTAYMELSSLRSEDTAVYYCARWQPRPFAYWGQGT LVTVSS |
| Y1262_IGHV1.6908-P101A-Vh | Vh-hz8 | 108 | QVQLVQSGAEVKKPGSSVKVSCKASGYAFTSYWMHWV RQAPGQGLEWMGYINPTTGYSAYNQKFKDKATLTADK STSTAYMELSSLRSEDTAVYYCARWDARPFAYWGQGT LVTVSS |
| Y1268-Vh | Vh-C3 | 109 | QVQLQQPGAELVKPGASVRLSCKASGYAFTSYWMHWV KQRPGQGLEWIGQINPSNGRSQYNEKFKTMATLTVDK SSSTAYIQLSSLTSEDSAVYYCARWGLQPPFAYWGQGT LVTVSA |
| Y1268_IGHV1.6908-Vh | Vh-hz9 | 110 | QVQLVQSGAEVKKPGSSVKVSCKASGYAFTSYWMHWV RQAPGQGLEWMGQINPSNGRSQYNEKFKTRVTITADK STSTAYMELSSLRSEDTAVYYCARWGLQPPFAYWGQGT LVTVSS |
| Y1268_IGHV1.6908_A40R-Vh | Vh-hz10 | 111 | QVQLVQSGAEVKKPGSSVKVSCKASGYAFTSYWMHWV RQRPGQGLEWMGQINPSNGRSQYNEKFKTRVTITADK STSTAYMELSSLRSEDTAVYYCARWGLQPPFAYWGQGT LVTVSS |
| Y1268_IGHV1.6908_A40R-M48I-Vh | Vh-hz11 | 112 | QVQLVQSGAEVKKPGSSVKVSCKASGYAFTSYWMHWV RQRPGQGLEWIGQINPSNGRSQYNEKFKTRVTITADK STSTAYMELSSLRSEDTAVYYCARWGLQPPFAYWGQGT LVTVSS |

TABLE 10-continued

| ID | Variable Hz # | SEQ ID NO: | Sequence |
|---|---|---|---|
| Y1268_IGHV1.6908-N55Q-Vh | Vh-hz12 | 13 | QVQLVQSGAEVKKPGSSVKVSCKASGYAFTSYWMHWV RQAPGQGLEWMGQINPSQGRSQYNEKFKTRVTITADK STSTAYMELSSLRSEDTAVYYCARWGLQPFAYWGQGT LVTVSS |
| Y1268_IGHV1.6908-G56A-Vh | Vh-hz13 | 113 | QVQLVQSGAEVKKPGSSVKVSCKASGYAFTSYWMHWV RQAPGQGLEWMGQINPSNARSQYNEKFKTRVTITADK STSTAYMELSSLRSEDTAVYYCARWGLQPFAYWGQGT LVTVSS |
| Y1268_IGHV1.6908-S54T-N55T-Vh | Vh-hz14 | 4 | QVQLVQSGAEVKKPGSSVKVSCKASGYAFTSYWMHWV RQAPGQGLEWMGQINPTTGRSQYNEKFKTRVTITADK STSTAYMELSSLRSEDTAVYYCARWGLQPFAYWGQGT LVTVSS |
| Y1258-Vk | Vk-C1 | 114 | DIVMTQSHKFMSTSVGDRVSITCKASQDVSTAVAWYQ QKPGQSPKLLIYSASYRYTGVPDRFTGSGSGTDFTFT ISSVQAEDLAVYYCQQHYSTPWTFGGGTKLEIK |
| Y1262-Vk | Vk-C2 | 115 | DIVMTQSHKFMSTSVGDRVSITCKASQDVSTAVAWYQ QKPGQSPKLLIYSASYRYTGVPDRFTGSGYGTDFTFT ISSVQAEDLAVYYCQQHYSTPWTFGGGTKLEIK |
| Y1258_IGKV1.3301-Vk | Vk-hz1 | 116 | DIQMTQSPSSLSASVGDRVTITCKASQDVSTAVAWYQ QKPGKAPKLLIYSASYRYTGVPSRFSGSGSGTDFTFT ISSLQPEDIATYYCQQHYSTPWTFGGGTKVEIK |
| Y1258_IGKV1.3902-Vk | Vk-hz2 | 10 | DIQMTQSPSFLSASVGDRVTITCKASQDVSTAVAWYQ QKPGKAPKLLIYSASYRYTGVPSRFSGSGSGTDFTLT ISSLQPEDFATYYCQQHYSTPWTFGGGTKVEIK |
| Y1258_IGKV3.1501-Vk | Vk-hz3 | 16 | EIVMTQSPATLSVSPGERATLSCKASQDVSTAVAWYQ QKPGQAPRLLIYSASYRYTGIPARFSGSGSGTEFTLT ISSLQSEDFAVYYCQQHYSTPWTFGGGTKVEIK |

Table 10 provides the heavy and variable light domain sequences used for construction of humanized antibodies, as well as chimeric antibody controls, for CD40 binding analyses using BIAcore™ surface plasmon resonance (SPR), as well as Octet BLI titer analyses (discussed below).

Vh sequences were formatted with IgG1-P238K isotype (CH1-IgG1-P238K; SEQ ID NO:25). $V_\kappa$ sequences were formatted as a full light chain with a common CL sequence (amino acids 108-214 of SEQ ID No: 11). In Table 11, "Y1258" and "Y1262" refer to chimeric molecules containing mouse variable regions and human constant regions. The various different combinations of the humanized HC constructs and LC constructs, as well as the chimeric Y1258 and Y1262 molecules were expressed as 3 milliliter (ml) supernatants for titer analysis and CD40 binding analysis. The family of molecules was collectively identified with an "Y12XX" prefix, followed by a "hz #" suffix to uniquely identify different heavy chain/light chain pairs.

Titer analysis was performed using Biolayer Interferometry (BLI) on an Octet RED instrument (Fortebio) by capturing antibodies from supernatant using protein A sensor tips and measuring capture response with respect to a standard curve obtained using a control antibody sample. SPR data were obtained by capturing antibodies on a protein A surface and testing the binding of 500 nM and 50 nM injections of human-CD40 analyte, using a BIAcore™ T200 instrument (GE Healthcare). The kinetic data for the two concentrations of hCD40-monomer were fit to a 1:1 Langmuir model, to yield estimates of the kinetic and affinity values for these interactions, and for comparison of the different molecules.

The Octet titer and BIAcore™ SPR CD40 binding data are provided in Table 11. In addition to testing supernatant ("sup") samples, purified chimeric Y1258, Y1262 and Y1268 antibodies containing human wild-type IgG1f isotype (ASTKGPSVFPLAPSSKSTSGGTAALGCLVKDYFPEPVTVSWNSGALT

SGVHTFPAVLQSSGLYSLSSVVTVPSSSLGTQTYICNVNHKPSNTKVD

KRVEPKSCDKTHTCPPCPAPELLGGPSVFLFPPKPKDTLMISRTPEVT

CVVVDVSHEDPEVKFNWYVDGVEVHNAKTKPREEQYNSTYRVVSVLTV

LHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSF

FLYSKLTVDKSRWQQGNVFSCSVMHEALHNHYTQKSLSLSPGK; SEQ

ID NO: 117)

were tested by SPR as controls; these are named "Y1258-hIgG1f", "Y1632-hIgG1f" and "Y1268-hIgG1f" in Table 11, and the Vh and Vk chains are denoted as "Chim-P."

TABLE 11

Octet titer and BIAcore™ SPR CD40 binding data

| Antibody ID | Vh | Vk | Sample | Titer (μg/ml) | ka (1/Ms) | kd (1/s) | KD (M) |
|---|---|---|---|---|---|---|---|
| Y1258-hIgG1f | Chim-P | Chim-P | purified | n/a | 5.8E+04 | 5.9E−07 | 1.0E−11 |
| Y1258 | Vh-C1 | Vk-C1 | sup | 54.2 | 5.6E+04 | 3.8E−06 | 6.7E−11 |
| Y12XX-hz1 | Vh-hz1 | Vk-hz1 | sup | 3.8 | 1.5E+04 | 1.6E−05 | 1.1E−09 |
| Y12XX-hz15 | Vh-hz1 | Vk-hz2 | sup | 34.6 | 1.6E+04 | 1.3E−04 | 8.0E−09 |
| Y12XX-hz29 | Vh-hz1 | Vk-hz3 | sup | 56.7 | 3.7E+04 | 2.6E−06 | 6.9E−11 |
| Y12XX-hz2 | Vh-hz2 | Vk-hz1 | sup | 4.5 | 1.7E+04 | 7.1E−05 | 4.1E−09 |
| Y12XX-hz16 | Vh-hz2 | Vk-hz2 | sup | 58.6 | 2.0E+05 | 6.4E−04 | 3.2E−09 |
| Y12XX-hz30 | Vh-hz2 | Vk-hz3 | sup | 82.6 | 4.1E+04 | 7.3E−07 | 1.8E−11 |
| Y12XX-hz3 | Vh-hz3 | Vk-hz1 | sup | 6.4 | 1.5E+04 | 6.7E−05 | 4.5E−09 |
| Y12XX-hz17 | Vh-hz3 | Vk-hz2 | sup | 50.7 | 3.7E+05 | 7.7E−02 | 2.1E−07 |
| Y12XX-hz31 | Vh-hz3 | Vk-hz3 | sup | 93.9 | 4.1E+04 | 2.9E−07 | 7.0E−12 |
| Y1262-hIgG1f | Chim-P | Chim-P | purified | n/a | 4.8E+05 | 5.5E−03 | 1.2E−08 |
| Y1262 | Chim | Chim | sup | 92.2 | 3.5E+05 | 2.8E−03 | 8.0E−09 |
| Y12XX-hz4 | Vh-hz4 | Vk-hz1 | sup | 4.7 | 4.6E+05 | 2.2E−03 | 4.7E−09 |
| Y12XX-hz18 | Vh-hz4 | Vk-hz2 | sup | 73.6 | 3.5E+05 | 2.4E−03 | 7.1E−09 |
| Y12XX-hz32 | Vh-hz4 | Vk-hz3 | sup | 104.3 | 2.9E+05 | 3.0E−03 | 1.0E−08 |
| Y12XX-hz5 | Vh-hz5 | Vk-hz1 | sup | 4.5 | 3.5E+05 | 2.5E−03 | 7.2E−09 |
| Y12XX-hz19 | Vh-hz5 | Vk-hz2 | sup | 56.7 | 3.8E+05 | 2.3E−03 | 6.2E−09 |
| Y12XX-hz33 | Vh-hz5 | Vk-hz3 | sup | 85.5 | 2.9E+05 | 3.3E−03 | 1.1E−08 |
| Y12XX-hz6 | Vh-hz6 | Vk-hz1 | sup | 6.7 | 3.8E+05 | 2.4E−03 | 6.4E−09 |
| Y12XX-hz20 | Vh-hz6 | Vk-hz2 | sup | 50.3 | 3.1E+05 | 2.5E−03 | 8.2E−09 |
| Y12XX-hz34 | Vh-hz6 | Vk-hz3 | sup | 93.7 | 3.7E+05 | 2.8E−03 | 7.6E−09 |
| Y12XX-hz8 | Vh-hz8 | Vk-hz1 | sup | 11.2 | 7.2E+05 | 1.5E−01 | 2.1E−07 |
| Y12XX-hz22 | Vh-hz8 | Vk-hz2 | sup | 49.1 | 3.7E+05 | 7.9E−02 | 2.1E−07 |
| Y12XX-hz36 | Vh-hz8 | Vk-hz3 | sup | 136.7 | 3.9E+05 | 1.0E−01 | 2.5E−07 |
| Y1268-hIgG1f | Chim-P | Chim-P | purified | n/a | 4.0E+05 | 1.3E−03 | 3.2E−09 |
| Y12XX-hz9 | Vh-hz9 | Vk-hz1 | sup | 5.1 | 2.0E+05 | 8.9E−04 | 4.6E−09 |
| Y12XX-hz23 | Vh-hz9 | Vk-hz2 | sup | 59.4 | 2.0E+05 | 6.4E−04 | 3.2E−09 |
| Y12XX-hz37 | Vh-hz9 | Vk-hz3 | sup | 138.4 | 2.6E+05 | 8.4E−04 | 3.3E−09 |
| Y12XX-hz10 | Vh-hz10 | Vk-hz1 | sup | 8.6 | 2.0E+05 | 7.3E−04 | 3.6E−09 |
| Y12XX-hz24 | Vh-hz10 | Vk-hz2 | sup | 48.1 | 1.9E+05 | 8.2E−04 | 4.4E−09 |
| Y12XX-hz38 | Vh-hz10 | Vk-hz3 | sup | 185.5 | 2.5E+05 | 8.8E−04 | 3.6E−09 |
| Y12XX-hz11 | Vh-hz11 | Vk-hz1 | sup | 7.5 | 1.8E+05 | 8.8E−04 | 5.0E−09 |
| Y12XX-hz25 | Vh-hz11 | Vk-hz2 | sup | 55.4 | 1.9E+05 | 6.4E−04 | 3.4E−09 |
| Y12XX-hz39 | Vh-hz11 | Vk-hz3 | sup | 134.2 | 2.4E+05 | 8.4E−04 | 3.5E−09 |
| Y12XX-hz12 | Vh-hz12 | Vk-hz1 | sup | 2.7 | 1.7E+05 | 1.4E−03 | 8.3E−09 |
| Y12XX-hz26 | Vh-hz12 | Vk-hz2 | sup | 36.8 | 1.6E+05 | 1.2E−03 | 7.5E−09 |
| Y12XX-hz40 | Vh-hz12 | Vk-hz3 | sup | 99.8 | 2.4E+05 | 1.1E−03 | 4.7E−09 |
| Y12XX-hz13 | Vh-hz13 | Vk-hz1 | sup | 3.0 | 2.1E+05 | 8.3E−04 | 3.9E−09 |
| Y12XX-hz27 | Vh-hz13 | Vk-hz2 | sup | 49.5 | 1.9E+05 | 8.8E−04 | 4.7E−09 |
| Y12XX-hz41 | Vh-hz13 | Vk-hz3 | sup | 52.7 | 2.5E+05 | 9.4E−04 | 3.8E−09 |
| Y12XX-hz14 | Vh-hz14 | Vk-hz1 | sup | 5.0 | 1.7E+05 | 8.3E−04 | 5.0E−09 |
| Y12XX-hz28 | Vh-hz14 | Vk-hz2 | sup | 70.1 | 1.8E+05 | 6.2E−04 | 3.5E−09 |
| Y12XX-hz42 | Vh-hz14 | Vk-hz3 | sup | 100.0 | 2.4E+05 | 8.3E−04 | 3.5E−09 |

For a given heavy chain construct, the titer is generally highest when paired with light chains containing Vk-hz3 (SEQ ID NO:18), lower for heavy chains paired with Vk-hz2 (SEQ ID NO:10), and the lowest for heavy chains paired with Vk-hz1 (SEQ ID NO:116) containing light chains.

The SPR analysis data show that the antibodies bound with variable affinity to CD40, with KD values ranging from greater than 1 E-07 to less than 1 E-09. For some antibodies, the affinity was too strong to accurately determine with confidence in this assay, because the dissociation rate was too slow to measure. These values, which are italicized in the table, are beyond the limit of accurate quantitation in this assay.

Based on the sequences, titer, and SPR binding data, antibodies were selected for larger scale expression, purification, and further characterization. SPR analysis using purified antibodies was performed by capturing antibodies on a protein A surface, with binding of a 500-3.9 nM (2:1) dilution series of human-CD40 monomer, at either 25° C. or 37° C. in PBS-T pH 7.1 buffer; the titration data was fit to a 1:1 Langmuir model. The data is provided in Table 12.

TABLE 12

SPR kinetic/affinity data

| | | 25° C. | | | 37° C. | | |
|---|---|---|---|---|---|---|---|
| Ligand | Sample | ka (1/Ms) | kd (1/s) | KD (nM) | ka (1/Ms) | kd (1/s) | KD (nM) |
| Y12XX-hz28 | hCD40 | 2.2E+05 | 6.9E−04 | 3.1 | 4.4E+05 | 3.7E−03 | 8.5 |
| Y12XX-hz40 | hCD40 | 2.9E+05 | 1.3E−03 | 4.4 | 5.2E+05 | 5.7E−03 | 10.9 |
| Y12XX-hz42 | hCD40 | 3.1E+05 | 7.3E−04 | 2.3 | 6.3E+05 | 3.4E−03 | 5.5 |
| Antibody B | | 6.1E+04 | 2.3E−03 | 37 | | | |

These data show that the selected Y12XX antibodies bind with high affinity and KD values in the range of KD=1 E-9 M at 25° C. The binding is compared to that of another anti-CD40 antibody, antibody BI-mAb-B (U.S. Pat. No. 9,090,696, heavy chain sequence SEQ ID NO: 32 and light chain sequence SEQ ID NO: 31; referred to herein as "Antibody B" and "BI-LALA"). As shown by the data in Table 12, Antibody B binds to CD40 with much lower affinity than the humanized Y12XX molecules.

All three humanized versions of the Y12XX antibody were potent antagonists of B cell proliferation stimulated with CD40L-IZ trimeric agonist. See Table 13.

TABLE 13

Inhibition of B cell proliferation induced by soluble CD40L trimer

|  | Average (IC50 ng/ml) | Standard Deviation (STDEV) | n donors |
|---|---|---|---|
| Antibody B | 9.4 | 3.9 | 6 |
| Y12XX-hz28-P238K | 6.7 | 3.6 | 8 |
| Y12XX-hz40-P238K | 6.0 | 4.7 | 2 |
| Y12XX-hz42-P238K | 12.1 | 2.3 | 2 |

Y12XX-hz28-P238K was also a potent antagonist of B cell proliferation stimulated with cellular CD40L from CD40L-expressing CHO cells. See Table 14.

TABLE 14

Potency for inhibition of CD40L expressing CHO cells stimulation of B cell proliferation

|  | Potency (IC50 ng/ml of % inhibition) | Standard deviation | n donors |
|---|---|---|---|
| Antibody B | 62% * | 25% | 6 |
| Y12XX-hz28-P238K | 38.1 | 9.8 | 8 |

* % inhibition at highest dose tested (1-3 µg/ml)

The data for the humanized Y12XX antibodies is compared to that of Antibody B, which showed potent inhibition of B cell proliferation driven by soluble CD40L signals, but was much less effective at inhibition of B cell proliferation driven by cellular CD40L (CHO cells overexpressing CD40L). In contrast, humanized Y12XX antibodies exhibited only a <10 fold shift in the potency for inhibition of cell surface CD40L stimulation, providing more robust blockade of B cell responses to CD40L.

Humanized Y12XX antibodies were formatted with IgG1-P238K isotype (CH1-IgG1-P238K; SEQ ID NO: 25) to reduce the binding affinity for FcγRs and reduce FcγR-mediated signaling. FcγR binding for a representative humanized Y12XX antibody with this IgG1-P238K isotype (Y12XX-hz28-IgG1-P238K) was compared to the binding of a control antibody formatted with a wild type IgG1 isotype (control-IgG1) as well as Antibody B which has an IgG1 isotype containing the mutations L234A-L235A. These L234A-L235A mutations are also introduced to reduce FcγR binding.

FcγR binding SPR studies were performed by capturing antibodies on a protein A sensor chip surface and binding purified His-tagged human FcγRs as analyte. hCD64 binding consisted of a titration of 10 µM-1.5 nM hCD64 (2:1 dilution series), while data for the low affinity FcγRs hCD32a-H131, hCD32a-R131, hCD32b, hCD16a-V158, and hCD16a-F158 consisted of a titration of 10 uM-13.7 nM FcγR protein.

Figure 1B:
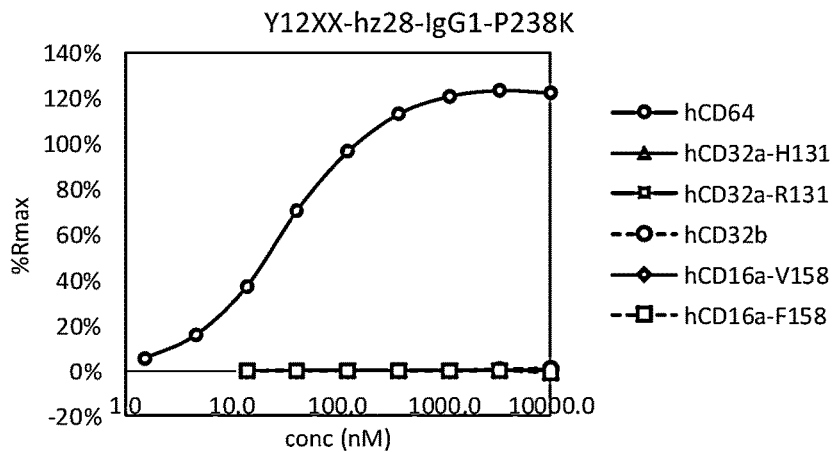
Figure 1C:
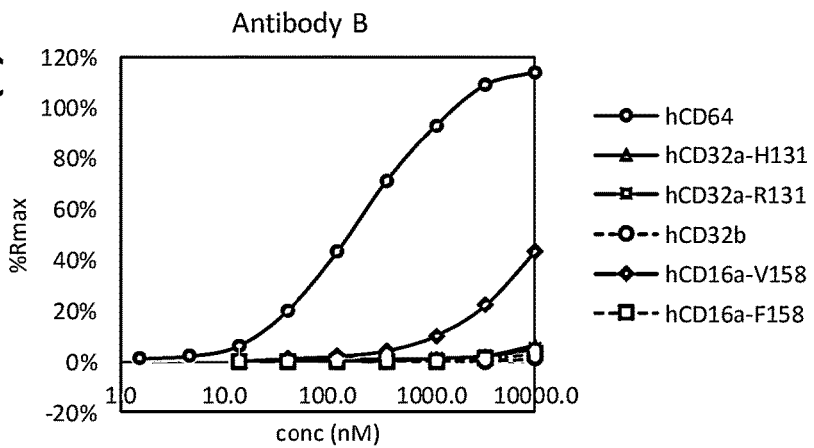

The control-IgG1 antibody demonstrated binding to all of the FcγRs tested. See FIG. 1A. Compared to wild type, the Y12XX-hz28-IgG1-P238K antibody demonstrated 125-fold weaker binding to hCD64, and demonstrated no detectable binding to any of the low affinity FcγRs hCD32a-H131, hCD32a-R131, hCD32b, hCD16a-V158 and hCD16a-F158 tested. See FIG. 1B. Antibody B also demonstrated weaker hCD64 binding than wild type IgG1, but also demonstrated appreciable binding to hCD16a-V158 (KD=7 µM) and some weak binding to hCD32a-H131 and hCD32a-R131. See FIG. 1C. The KD values are provided in FIG. 1D.

Humanized versions of the antibody Y12XX with P238K mutation in the Fc region were further tested for any agonist activity. Monocyte derived immature dendritic cells (iDC) are very sensitive to CD40 activation, increasing cytokine production (IL-6) and upregulating surface markers of activation (CD86 and CD54) upon CD40 stimulation. Therefore, the most promising humanized Y12XX antibodies were tested to assess their ability to stimulate iDC. The ability of CD40 antibodies to agonize CD40 can be enhanced by clustering or cross-linking binding of the Fc portions of the molecule to cell surface FcγR. Addition of CHO cells highly over-expressing CD32a, the low affinity FcγR, were used to evaluate the potential for FcγR mediated clustering/cross-link. The ratio of CHO cells to iDCs was 1:6 in these experiments, representing a potentially exaggerated level of clustering/cross-linking. BMS-986090 and 2141 were used as positive controls. BMS-986090 is an anti-CD40 antagonist domain antibody fused to IgG4 Fc (see SEQ ID NO: 1287 in WO 2012/145673). 2141 (mAb 134-2141) is a partial CD40 agonist (see Robert Vonderheide et al., 2007, *J. Clin. Oncol.* 25(7): 876-883). L6-IgG4 is a fusion protein with no CD40 binding capability, and served as a negative control.

Figure 2A:
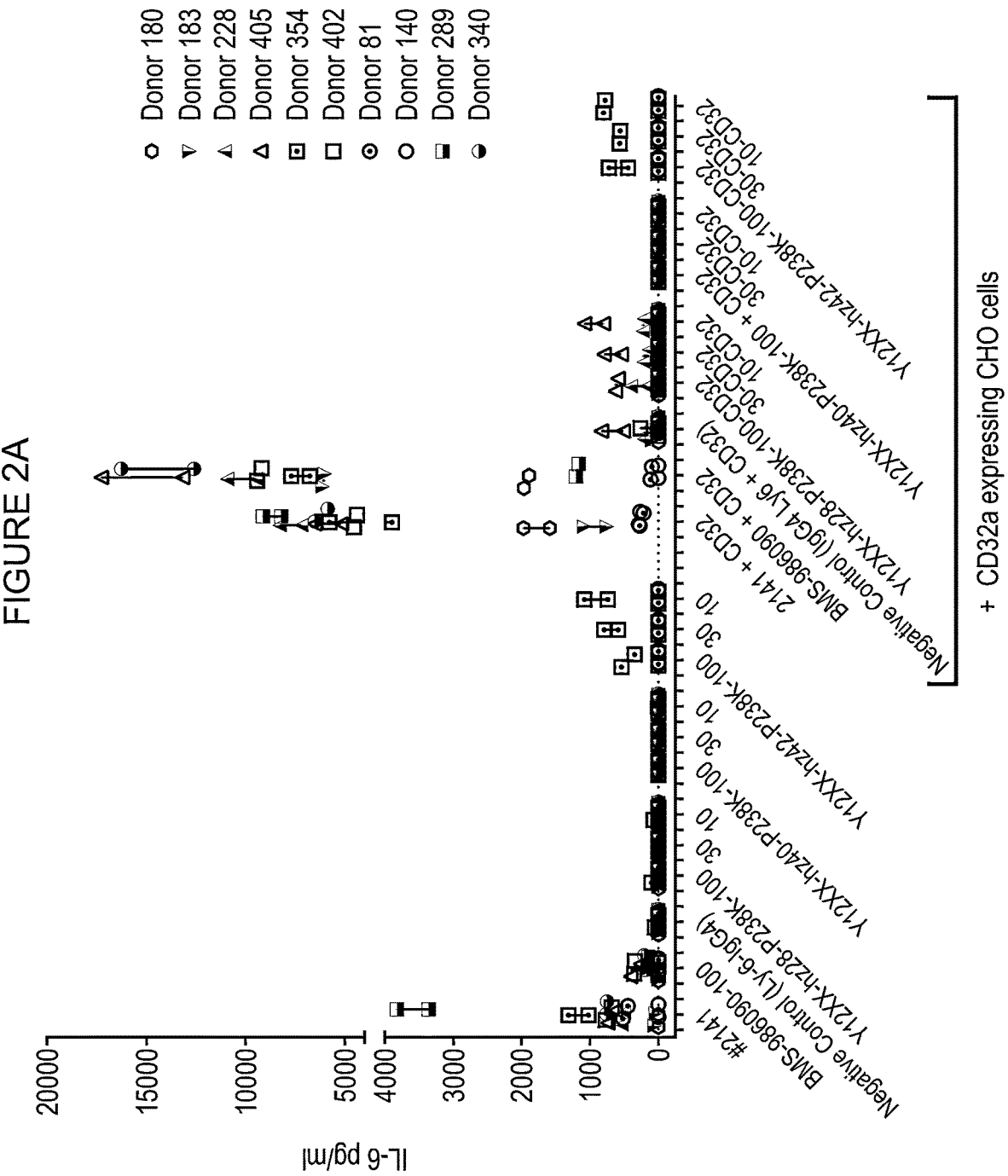

As illustrated by the data in FIGS. 2A-2C, the addition of either the partial agonist 2141 or BMS-986090 led to only weak activation of iDC in a subset of donors. However, addition of CD32a- expressing CHO cells to either 2141 or BMS-986090 led to robust increases in IL-6 production (FIG. 2B) and CD86 and CD54 upregulation (FIG. 2B and FIG. 2C, respectively) in nearly every donor tested, consistent with FcγR mediated clustering of these molecules through their Fc portions leading to CD40 activation. In contrast, Y12XX-hz28-P238K and Y12XX-hz40-P238K either alone or with CD32 dependent clustering did not show any signs of iDC activation above that observed with the negative control using iDC cells from 6-10 donors. Y12XX-hz42-P238K was tested in cells from 4 donors and exhibited signs of weak activation including IL-6 production and CD86 and CD54 upregulation in only one of the four donors, which, unlike the activity seen with 2141 or BMS-986090, was not dependent on the addition of CD32a-expressing CHO cells.

Materials and Methods For Examples 1 and 2

FcγR binding SPR: FcγR binding can be measured in vitro using purified FcγRs using methods, such as BIAcore™ surface plasmon resonance (SPR). One method tests the binding of purified His-tagged FcγR proteins (FcγR-his) to antibodies that are captured on a sensor surface containing protein A which has been immobilized using standard ethyl (dimethylaminopropyl) carbodiimide (EDC)/N-hydroxysuccinimide (NHS) chemistry with ethanolamine blocking. These experiments are performed on a BIAcore™ T200 instrument (GE Healthcare, Marlborough, MA) at 25° C. For example, samples of purified antibody at 3 µg/ml concentration are first captured on the immobilized protein A surface using a 15 second (s) contact time at 10 µl/min flow rate. This is followed by the binding of purified FcγR-His proteins at various concentrations, such as 10 µM-1.5 nM (2:1 dilution series) or 10 µM-13.7 nM (2:1 dilution series), using 120 s association and dissociation times at a flow rate of 30 µ/min. All steps are performed in a running buffer consisting of 10 mM NaPO$_4$, 130 mM NaCl, 0.05% p20 (PBS-T) pH 7.1. FcγR proteins tested in these studies include the "high affinity" FcγR CD64 (hFcγRI), as well as the "low affinity" FcγRs CD32a-H131 (FcγRIIa-H131), CD32a-R131 (FcγRIIa-R131), CD32b (FcγRIIb), CD16a-V158 (FcγRIIIa-V158), and CD16a-F158 (FcγRIIIa-F158), which were expressed and purified in house. SPR data are fit to either a 1:1 Langmuir model, or a 1:1 steady state model using BIAcore™ T200 evaluation software to obtain values for the association rate constant (ka), dissociation rate constant (kd) and dissociation constant ($K_D$).

To compare binding responses for different FcγRs, SPR data can be analyzed by calculating the maximum binding response as a percentage of the theoretical maximum binding response (% Rmax), using the equation:

$$\% \text{ Rmax} = (\text{Binding Response Analyte})/[((\text{Mw Analyte})/(\text{Mw Ligand})) \times (\text{Response Ligand}) \times (\text{analyte:ligand stoichiometry})] \quad \text{EQUATION 1}$$

where "Analyte" is the FcγR and "Ligand" is the captured antibody. This analysis does not take into account the mass of glycosylation of antibody or FcγR, and assumes 100% fractional activity for the captured ligand. Since the FcγRs are glycosylated, the % Rmax values are typically great than 100% under saturating conditions.

CD40 binding kinetics and affinity: The monovalent CD40 binding affinity of the antibody molecules is measured by surface plasmon resonance (SPR) on a BIAcore™ T200 instrument (GE Healthcare Life Sciences) at 25° C. or 37° C. by capturing antibody on an immobilized protein A sensor chip surface, and then binding human-CD40-monomer protein (generated in house) using, for example, an association time of 180 seconds, and dissociation time of 180 seconds or 360 seconds at 30 µl/min in PBS-T, pH 7.1. SPR data are fit to a 1:1 Langmuir model using BIAcore™ T200 evaluation software to obtain values for the association rate constant (ka), dissociation rate constant (kd) and dissociation constant (KD).

Titer analysis: Titer analysis was performed using Bio-layer Interferometry (BLI) on an Octet® RED instrument (ForteBio, Freemont, CA) at 25° C. Antibodies are captured from supernatant using protein A sensor tips using association time of 120 seconds and the binding response is measured and compared to a standard curve obtained using a control antibody sample to determine the concentration of antibody in the supernatant.

Primary Cell Isolation and Culture: Peripheral blood mononuclear cells (PBMC) were isolated from heparinized human blood by Ficoll density gradient separation. Monocytes were isolated from PBMC following the Manual EasySep™ protocol (STEMCELL, Vancouver, Canada). One million of isolated monocytes were plated in in each well of a 6-well plate in 6 mLs of complete media (RPMI-1640, 10% heat-inactivated fetal bovine serum, 100 units/ml penicillin-streptomycin), containing IL-4 (100 ng/ml) and GM-CSF (100 ng/ml) and incubated for 6 days at 37° C./5% $CO_2$, changing media every other day and replacing it with fresh media containing the same concentration of cytokines. iDCs (immature dendritic cells) were harvested on day 6, washed thoroughly, and re-suspended in complete media.

Treatment of iDCs with anti-CD40 Antibodies in the Presence or Absence of FcγR Clustering/Crosslinking: Titrations of the various biological agents were made in complete media, and added to duplicate 96-well plates. In the case of cross-linking, antibodies were added to the cells for 30 min prior to the addition of CD32a-expressing CHO cells at a ratio of 1:6. Cells were incubated at 37° C./5% $CO_2$ for approximately 18-20 hours, 150 µL of supernatant was removed from each well, diluted 1:5 and evaluated for protein concentrations of IL-6, TNFα and IL-12 using a commercially available ELISA kits (R&D Systems, Minneapolis, MN), according to manufacturer's instructions. The cells remaining in the plates from the harvested supernatants were combined into 1 sample per duplicate treatment, and transferred to new 96-well round bottom (RB) plate, and placed at 4° C. Cells were washed with D-PBS, Ca++ and Mg++ free, and stained for 30 min on ice for cell viability using the LIVE/DEAD® Fixable Near-IR Dead Cell Stain Kit (Invitrogen, Carlsbad, CA). Cells were washed and re-suspended in D-PBS, Ca++ and Mg++ free, 2% FBS, 0.1% $NaN_3$ (staining buffer) and blocked with 5 µl/well of Human TruStain FcX™ (Fc Receptor Blocking Solution, Biolegend, San Diego, CA) in staining buffer.

DCs were immuno-stained with: PerCpCy5.5-conjugated αCD3, αCD19, αCD14 (Lin⁻), BUV395-conjugated αCD11c (BD Biosciences, San Diego, CA), APC-conjugated αCD86 (Biolegend, San Diego, CA), PE-conjugated αCD83 (eBioscience, San Diego, CA), FITC-conjugated αCD54 (Biolegend, San Diego, CA), and incubated at 4° C. for 45 minutes. Cells were washed twice in staining buffer and fixed (15 at RT, protected from light), by adding 100 µl of BD Cytofix Fixation Buffer (BD Bioscience, San Diego, CA). DCs were evaluated for CD86, ICAM-1 and CD83 expression using a LSRII-Fortessa Flow Cytometer (BD Biosciences, San Diego, CA), and FlowJo analysis software (Treestar, Ashland, OR).

Inhibition of CD40L induced human B cell proliferation: Human tonsillar B cells were obtained from pediatric patients during routine tonsillectomy and isolated by mincing and gently mashing the tissue, passing the cells through a screen and isolating mononuclear cells with density gradient separation using human Lympholyte®-H separation media (Cedarlane Labs, Burlington, ON). Mononuclear cells were collected from the interface, washed, and rosetted with sheep red blood cells (SRBC, Colorado Serum Company; Denver, CO) for one hour at 4° C., followed by density gradient separation to remove T cells. Cells were again washed and re-suspended in RPMI containing 10% FBS (complete media). Titrations of antibodies were made in complete media, and added in triplicate to 96-well round bottom (RB) plates. $1 \times 10^5$ tonsillar human B cells were added and stimulated with either soluble IZ-hCD40L (2 µg/mL), or with Chinese hamster ovary cells stably transfected with human CD40L (CHO-hCD40L) irradiated with 10,000 rads, and plated at $2 \times 10^3$ cells/well, in a final volume of 200 µL in each well. Plates were incubated at 37° C./5% $CO_2$ for 72 hours, labeled for the last 6 hours with 0.5 µCi of ³[H]-thymidine per well, harvested, and counted by liquid scintillation. B cell proliferation was quantitated based on thymidine incorporation.

Example 3: In Vitro Fc Receptor Assays

Antibodies can exert effector functions, such as complement dependent cytotoxicity (CDC), and antibody dependent cellular cytotoxicity (ADCC), by binding of the Fc region to Fc gamma receptors (FcγRs) on the surface of immune cells or complement factors. Antibody dependent cellular phagocytosis is another potential Fc effector function. To further characterize the properties of the humanized Y12XX antibodies, the antibodies were assayed for complement dependent cytotoxicity (CDC), antibody dependent cellular phagocytosis (ADCP), and antibody dependent cellular cytotoxicity (ADCC). Table 15 lists the antibodies assayed in this example.

TABLE 15

| | Name | Reference |
|---|---|---|
| 1 | BMS-986291 (Y1238-hz1-P238K) | See WO 2018/217976 |
| 2 | 15B5-hz61-P238K | anti-CD40 antibody (produced in house) |
| 3 | 5F11-45-P238K | See WO 2018/217976 |
| 4 | Y12XX-hz28-P238K | |
| 5 | Y12XX-hz40-P238K | |
| 6 | Y12XX-hz42-P238K | |
| 7 | Antibody C | anti-CD40 antibody (See Ristov et al. (2018) Am J Transplant. 18(12): 2895-2904. Epub 2018 May 24.) |
| 8 | BI-LALA | See U.S. Pat. No. 9,090,696, heavy chain sequence SEQ ID NO: 32 and light chain sequence SEQ ID NO: 31; IgG1 isotype containing the mutations L234A-L235A |
| 9 | BMS-986090 | CD40 domain antibody (BMS3h-56-269-IgG$_4$ Fc fusion polypeptide); see, e.g., WO 2012/145673) |
| 10 | TT hIgG1 | Human anti-tetanus toxin antibody, IgG1 isotype (produced in house) (isotype control) |
| 11 | CD20 hIgG1 | Human anti-CD20, IgG2 isotype (produced in house) (positive control) |

The CDC assay was performed as follows. "CDC Assay Medium" refers to Roswell Park Memorial Institute medium (RPMI)-1640 (HyClone) with L-glutamine, phenol red-free (HyClone) supplemented with 0.1% BSA (Sigma), and 1% Penicillin-Streptomycin (Life Technologies). Fifty (50) microliters of target cells ($5 \times 10^5$ cells/mL in CDC assay medium) were added to wells of a 96-well assay plate. The target cells were Raji cells which endogenously express CD40 (obtained from ATCC). Serial dilutions (from 133 to 0.002 nM) were prepared for each antibody tested, and 25 microliters of each antibody concentration were added to each well. Twenty-five microliters of human complement (obtained from Quidel; diluted 1:3 with CDC assay medium) was added to each well. The assay plates were incubated at 37° C. for 4 hours in a humidified incubator. After the incubation, 100 microliters of CellTiter-Glo® (Promega, Madison, WI) was added to each well. Luminescence data was then acquired with a PerkinElmer EnVision® Plate Reader (PerkinElmer, Waltham, MA). Percent viability was calculated relative to isotype control (100% viable). The resulting values are plotted against antibody concentration. Percentage of cell viability is plotted for each antibody using Prism v5.01 software from GraphPad Inc.

Figure 3A:
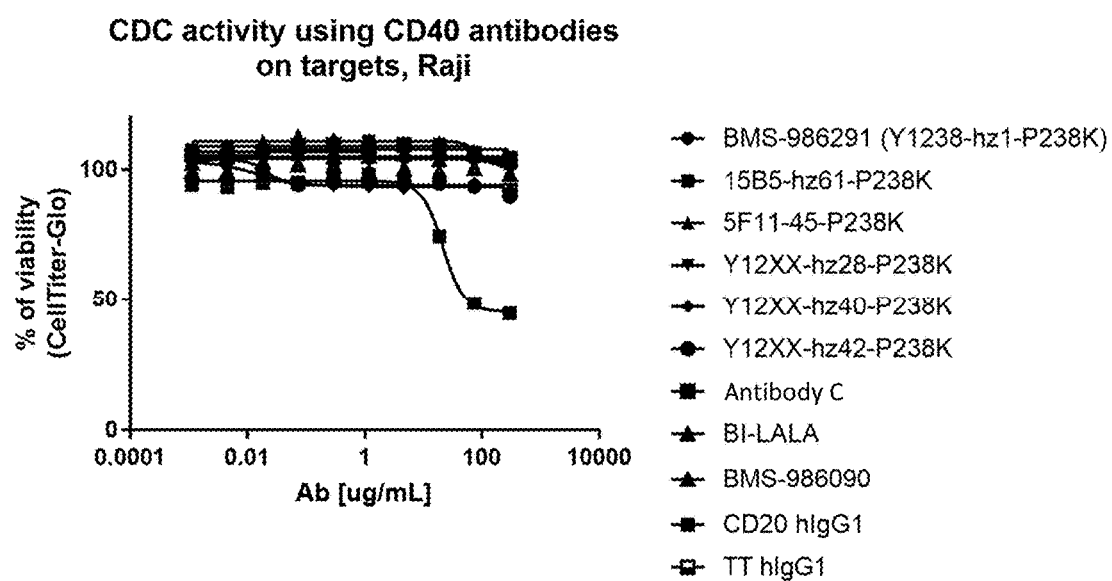
FIGS. 3A and 3B depict exemplary data from complement dependent cytotoxicity (CDC) analysis of humanized Y12XX antibodies, CD40 antibodies, and control antibodies. The CDC assay was performed twice. In the second assay, freshly thawed human complement serum was used.
Figure 3B:
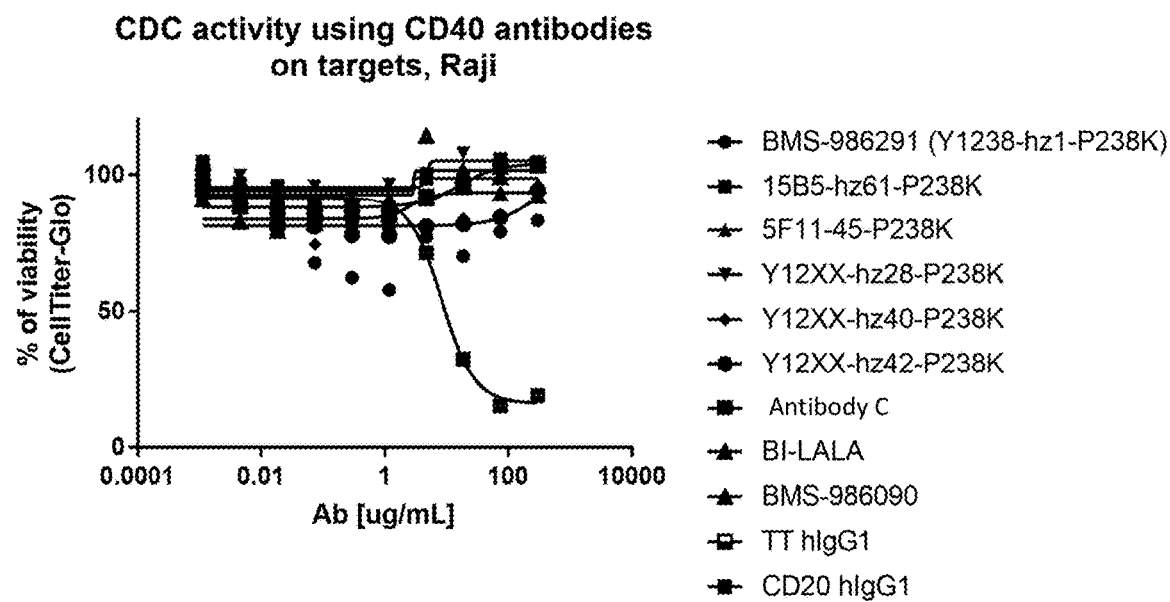

The CDC assay was performed twice. In the second assay, freshly thawed human complement serum was used. The results are depicted in FIGS. 3A and 3B. FIG. 3A depicts the first iteration of the assay, and FIG. 3B depicts the second iteration of the assay. CD20 hIgG1 is a positive control and showed cytotoxicity. No detectable CDC activity was present for the anti-CD40 antibodies assayed, and specifically, none of the humanized Y12XX antibodies assayed induced complement-dependent cytotoxicity.

The ADCP assay was performed as follows. "ADCP assay media" refers to RPMI-1640 media with L-glutamine, phenol red-free (HyClone) supplemented with 10% ultra-low IgG FBS (Gibco). The effector cells were primary human CD14+ monocytes purified from fresh PBMCs from 2 different healthy human donors. The target cells were again Raji cells. The Raji cells were labeled with 2.0 μM PKH26 (red fluorescent dye; Sigma), and the concentration was adjusted to $4 \times 10^6$ cells/mL in ADCP assay media. The labeled target cells were pre-coated with antibodies by adding labeled target cells (50 μL/well) to a V-bottom 96-well plate containing 50 μL/well of test or control antibody, and incubating for 30 minutes over ice. The cells were washed, then effector cells (CD14+ monocytes) were added (100 μL/well) to result in a final effector cell-to-target cell ratio (E:T) of 1:4 and a final antibody concentration ranging from 30 nM to 0.1 nM. The plate was then placed in a humidified 37° C. incubator for 1 hour. Cells were stained with APC-anti-CD89 (BioLegend) for 30 min on ice and analyzed by flow cytometer (BD Canto™, BD Biosciences, San Jose, CA). Cells were gated for CD89+ cells and subsequently for stained phagocytosed effectors (CD89+, PKH26+). The percentage of phagocytosis was calculated as the population of CD89+, PKH26+ cells among the total CD89+ cells. Background value from the isotype control was subtracted to achieve the final percentage of phagocytosis. Data was analyzed using FlowJo software and Prism v5.01 software from GraphPad Inc.

Figure 4A:
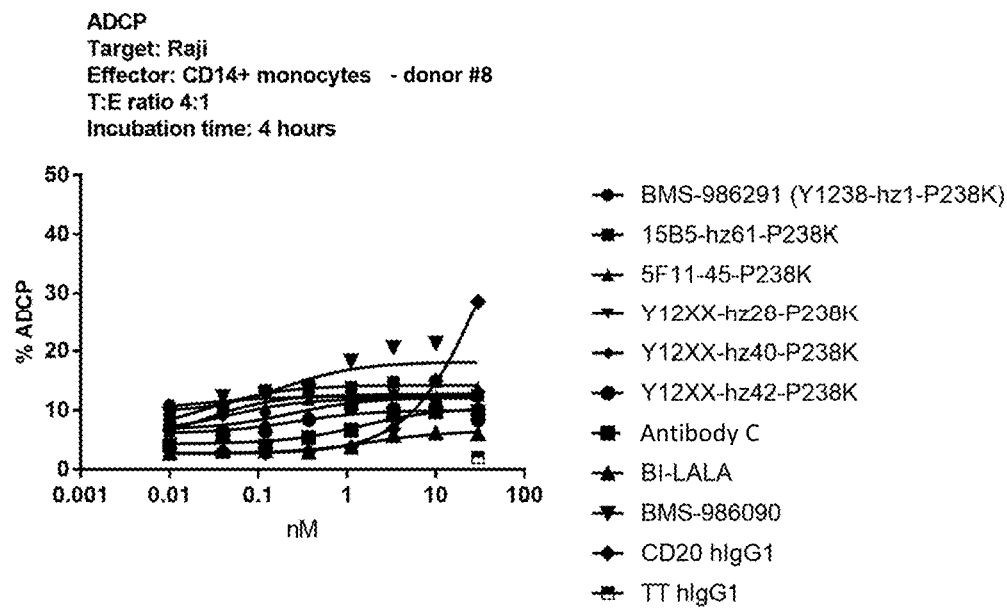
FIGS. 4A and 4B depict exemplary data from antibody dependent cellular phagocytosis (ADCP) analysis of humanized Y12XX antibodies or control antibodies, using CD14+ monocytes from two different donors as effector cells.
Figure 4B:
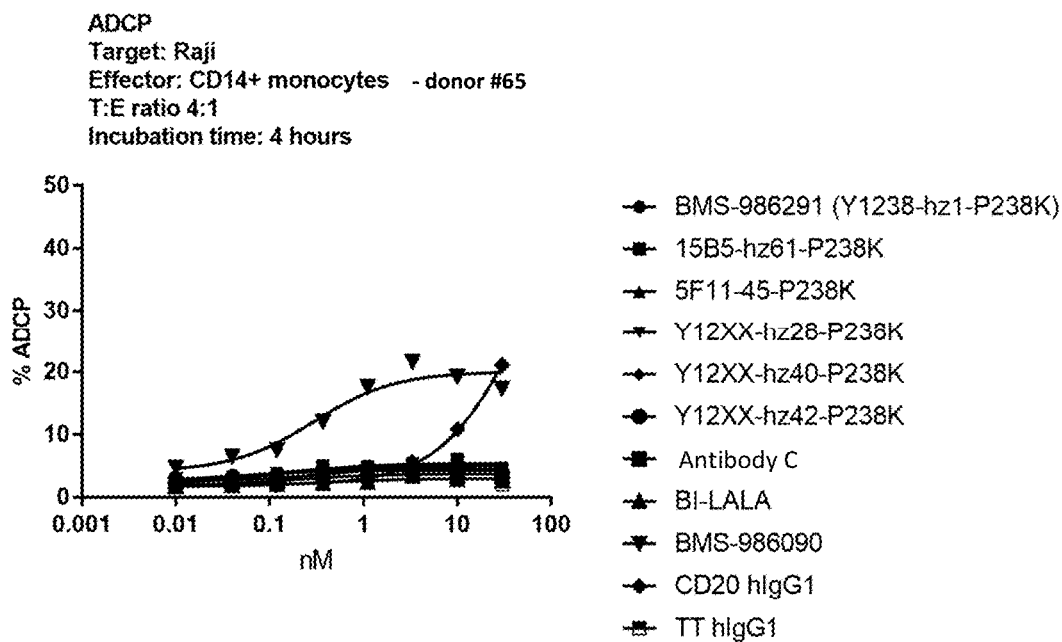

Exemplary data using CD14+ monocytes from two different donors are depicted in FIGS. 4A and 4B. CD20 hIgG1 is a positive control and induced phagocytosis of Raji cells, as expected. BMS-986090 also induced phagocytosis. In contrast, none of the other antibodies tested, including the humanized Y12XX anti-CD40 antibodies of this disclosure, induced detectable phagocytosis in this assay.

The ADCC assay was performed as follows. "ADCC assay media" refers to RPMI-1640 with L-glutamine, phenol red-free (HyClone) supplemented with 10% ultra-low IgG FBS (Gibco), and 1 mM sodium pyruvate (Life Technologies). Primary human NK (natural kill) cells were purified from fresh PBMCs from 2 different in-house donors, and used as effector cells. PBMC were purified from heparinized whole blood samples by density gradient centrifugation and washed with PBS supplemented with 2% FBS (HyClone). NK cells were isolated from PBMC by negative selection using a magnetic bead-based separation kit (Miltenyi Biotec). To activate the NK cells, purified NK cells were resuspended at $1 \times 10^6$ cells/mL in MyeloCult H5100 media (StemCell Technologies) supplemented with 1 μM hydrocortisone (StemCell Technologies) and 500 IU/mL recombinant human IL-2 (Peprotech) and incubated overnight at 37° C. The following day, activated NK effector cells were washed twice in ADCC assay media and the concentration was adjusted to $5 \times 10^5$ cells/mL in ADCC assay media. Raji cells (the target cells) were labeled with calcein, as follows. Calcein AM (Life Technologies) reagent was prepared by adding 20 μL of ultrapure DMSO to the reagent tube containing 50 μg of lyophilized reagent. A volume of 2 μL of reconstituted Calcein AM was added to the suspended Raji cells for every 1 mL of volume; the cells were vortexed and placed in a humidified 37° C. incubator for 30 minutes. After the incubation period, the labeled target cells were washed 3 times with ADCC assay media, and the concentration was adjusted to $10^5$ cells/mL in ADCC assay media. Labeled target cells (50 μL/well) were added to a V-bottom 96-well plate containing 50 μL/well of test or control antibody. Activated NK effector cells were then added (100 μL/well) to result in a final effector cell-to-target cell ratio (E:T) of 10:1, and a final antibody concentration ranging from 0.0002 to 1 μg/mL. The plate was then placed in a humidified 37° C. incubator for 2 hours. Supernatant (50 μL/well) was transferred into an optical 96-well black plate, and calcein release was measured by reading fluorescence intensity using an EnVision® Plate Reader (PerkinElmer, Waltham, MA) set to 485 excitation and 535 nm emission filters.

Target cells incubated with effector cells in the absence of antibody provided the control for background of antibody-independent lysis (spontaneous lysis), while target cells lysed with 20 μL/well 10% Tween-20 lysis buffer represented maximal release in the assay.

The percentage of antibody-dependent cell lysis was calculated based on mean fluorescence intensity (MFI) with the following formula:

$$\left(\frac{test\ MFI - mean\ background}{mean\ maximum - mean\ background}\right) \times 100 \quad \text{Equation 2}$$

Percentage of target cell lysis was plotted for each antibody using Prism v5.01 software from GraphPad Inc.

Figure 5A:
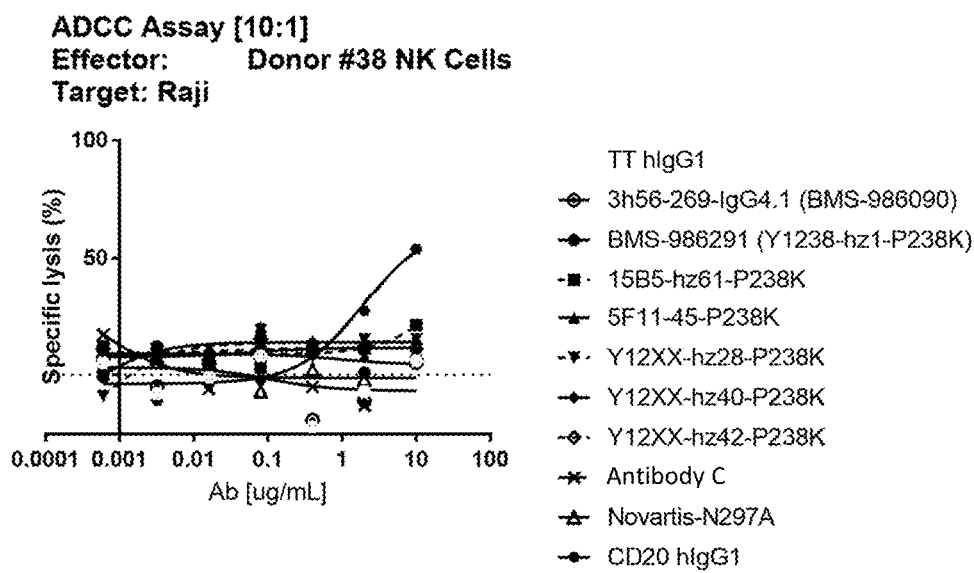
FIGS. 5A and 5B depict exemplary data from antibody dependent cellular cytotoxicity (ADCC) analysis of humanized Y12XX antibodies or control antibodies, using NK cells from two different donors as effector cells.
Figure 5B:
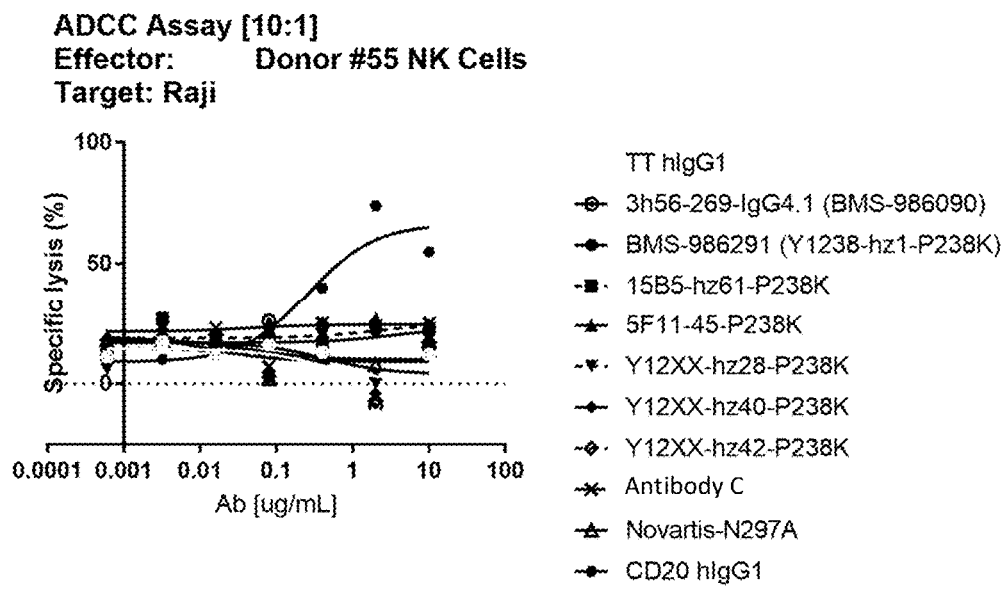

Exemplary data using NK cells from two different donors are depicted in FIGS. 5A and 5B. Target cells were killed by positive control anti-CD20 antibody. In contrast, ADCC is low-to-negative for all of the anti-CD40 antibodies, indicating that these antibodies do not induce antibody-dependent cytotoxicity of Raji cells and evidencing the CD40 antagonism of these antibodies.

In summary, in this example, the potential of the humanized Y12XX anti-CD40 antibodies of this disclosure, and specifically, Y12XX-hz28-P238K, Y12XX-hz40-P238K, and Y12XX-hz42-P238K, to mediate ADCC (antibody-dependent cellular cytotoxicity), ADCP (antibody-dependent cellular phagocytosis), or CDC (complement-dependent cytotoxicity) was tested using endogenous-CD40-expressing Raji cells as targets. Anti-CD20 antibody was used as a positive control. For ADCC, NK cells were used as effector cells, and two experiments were run with effector cells from different donors. In each case, none of Y12XX-hz28-P238K, Y12XX-hz40-P238K, and Y12XX-hz42-P238K induced lysis of Raji cells. None of Y12XX-hz28-P238K, Y12XX-hz40-P238K, and Y12XX-hz42-P238K induced CDC of Raji cells beyond the effect of human IgG1 isotype control. For ADCP, CD14+ monocytes were utilized as effector cells, and in this system none of Y12XX-hz28-P238K, Y12XX-hz40-P238K, and Y12XX-hz42-P238K promoted cellular phagocytosis. In contrast, BMS-986090 exhibited cellular phagocytosis.

Example 4: Assay of NF-kB/AP-1 Signaling

The objective of this example was to assess the NF-κB/AP-1 inducible SEAP (secreted embryonic alkaline phosphate) activity on Ramos-Blue™ Cells (InvivoGen) resulting from stimulation with anti-CD40 antibodies.

Ramos-Blue™ Cells are a human B lymphocyte reporter cell line that express an NF-κB/AP-1 inducible secreted embryonic alkaline phosphate (SEAP) reporter gene. The Ramos-Blue™ cell line has been used for NF-κB/AP1 signaling as well as in Toll-like Receptors' (TLR's) signaling pathways, Ramos-Blue™ Cells endogenously express CD40 and are responsive to CD40 and TLR. When Ramos-Blue™ Cells lines are stimulated, they produce SEAP in the cell culture supernatant. SEAP can be detected by using the QUANTI-Blue™ detection medium (InvivoGen, San Diego, CA). Levels of SEAP can be observed visually or by using a spectrophotometer at 620 nm. Ramos-Blue™ Cells do not express CD32 (FcγRII).

Table 6 lists the test materials (antibodies and other polypeptide) assayed in this example. All of the test materials were prepared in house by BMS.

TABLE 16

| Test Materials | Description |
| --- | --- |
| BMS-986325 | Y12XX-hz28-P238K (fully human anti-CD40 isotype hIgG (P238K) mAb |
| BMS-986090 | fully human anti-CD40 domain antibody IgG4 Fc fusion protein |
| mAb 134-2142 (CD40-2142 (hIgG2-Fc)) | fully human anti-CD40 monoclonal antibody (agonist) |
| Anti-DT1D12-B16F7-hIgG1.3f mAb | Negative Control |
| CD40L-IZ | a human CD40L-Trimer (h-IZ-hCD40L-Trimer) |

Ramos-Blue™ Cells were purchased from InvivoGen. For this assay, a transduced cell line designated herein as Ramos Blue Cells #4, was prepared by transducing Ramos-Blue™ Cells with human CD32 (FcγRII). Both types of Ramos-Blue™ cells were cultures in Ramos Cell Culture Medium (Iscove's Modified Dulbecco's Medium (IMDM) supplemented with 10% Fetal Bovine Serum (FBS), 2 mM L-Glutamine, penicillin and streptomycin (100 U/mL, −100 ug/mL), 100 ug/mL of Normomicin, and Zeocin as drug selection (100 ug/mL)). Cells were cultured at 37° C. in 5% $CO_2$. Both types of cells were passed every 3 days and maintained at a cell density of 0.5×10⁶ cell/ml. Cells were used until cell passage #21 (P21). After P21, the cells were discarded.

The assay was performed as follows. "AIM V™ medium" refers to serum free medium supplemented with L-glutamine, 50 μg/mL streptomycin sulfate, 10 μg/mL gentamicin sulfate (Thermo Fisher Scientific). To assess CD40 agonist activity by CD40 antagonist antibodies on the NF-kB/AP-1 activity in Ramos Blue Cells #4, cells were washed twice (2×) with AIM V™ medium without antibiotics Normocin/Zeocin. The cells were then centrifuged at room temperature for 10 minutes at 2,000 rpm. Medium was aspirated carefully to not disrupt the cell pellet. One (1) mL of AIM V™ was added to the cell pellet to re-suspend the cell pellet, and an additional 9 ml of AIM V™ was added after resuspension. Cells were counted using the cell counter by adding 20 microliters (μl) ViaStain™ AOPI (acridine orange/propidium iodide) staining solution (Nexcelom Bioscience, LLC, Lawrence, MA) and 20 μl of Ramos-Blue™ Cells suspension.

Ramos-Blue™ Cells were adjusted to 4×10⁶ cell/mL in AIM V™ serum free medium. One hundred (100)μl of 400K Ramos-Blue™ Cells were added per well in a flat bottom tissue culture plate. Then, 100 μl of BMS-986325, BMS-986090, mAb134-2141 (CD40-2142), or control was added to each corresponding well. CD40L-IZ was used as positive control. Ramos-Blue™ cells (0.4×10⁶ cells/well) in AIM V™ were included as negative control for the assay. The final volume was 200 μl/well.

Plates were incubated at 37° C. in a 5% $CO_2$ incubator for 20 hours. After 20 hours of cell culture, plates were centrifuged for 10 minutes at 2000 rpm.

Forty (40) μl of cell culture supernatant from stimulated Ramos cells were added to wells of a flat bottom plate. Then, 160 μl of QUANTI-Blue™ Solution was added per well. The final volume was 200 μl/well.

Plates were incubated at 37° C. in a 5% $CO_2$ incubator for 1 to 6 hours. SEAP levels were measured every 60 minutes at 620 nm using the EnVision® Reader Optical (OD: 620 nm).

Exemplary data are depicted in FIG. 6. In this example, anti-CD40 monoclonal antibodies were tested against Ramos-Blue™ Cells lacking CD32 or Ramos-Blue™ Cells transduced with CD32 (Ramos Blue #4) by assessing the NFκ-B/AP-1 inducible SEAP activity on Ramos-Blue™ Cells upon stimulation with anti-CD40 antibodies.

Figure 6A:
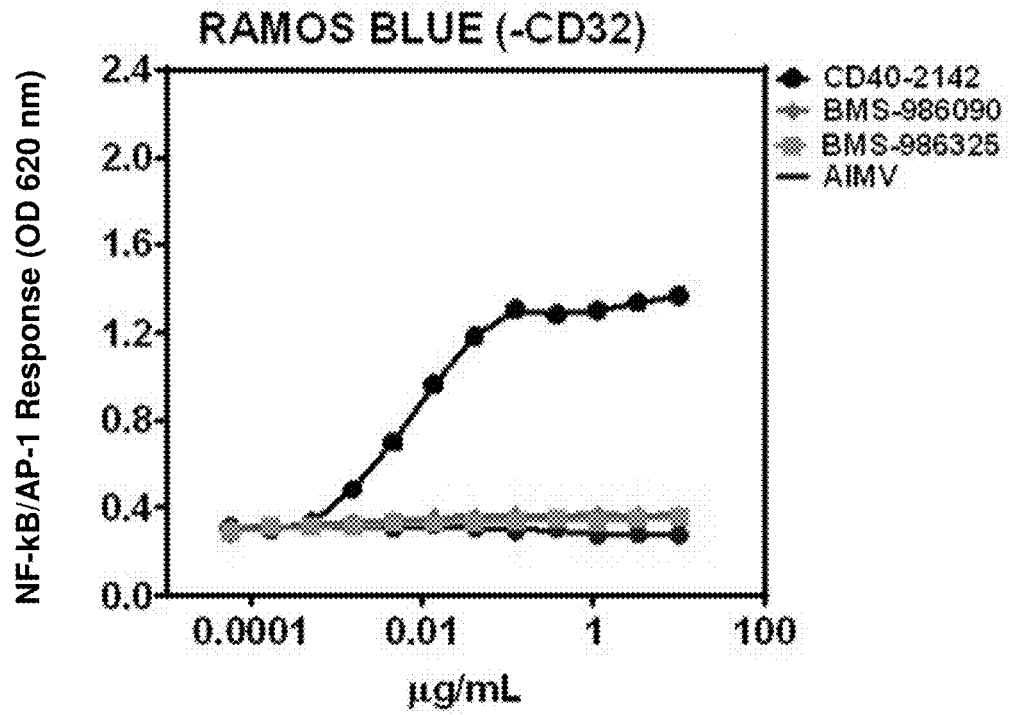
FIGS. 6A, 6B, 6C, and 6D depict data from an assay designed to assess the NF-kB/AP-1 inducible SEAP activity on Ramos Blues Cells upon stimulation with different anti-CD40 antibodies Representative results from three independent studies for the activity of CD40 mAbs are shown in FIGS. 6A and 6B.
Figure 6B:
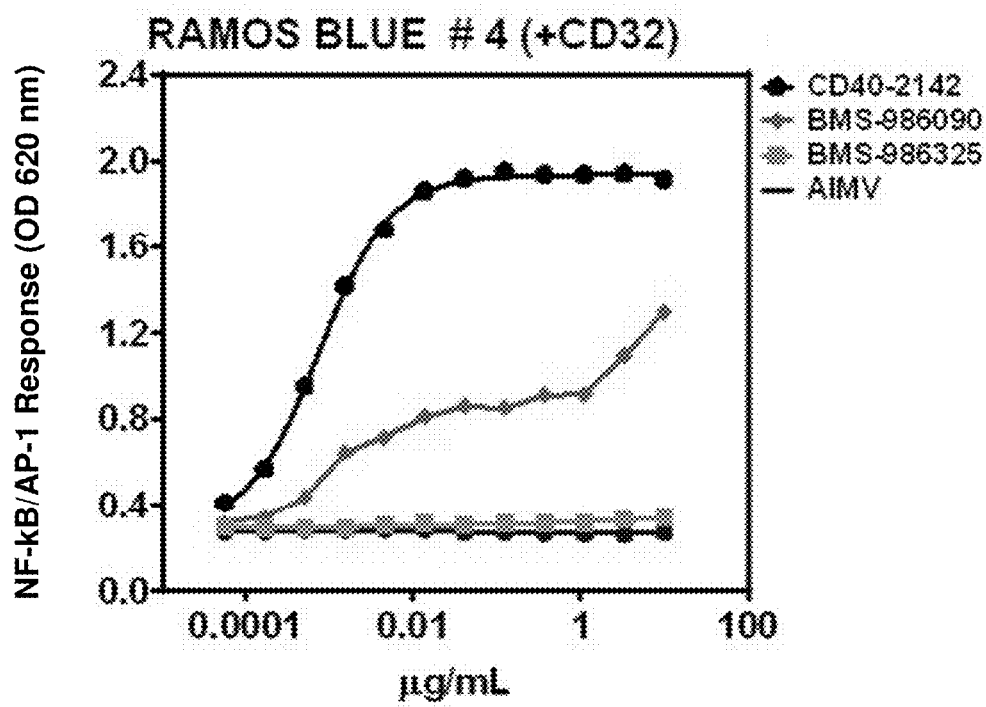
Figure 6C:
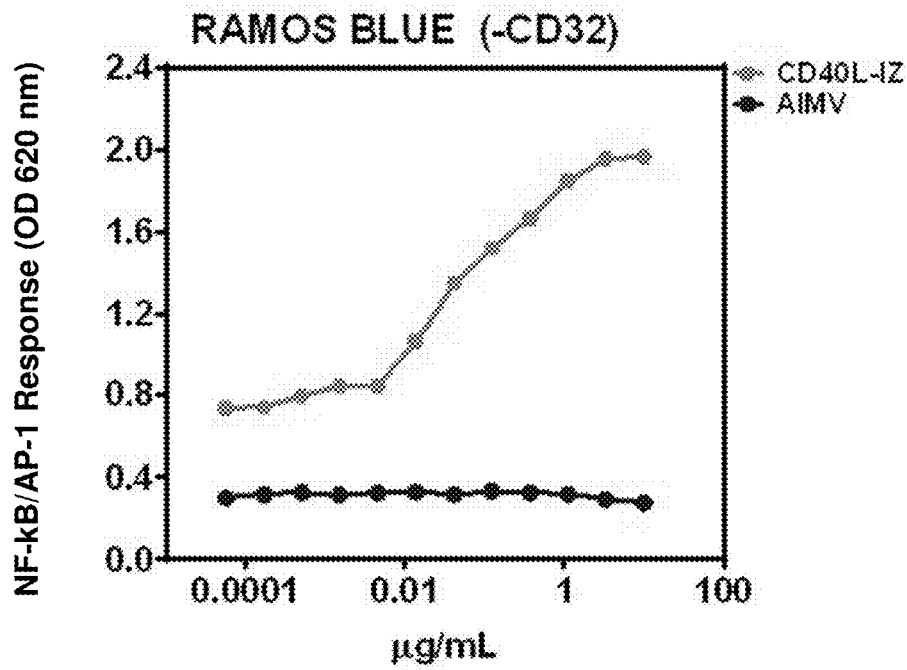
Figure 6D:
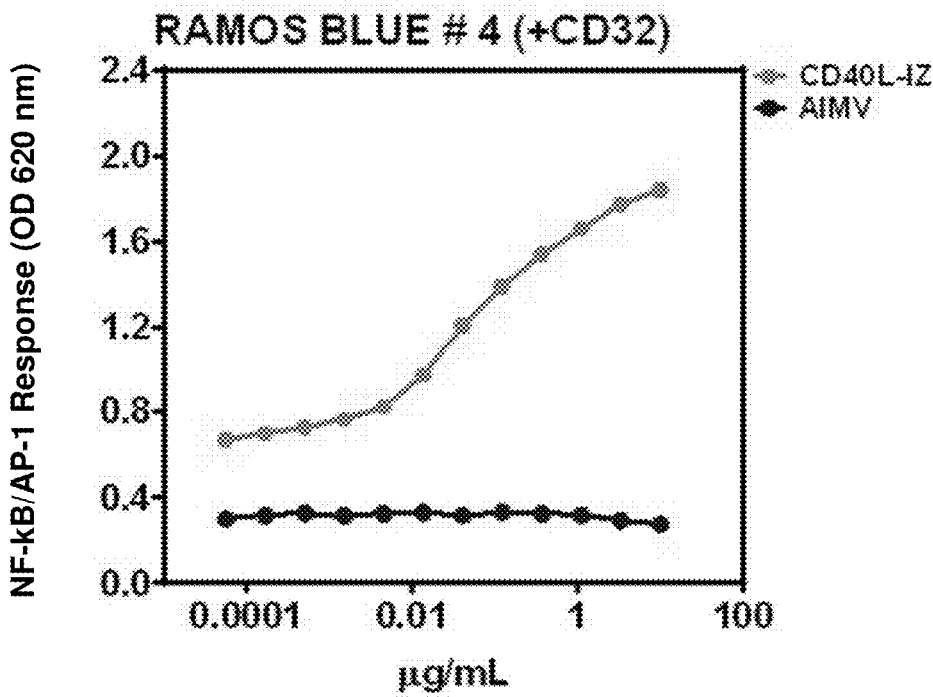

Addition of CD40-2142 induced a significant signaling response in this assay FIGS. 6A and 6b). These results indicate that CD40-2142 is a full agonist in this assay system. Addition of BMS-986090 showed no response by using the Ramos-Blue™ Cells (-CD32) (FIG. 6A), but displayed a partial agonism in the assay using the Ramos Blue Cells #4 (Ramos-Blue™ Cells transduced with CD32) (FIG. 6B). This result indicates FcγR dependency mediates the agonistic response induced by addition of BMS-986090. The control polypeptide, trimer CD40L-IZ, induced a response in both assays as reflected in FIGS. 6C and 6D.

In contrast, addition of BMS-986325 did not induce a significant NFκ-B/AP-1 response using either Ramos-Blue™ Cells (CD32⁻) (FIG. 6A) or Ramos #4 (CD32⁺) (FIG. 6B). These data indicate that BMS-986325 did not agonize CD40 and did not engage CD32 (FcγRII). These data support that reduced engagement of low affinity FcγRs, such as CD32 (FcγRII), reduces the likelihood of undesirable agonist signaling and undesirable potential for toxicity.

Example 7: Summary of Non-Clinical Pharmacokinetics Evaluation of BMS-986325

The pharmacokinetics (PK) of BMS-986325 (Y12XX-hz28-P238K) were evaluated in mice and cynomolgus monkeys. Since BMS-986325 does not cross react to murine CD40 receptors, the PK evaluated in mice is intrinsic or non-specific PK. BMS-986325 cross reacts with monkey CD40 receptors, therefore the total PK (specific and non-specific PK) was evaluated in monkeys. After intravenous (IV) administration of BMS-986325 (single 1- and 10-mg/kg doses) to mice, BMS-986325 exhibited low total serum clearance "CLT" of 0.5 to 1.02 mL/d/kg, limited volume of distribution at steady state "Vss" of 0.12 to 0.19 L/kg, and long apparent elimination half-life "T-HALF" of 118 to 183 hours (~5 to 8 days).

In monkeys, a single subcutaneous (SC) dose of BMS-986325 was administered. The dose administered is a dose at which specific clearance (target-mediated drug disposition "TMDD") is not saturated. After the single SC dose, BMS-986325 was well absorbed, with an absolute bioavailability of 70.4% (relative to exposures at the same IV dose). After IV administration of BMS-986325 (10 mg/kg single dose) to monkeys, BMS-986325 exhibited a CLT of 0.41 mL/d/kg, a limited Vss of 0.05 L/kg, and a T-HALF of 100 hours (~4 days). The time to maximum plasma concentration "Tmax" following a single SC dose of BMS-986325 (doses of 1, 10, and 100 mg/kg administered) to monkeys was 24 to 54 hours. There were more-than-dose-proportional increases in exposure (maximum concentration "Cmax" and area under the concentration vs time curve extrapolated from time zero to infinity "AUC[INF]") and an increase in T-HALF with dose (~31, ~119, and ~197 hours at 1, 10, and 100 mg/kg, respectively). These data suggest nonlinear PK and a saturable clearance mechanism; this likely results from target (CD40)-mediated clearance, reflecting TMDD. In this single-dose PK study, anti-drug antibody (ADA) formation was detected in ~50% of monkeys, but had no apparent impact on the overall PK parameters.

Pharmacokinetic/pharmacodynamic modeling (TMDD model with quasi steady-state assumption [TMDD-Qss]) was used to describe the nonlinear PK observed in monkeys, establish a relationship between serum drug exposure and CD40 receptor occupancy (RO) and subsequent human dose projection.

Although the present embodiments have been described in detail with reference to examples above, it is understood that various modifications can be made without departing from the spirit of these embodiments, and would readily be known to the skilled artisan.

These and other aspects disclosed herein, including the exemplary specific treatment methods, medicaments, and uses listed herein, will be apparent from the teachings contained herein.

The invention claimed is:

1. A pharmaceutical composition comprising: a) an antibody, or antigen binding portion thereof, that specifically binds to human CD40; and b) a pharmaceutically acceptable carrier,
wherein said antibody, or antigen binding portion thereof, comprises a first polypeptide portion comprising a heavy chain variable region and a second polypeptide portion comprising a light chain variable region, wherein said heavy chain variable region comprises the amino acid sequence of SEQ ID NO: 13 and said light chain variable region comprises the amino acid sequence of SEQ ID NO: 16.

2. The pharmaceutical composition of claim 1, wherein the antibody or antigen binding portion thereof antagonizes a CD40 activity.

3. The pharmaceutical composition of claim 1, wherein the first polypeptide portion further comprises a human heavy chain constant region, and the second polypeptide portion further comprises a human light chain constant region.

4. The pharmaceutical composition of claim 3, wherein the human heavy chain constant region comprises the amino acid sequence of amino acids 118-215 of SEQ ID NO: 5, and the human light chain constant region comprises the amino acid sequence of amino acids 108-214 of SEQ ID NO: 11.

5. The pharmaceutical composition of claim 3, wherein the human heavy chain constant region is a human IgG1 Fc domain comprising either
(1) a mutation at Kabat position 238 that reduces binding to Fc-gamma-receptors (FcγRs), wherein proline 238 (P238) is mutated to one of the residues selected from the group consisting of: lysine, serine, alanine, arginine, and tryptophan, and wherein the antibody or antigen binding portion thereof has reduced FcγR binding; or
(2) an alanine substituted at Kabat position 297.

6. The pharmaceutical composition of claim 5, wherein the human heavy chain constant region is a human IgG1 Fc domain comprising a mutation at Kabat position 238 that reduces binding to FcγRs, wherein proline 238 (P238) is mutated to one of the residues selected from the group consisting of: lysine, serine, alanine, arginine, and tryptophan, and wherein the antibody or antigen binding portion thereof has reduced FcγR binding.

7. The pharmaceutical composition of claim 6, wherein the human heavy chain constant region is a human IgG1 Fc domain comprising Kabat position 238 mutated to lysine.

8. The pharmaceutical composition of claim 7, wherein the human IgG1 Fc domain is an amino acid sequence selected from: SEQ ID NO: 22, SEQ ID NO: 23, SEQ ID NO: 24, SEQ ID NO: 25, SEQ ID NO: 26, SEQ ID NO: 27, SEQ ID NO: 28, or SEQ ID NO: 29.

9. The pharmaceutical composition of claim 7, wherein the human IgG1 Fc domain is an amino acid sequence selected from: SEQ ID NO: 22 or SEQ ID NO: 23.

10. The pharmaceutical composition of claim 1, wherein the first polypeptide portion comprises an amino acid sequence selected from the group consisting of: SEQ ID NO: 14 and SEQ ID NO: 15; and the second polypeptide portion comprises the amino acid sequence of SEQ ID NO: 17.

11. The pharmaceutical composition of claim 1, wherein the first polypeptide portion consists of an amino acid sequence selected from the group consisting of: SEQ ID NO: 14 and SEQ ID NO: 15; and the second polypeptide portion comprises the amino acid sequence of SEQ ID NO: 17.

12. The pharmaceutical composition of claim 1, wherein the antibody or antigen binding portion thereof is humanized.

13. The pharmaceutical composition of claim 1, wherein the antibody or antigen binding portion thereof is an scFv-Fc.

14. The pharmaceutical composition of claim 1, wherein the antibody or antigen binding portion thereof:
(i) is linked to a therapeutic agent;
(ii) is linked to a second functional moiety having a different binding specificity than said antibody or antigen binding portion thereof;
(iii) further comprises an additional moiety; or
(iv) any combination thereof.

15. A method of treating or preventing at least one of an immune response, an autoimmune disease, and an inflammatory disease in a subject, comprising administering to the subject the pharmaceutical composition of claim 1.

16. The method of claim 15, wherein the pharmaceutical composition is administered with an immunosuppressive, immunomodulatory and/or anti-inflammatory agent.

17. The method of claim 15, wherein the subject has a disease selected from the group consisting of: Addison's disease, allergies, anaphylaxis, ankylosing spondylitis, asthma, atherosclerosis, atopic allergy, autoimmune diseases of the ear, autoimmune diseases of the eye, autoimmune hepatitis, autoimmune parotitis, bronchial asthma, coronary heart disease, Crohn's disease, diabetes, epididymitis, glomerulonephritis, Graves' disease, Guillain-Barre syndrome, Hashimoto's disease, hemolytic anemia, idiopathic thrombocytopenia purpura, inflammatory bowel disease, an immune response to recombinant drug products, lupus nephritis, systemic lupus erythematosus, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, vasculitis, and ulcerative colitis.

18. The method of claim 15, wherein the subject has Sjogren's syndrome.

\* \* \* \* \*